(12) United States Patent
Spector et al.

(10) Patent No.: US 11,058,709 B1
(45) Date of Patent: Jul. 13, 2021

(54) METHODS OF TREATING BREAST CANCER

(71) Applicants: Cold Spring Harbor Laboratory, Cold Spring Harbor, NY (US); Ionis Pharmaceuticals, Inc., Carlsbad, CA (US)

(72) Inventors: David L. Spector, Cold Spring Harbor, NY (US); Sarah Daniela Diermeier, Centerport, NY (US); Frank Rigo, Carlsbad, CA (US); C. Frank Bennett, Carlsbad, CA (US); Susan M. Freier, San Diego, CA (US); Gayatri Arun, Huntington, NY (US); Kung-Chi Chang, Cold Spring Harbor, NY (US)

(73) Assignees: Ionis Pharmaceuticals, Inc., Carlsbad, CA (US); Cold Spring Harbor Laboratory, Cold Spring Harbor, NY (US)

( * ) Notice: Subject to any disclaimer, the term of this patent is extended or adjusted under 35 U.S.C. 154(b) by 264 days.

(21) Appl. No.: 15/781,249

(22) PCT Filed: Dec. 5, 2016

(86) PCT No.: PCT/US2016/064998
§ 371 (c)(1),
(2) Date: Jun. 4, 2018

(87) PCT Pub. No.: WO2017/096395
PCT Pub. Date: Jun. 8, 2017

Related U.S. Application Data

(60) Provisional application No. 62/378,125, filed on Aug. 22, 2016, provisional application No. 62/263,484, filed on Dec. 4, 2015.

(51) Int. Cl.
| | | |
|---|---|---|
| *A61K 31/713* | (2006.01) |
| *A61P 35/00* | (2006.01) |
| *A61K 31/175* | (2006.01) |
| *A61K 31/712* | (2006.01) |
| *A61K 31/7125* | (2006.01) |
| *C07H 21/04* | (2006.01) |
| *C12N 15/113* | (2010.01) |

(52) U.S. Cl.
CPC .......... *A61K 31/713* (2013.01); *A61K 31/175* (2013.01); *A61K 31/712* (2013.01); *A61K 31/7125* (2013.01); *A61P 35/00* (2018.01); *C07H 21/04* (2013.01); *C12N 15/113* (2013.01); *A61K 2300/00* (2013.01)

(58) Field of Classification Search
CPC .......... C12Q 1/6886; C12Q 2600/178
USPC .... 435/6.1, 91.1, 91.31, 455, 458; 536/23.1, 536/24.5; 514/44 A
See application file for complete search history.

(56) References Cited

U.S. PATENT DOCUMENTS

| | | |
|---|---|---|
| 3,687,808 A | 8/1972 | Merigan et al. |
| 4,415,732 A | 11/1983 | Caruthers et al. |
| 4,458,066 A | 7/1984 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,668,777 A | 5/1987 | Caruthers et al. |
| 4,725,677 A | 2/1988 | Koster et al. |
| 4,845,205 A | 7/1989 | Huynh Dinh et al. |
| 4,973,679 A | 11/1990 | Caruthers et al. |
| 4,981,957 A | 1/1991 | Lebleu et al. |
| 5,013,830 A | 5/1991 | Ohutsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,188,897 A | 2/1993 | Suhadolnik et al. |
| 5,194,599 A | 3/1993 | Froehler et al. |
| 5,214,134 A | 5/1993 | Weis et al. |
| 5,216,141 A | 6/1993 | Benner |
| 5,220,007 A | 6/1993 | Pederson et al. |
| 5,223,618 A | 6/1993 | Cook et al. |
| 5,235,033 A | 8/1993 | Summerton et al. |
| 5,256,775 A | 10/1993 | Froehler |
| 5,264,423 A | 11/1993 | Cohen et al. |

(Continued)

FOREIGN PATENT DOCUMENTS

| | | |
|---|---|---|
| WO | WO 2000/063364 | 10/2000 |
| WO | WO 2010/138806 A2 | 12/2010 |

(Continued)

OTHER PUBLICATIONS

Huarte, M, Nature Medicine, vol. 21, No. 11, pates 1253-1261. (Year: 2015).*

(Continued)

*Primary Examiner* — Jane J Zara
(74) *Attorney, Agent, or Firm* — Michael Best & Friedrich LLP

(57) ABSTRACT

Provided herein are methods, compounds, and compositions for reducing expression of a MaTAR in an animal. Such methods, compounds, and compositions are useful to treat, prevent, delay, or ameliorate breast cancer in an individual in need.

15 Claims, No Drawings
Specification includes a Sequence Listing.

(56) References Cited

U.S. PATENT DOCUMENTS

| | | |
|---|---|---|
| 5,264,562 A | 11/1993 | Matteucci |
| 5,264,564 A | 11/1993 | Matteucci |
| 5,185,444 A | 12/1993 | Summerton et al. |
| 5,276,019 A | 1/1994 | Cohen et al. |
| 5,278,302 A | 1/1994 | Caruthers et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,378,825 A | 1/1995 | Cook et al. |
| 5,386,023 A | 1/1995 | Sanghvi et al. |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Sumerton et al. |
| 5,405,939 A | 4/1995 | Suhadolnik et al. |
| 5,432,272 A | 7/1995 | Benner |
| 5,434,257 A | 7/1995 | Matteucci |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmelner et al. |
| 5,457,191 A | 10/1995 | Cook et al. |
| 5,459,255 A | 10/1995 | Cook et al. |
| 5,466,677 A | 11/1995 | Baxter et al. |
| 5,466,786 A | 11/1995 | Burh et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,133 A | 2/1996 | Walder et al. |
| 5,502,177 A | 3/1996 | Matteucci et al. |
| 5,508,270 A | 4/1996 | Baxter et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,555 A | 10/1996 | Froehler et al. |
| 5,567,811 A | 10/1996 | Mistura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,587,470 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bishofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci |
| 5,652,355 A | 7/1997 | Metelev et al. |
| 5,652,356 A | 7/1997 | Agrawal |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,698,685 A | 12/1997 | Summerton et al. |
| 5,700,920 A | 12/1997 | Altmann et al. |
| 5,700,922 A | 12/1997 | Cook |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,847 A | 8/1998 | Burh et al. |
| 5,801,154 A | 9/1998 | Baracchini et al. |
| 5,808,027 A | 9/1998 | Cook et al. |
| 5,830,653 A | 11/1998 | Froehler et al. |
| 5,859,221 A | 1/1999 | Cook et al. |
| 5,948,903 A | 9/1999 | Cook et al. |
| 5,994,517 A | 11/1999 | Ts'O |
| 6,005,087 A | 12/1999 | Cook et al. |
| 6,005,096 A | 12/1999 | Matteucci et al. |
| 6,166,199 A | 12/2000 | Cook et al. |
| 6,268,490 B1 | 7/2001 | Imanishi et al. |
| 6,300,319 B1 | 10/2001 | Manoharan |
| 6,426,220 B1 | 7/2002 | Bennett et al. |
| 6,525,191 B1 | 2/2003 | Ramasamy |
| 6,531,584 B1 | 3/2003 | Cook et al. |
| 6,582,908 B2 | 6/2003 | Fodor et al. |
| 6,600,032 B1 | 7/2003 | Manoharan et al. |
| 6,660,720 B2 | 12/2003 | Manoharan |
| 6,670,461 B1 | 12/2003 | Wengel et al. |
| 6,673,661 B1 | 1/2004 | Liu et al. |
| 6,770,748 B2 | 8/2004 | Imanishi et al. |
| 6,794,499 B2 | 9/2004 | Wengel et al. |
| 6,906,182 B2 | 6/2005 | Ts'o et al. |
| 7,015,315 B1 | 3/2006 | Cook et al. |
| 7,034,133 B2 | 4/2006 | Wengel et al. |
| 7,053,207 B2 | 5/2006 | Wengel et al. |
| 7,101,993 B1 | 9/2006 | Cook et al. |
| 7,262,177 B2 | 8/2007 | Ts'o et al. |
| 7,399,845 B2 | 7/2008 | Seth et al. |
| 7,427,672 B2 | 9/2008 | Imanishi et al. |
| 7,491,805 B2 | 2/2009 | Vargeese et al. |
| 7,547,684 B2 | 6/2009 | Seth et al. |
| 7,569,686 B1 | 8/2009 | Bhat et al. |
| 7,572,582 B2 | 8/2009 | Wengel et al. |
| 7,666,854 B2 | 2/2010 | Seth et al. |
| 7,696,345 B2 | 4/2010 | Allerson et al. |
| 7,723,509 B2 | 5/2010 | Manoharan et al. |
| 7,741,457 B2 | 6/2010 | Swayze et al. |
| 7,750,131 B2 | 7/2010 | Seth et al. |
| 7,875,733 B2 | 1/2011 | Bhat et al. |
| RE34,036 E | 3/2011 | McGeehan |
| 7,939,677 B2 | 5/2011 | Bhat et al. |
| 8,022,193 B2 | 9/2011 | Swayze et al. |
| 8,030,467 B2 | 10/2011 | Seth et al. |
| 8,034,909 B2 | 10/2011 | Wengel et al. |
| 8,080,644 B2 | 12/2011 | Wengel et al. |
| 8,088,746 B2 | 1/2012 | Seth et al. |
| 8,088,904 B2 | 1/2012 | Swayze et al. |
| 8,106,022 B2 | 1/2012 | Manoharan et al. |
| 8,124,745 B2 | 2/2012 | Allerson et al. |
| 8,153,365 B2 | 4/2012 | Wengel et al. |
| 8,268,980 B2 | 9/2012 | Seth et al. |
| 8,278,283 B2 | 10/2012 | Seth et al. |
| 8,278,425 B2 | 10/2012 | Prakash et al. |
| 8,278,426 B2 | 10/2012 | Seth et al. |
| 8,440,803 B2 | 5/2013 | Swayze et al. |
| 8,501,805 B2 | 8/2013 | Seth et al. |
| 8,530,640 B2 | 9/2013 | Seth et al. |
| 8,546,556 B2 | 10/2013 | Seth et al. |
| RE44,779 E | 2/2014 | Imanishi et al. |
| 8,828,956 B2 | 9/2014 | Manoharan et al. |
| 9,005,906 B2 | 4/2015 | Swayze et al. |
| 9,012,421 B2 | 4/2015 | Migawa et al. |
| 9,062,351 B2 | 6/2015 | Chang et al. |

(56) References Cited

U.S. PATENT DOCUMENTS

| | | | |
|---|---|---|---|
| 9,127,276 | B2 | 8/2015 | Prakash et al. |
| 9,290,760 | B2 | 3/2016 | Rajeev et al. |
| 2001/0053519 | A1 | 12/2001 | Fodor et al. |
| 2003/0082807 | A1 | 5/2003 | Wengel |
| 2003/0158403 | A1 | 8/2003 | Manoharan et al. |
| 2003/0175906 | A1 | 9/2003 | Manoharan et al. |
| 2003/0207841 | A1 | 11/2003 | Kaneko et al. |
| 2003/0224377 | A1 | 12/2003 | Wengel et al. |
| 2003/0228597 | A1 | 12/2003 | Cowsert et al. |
| 2004/0143114 | A1 | 7/2004 | Imanishi et al. |
| 2004/0171570 | A1 | 9/2004 | Allerson et al. |
| 2004/0192918 | A1 | 9/2004 | Imanishi et al. |
| 2005/0130923 | A1 | 6/2005 | Bhat et al. |
| 2006/0148740 | A1 | 7/2006 | Platenburg |
| 2007/0031844 | A1 | 2/2007 | Khvorova et al. |
| 2008/0039618 | A1 | 2/2008 | Allerson et al. |
| 2010/0190837 | A1 | 7/2010 | Migawa et al. |
| 2010/0197762 | A1 | 8/2010 | Swayze et al. |
| 2011/0123520 | A1 | 5/2011 | Manoharan et al. |
| 2013/0130378 | A1 | 5/2013 | Manoharan et al. |
| 2013/0178428 | A1 | 7/2013 | Hoon et al. |
| 2013/0203836 | A1 | 8/2013 | Rajeev et al. |
| 2013/0267575 | A1 | 10/2013 | Safe et al. |
| 2014/0107330 | A1 | 4/2014 | Freier et al. |
| 2014/0242192 | A1 | 8/2014 | Cormack et al. |
| 2015/0018540 | A1 | 1/2015 | Prakash et al. |
| 2015/0184153 | A1 | 7/2015 | Freier et al. |
| 2015/0191727 | A1 | 7/2015 | Migawa et al. |
| 2015/0267195 | A1 | 9/2015 | Seth et al. |
| 2015/0275212 | A1 | 10/2015 | Albaek et al. |

FOREIGN PATENT DOCUMENTS

| | | | |
|---|---|---|---|
| WO | WO 2012/058268 | A2 | 5/2012 |
| WO | 2013/066721 | A2 | 5/2013 |
| WO | WO 2013/066821 | A2 | 5/2013 |
| WO | WO 2014/205555 | | 12/2014 |

OTHER PUBLICATIONS

Ali et al., "Endocrine-responsive breast cancer and strategies for combating resistance" Nat Rev Cancer (2002) 2(2): 101-112.
Anders et al., "HTSeq—a Python framework to work with high-throughput sequencing data" Bioinformatics (2015) 31(2): 166-169.
Anderson et al., "Tracking and evaluating molecular tumor markers with cancer registry data: HER2 and breast cancer" J Natl Cancer Inst (2014) 106(5): 1-3.
Anderson et al., "How many etiological subtypes of breast cancer: two, three, four, or more?" J Natl Cancer Inst (2014) 106(8): 1-11.
Andrechek et al., "Amplification of the neu/erbB-2 oncogene in a mouse model of mammary tumorigenesis" PNAS (2000) 97: 3444-3449.
Arase et al., "Transforming growth factor-β-induced lncRNA-Smad7 inhibits apoptosis of mouse breast cancer JygMC(A) cells." Cancer Sci. (2014) 105: 974-982.
Arun et al., "Differentiation of mammary tumors and reduction in metastasis upon Malat1 lncRNA loss" Genes & Development (2016) 30: 34-51.
Arun et al., "Therapeutic Targeting of Long Non-Coding RNAs in Cancer" Trends in Mol. Med. (2018) 24(3): 257-277.
Barcellos-Hoff et al., "Functional differentiation and alveolar morphogenesis of primary mammary culatures on reconstituted basement membrane" Development (1989) 105: 223-235.
Bergmann et al., "Long non-coding RNAs: modulators of nuclear structure and function" Curr. Opin. Cell Biol. (2014) 26: 10-18.
Bergmann et al., "Regulation of the ESC transcriptome by nuclear long noncoding RNAs" Genome Res (2015) 25: 1336-1346.
Bertone et al., "Global identification of human transcribed sequences with genome tiling arrays" Science (2004) 306: 224202246.
Boj et al., "Organoid Models of Human and Mouse Ductal Pancreatic Cancer" Cell (2015) 160: 324-338.
Branch et al., "A good antisense molecule is hard to find," TIBS (1998) 23:45-50.
Bundy et al., "CCAAT/enhancer binding protein beta (C/EBPβ-2 transforms normal mammary epithelial cells and induces epithelial to mesenchymal transition in culture" Oncogene (2003) 22: 869-883.
Cabili et al., "Integrative annotation of human large intergenic noncoding RNAs reveals global properties and specific subclasses" Genes & Development (2011) 25: 1915-1927.
The Cancer Genome Atlas Network, "Comprehensive molecular portraits of human breast tumours" Nature (2012) 490: 61-70.
Carninci et al., "The transcriptional landscape of the mammalian genome" Science (2005) 309: 1559-1563.
Chang et al., "Androgen receptor (AR) differential roles in hormone-related tumors indcluding prostate, bladder, kidney, lung, breast and liver" Oncogene (2013) 1-10.
Cheetham et al., "Long noncoding RNAs and the genetics of cancer" British Journal of Cancer (2013) 108: 2419-2425.
Cheung et al., "Collective Invasion in Breast Cancer Requires a Conserved Basal Epithelial Program" Cell (2013) 155: 1639-1651.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Chou et al., "HSF1 regulation of β-catenin in mammary cancer cells through control of HuR/elavL1 expression" Oncogene (2015) 34: 2178-2188.
Clevers, "Modeling Development and Disease with Organoids" Cell (2016) 165: 1586-1597.
Crooke et al., "Basic Principles of Antisense Therapeutics" Antisense Research and Application (1998) Chapter 1:1-50.
Derrien et al., "The GENCODE v7 catalog of human long noncoding RNAs: Analysis of their gene structure, evolution, and expression" Genome Res. (2012) 22: 1775-1789.
Diederichs, "The four dimensions of noncoding RNA conservation." Trends in Genetics (2014) 30: 121-123.
Diermeier et al., "Mammaly Tumor-Associate RNAs Impact Tumor Cell Proliferation, Invasion, and Migration" Cell Rep (2016) 17: 261-274.
Diermeier et al., "Abstract A43: Long noncoding RNAs as targets of mammary tumor cell proliferation and migration" Cancer Research (2016) 76(6).
Diermeier et al., "Antisense Oligonucleotide-mediated Knockdown in Mammaly Tumor Organoids" Bio-Protocol (2017) 7(16): 1-13.
Dimitrova et al., "LncRNA-p21 activates p21 in cis to promote polycomb target gene expression and to enforce he G1/S checkpoint" Molecular Cell (2014) 54: 777-790.
Djebali et al., "Landscape of transcription in human cells" Nature (2012) 489: 101-108.
Dobin et al., "STAR: ultrafast universal RNA-seq aligner" Bioinformatics (2013) 29: 15-21.
Domcke et al., "Evaluating cell lines as tumour models by comparison of genomic profiles" Nature Communications (2013) 4: 2126.
Eden et al., "GOrilla: a tool for discovery and visualization of enriched GO terms in ranked gene lists" BMC Bioinformatics (2009) 10: 48.
Ewald, "Isolation of mouse mammary organoids for long-term time-lapse imaging" Cold Spring Harb. Protoc. (2013) 130-133.
Ewald et al., "Collective epithelial Migration and Cell Rearrangements Drive Mammaly Branching Morphogenesis" Developmental Cell (2008) 14: 570-581.
Fabregat et al., "The reactome pathway knowledgebase" Nucleic Acids Res (2016) 44: D481-D487.
Fata et al., "The MAPKERK-1,2 pathway integrates distinct and antagonistic signals from TGFα and FGF7 in morphogenesis of mouse mammary epithelium" Developmental Biology (2007) 306: 193-207.
Geary et al., "Pharmacokinetics, biodistribution and cell uptake of antisense oligonucleotides" Adv. Drug Deliv. Rev. (2015) 87: 46-51.
Gupta et al., "Long non-coding RNA HOTAIR reprograms chromatin state to promote cancer metastasis" Nature (2010) 464: 1071-1076.

(56) References Cited

OTHER PUBLICATIONS

Guy et al., "Induction of mammary tumors by expression of polyomavirus middle T oncogene: a transgenic mouse model for metastatic disease" Molecular and Cellular Biology (1992) 12: 954-961.
Hansji et al., "Keeping abreast with long non-coding RNAs in mammary gland development and breast cancer" Front Genet (2014) 5: 379.
Heinz et al., "Simple Combinations of Lineage-Determining Transcription Factors Prime cis-Regulatory Elements Required for Macrophage and B Cell Identities" Molecular Cell (2010) 38: 576-589.
Higgins et al., "Targeted therapies for breast cancer" J Clin Invest (2011) 121(10): 3797-3803.
Huarte, "The emerging role of lncRNAs in cancer" Nature Medicine (2015) 21: 1253-1261.
Huarte et al., "A large intergenic noncoding RNA induced by p53 mediates global gene repression in the p53 response" Cell (2010) 142: 409-419.
Huber et al., "NF-KB is essential for epithelial-mesenchymal transition and metastasis in a model of breast cancer progression" J. Clin. Invest. (2004) 114: 569-581.
International Search Report for PCT/US2016/064998 dated May 4, 2017.
Iyer et al., "The landscape of long noncoding RNAs in the human transcriptome" Nat. Genet. (2015) 47: 199-208.
Kapranov et al., "RNA maps reveal new RNA classes and a possible function for pervasive transcription" Science (2007) 316: 1484-1488.
Katayama et al., "Antisense transcription in the mammalian tmnscriptome" Science (2005) 309(5740): 1564-1566.
Koller et al., "Mechanisms of single-stranded phosphorothioate modified antisense oligonucleotide accumulation in hepatocytes" Nucleic Acids Res. (2011) 39: 4795-4807.
Koller et al., "Use of a chemically modified antisense oligonucleotide library to identify and validate Eg5 (kinesin-like 1) as a target for antineoplastic drug development" Cancer Research (2006) 66: 2059-2066.
Kornienko et al., "Gene regulation by the act of long non-coding RNA transcription" BMC Biol (2013) 11: 1-14.
Lancaster et al., "Organogenesis in a dish: Modeling development and disease using organoid technologies" Science (2014) 345: 1247125.
Langfelder et al., "WGCNA: an R package for weighted correlation network analysis" BMC Bioinformatics (2008) 9: 559.
Li et al., "RSEM: accurate transcript quantification from RNA-Seq data with or without a reference genome" BMC Bioinformatics (2011) 12: 323.
Lopes et al., "Kaiso Contributes to DNA Methylation-Dependent Silencing of Tumor Suppressor Genes in Colon Cancer Cell Lines" Cancer Research (2008) 68: 7258-7263.
Love et al., "Moderated estimation of fold change and dispersion for RNA-seq data with DESeq2" Genome Biol (2014) 15: 550.
Luo et al., "Pathview: an R/Bioconductor package for pathway-based data integration and visualization" Bioinformatics (2013) 29: 1830-1831.
Luo et al., "GAGE: generally applicable gene sest enrichment for pathway analysis" BMC Bioinformatics (2009) 10: 161.
New England Biolabs 1998/99 Catalog (cover page and pp. 121 and 284).
Nguyen-Ngoc et al., "ECM microenvironment regulates collective migration and local dissemination in normal and malignant mammary epithelium" PNAS (2012) 109: E2595-E2604.
Okazaki et al., "Analysis of the mouse transcriptome based on functional annotation of 60,770 full-length cDNAs" Nature (2002) 420: 563-573.
Parker et al., "Supervised Risk Predictor of Breast Cancer Based on Intrinsic Subtypes" Journal of Clinical Oncology (2009) 27: 1160-1167.
Perou et al., "Molecular portraits of human breast tumours" Nature (2000) 406(6797): 747-752.
Prensner et al., "The Emergence of lncRNAs in Cancer Biology" Cancer Discovery (2011) 1: 391-407.
Ran et al., "Genome engineering using the CRISPR-Cas9 system" Nat Protoc (2013) 8: 2281-2308.
Reynolds et al., "Rational siRNA design for RNA interference" Nature Biotechnology (2004) 22(3):326-330.
Rinn et al., "Genome Regulation by Long Noncoding RNAs" Annu. Rev. Biochem (2012) 81: 145-166.
Rinn et al., "Functional demarcation of active and silent chromatin domans in human HOX loci by noncoding RNAs" Cell (2007) 129: 1311-1323.
Sachs et al., "Organoid culture for the analysis of cancer phenotypes" Curr. Opin. Genet. Dev. (2014) 24: 68-73.
Sanghvi et al., "Heterocyclic Base Modifications in Nucleic Acids and Their Applications in Antisense Oligonucleotides" Antisense Research and Applications (1993) pp. 273-288.
Shamir et al., "Three-dimensional organotypic culture: experimental models of mammalian biology and disease" Nature Review Molecular Cell Biology (2014) 15: 647-664.
Shore et al., "Noncoding RNAs involved in mammary gland development and tumorigenesis: there's a long way to go" J. Mammary Gland Biol Neoplasia (2012) 17: 43-58.
Siegel et al., "Elevated expression of activate dforms of Neu/ErbB-2 and ErbB-3 are involved in the induction of mammary tumors in transgenic mice: implications for human breast cancer" The EMBO Journal (1999) 18: 2149-2164.
Siegel et al., "Cancer statistics, 2015" CA Cancer J Clin (2015) 65(1): 5-29.
Sorlie et al., "Repeated observation of breast tumor subtypes in independent gene expression data sets" Proc Natl Acad Sci USA (2003) 100(14): 8418-8423.
St Laurent et al., "Intronic RNAs constitute the major fraction of the non-coding RNA in mammalian cells" BMC Genomics (2012) 13: 504.
Subramanian et al., "Gene set enrichment analysis: a knowledge-based approach for interpreting genome-wide expression profiles" PNAS (2005) 102: 15545-15550.
Sun et al., "Discovery, annotation, and Functional Analysis of Long Noncoding RNAs Controlling Cell-Cycle Gene Expression and Proliferation in Breast Cancer Cells" Molecular Cell (2015) 59: 698-711.
Tomita et al., "A cluster of noncoding RNAs activates the ESR1 locus during breast cancer adaptation" Nature Communications (2015) 6: 6966.
Ulitsky et al., "Conserved Function of lncRNAs in Vertebrate Embryonic Develoment despite Rapid Sequence Evolution" Cell (2011) 147: 1537-1550.
Van Staveren et al., "Human cancer cell lines: Experimental models for cancer cells in situ? For cancer stem cells?" Biochim Biophys Acta (2009) 1795: 92-103.
Vikram et al., "Functional significance of long non-coding RNAs in breast cancer" Breast Cancer (2014) 21: 515-521.
Wahlestedt, "Targeting long non-coding RNA to therapeutically upregulate gene expression" Nat Rev Drug Discov (2013) 12: 433-446.
Wang et al., "CPAT: Coding-Potential Assessment Tool using and alignment-free logistic regression model" Nucleic Acids Res (2013) 41: e74.
Wapinski et al., "Long noncoding RNAs and human disease" Trends in Cell Biology (2011) 21: 354-361.
Xing et al., "lncRNA directs cooperative epigenetic regulation downstream of chemokine signals" Cell (2014) 159: 1110-1125.
Yan et al., "Comprehensive Genomic Characterization of Long Non-coding RNAs across Human Cancers" Cancer Cell (2015) 28: 529-540.
Yang et al., "Reciprocal regulation of HIF-1α and lncRNA-p21 modulates the Warburg effect" Molecular Cell (2014) 53: 88-100.
Zhang et al., "A myelopoiesis-associated regulatory intergenic noncoding RNA transcript within the human HOXA cluster" Blood (2009) 113: 2526-2534.

(56) References Cited

OTHER PUBLICATIONS

Zhang et al., "Long intergenic noncoding RNA HOTAIRM1 Regulates cell cycle progression during myeloid maturation in NB4 human promyelocytic leukemia cells" RNA Biology (2014) 11: 777-787.
Bhan et al., "Antisense Transcript Long Noncoding RNA (lncRNA) HOTAIR is Transcriptionally Induced by Estradiol" J Mol Biol (2013) 425(19): 3707-3722.
Crooke, ST., et al., "Antisense Drug Technology" Second Edition, CRC Press (2008) Chapters 1-28.
Egli, et al., "Synthesis, improved antisense activity and structural rationale for the divergent RNA affinities of 3'-fluoro hexitol nucleic acid (FHNA and Ara-FHNA) modified oligonucleotides." J Am Chem (2011) 133(41):16642-16649.
Gautschi et al., "Activity of a novel bcl-2/bcl-xLbispecific antisense oligonucleotide against tumors of diverse histologic origins" J. Natl. Cancer Inst. (2001) 93:463-471.
Maher et al., "Comparative hybrid arrest by tandem antisense oligodeoxyribonucleotides or oligodeoxyribonucleoside methylpbosphonates in a cell-free system" Nucl. Acid. Res. (1988) 16(8):3341-3358.
Seth et al., "Short Antisense Oligonucleotides with Novel 2'-4' Conformationaly Restricted Nucleoside Analogues Show Improved Potency Without Increased Toxicity in Animals." J Med Chem (2009) 52:10-13.
Woolf et al., "Specificity of antisense oligonucleotides in vivo" PNAS (1992) 89: 7305-7309.
Partial Search report for EP 16871732.0 dated Sep. 10, 2019.
European Patent Office Extended Search Report for Application No. 16871732.0 dated Dec. 11, 2019 (14 pages).

\* cited by examiner

METHODS OF TREATING BREAST CANCER

STATEMENT OF GOVERNMENT SUPPORT

This invention was made with Government support under CA013106 and GM042694 awarded by National Institute of Health. The government has certain rights in the invention.

SEQUENCE LISTING

The present application is being filed along with a Sequence Listing in electronic format. The Sequence Listing is provided as a file entitled BIOL0280USASEQ_ST25.txt, created on Jun. 1, 2018 which is 4.92 MB in size. The information in the electronic format of the sequence listing is incorporated herein by reference in its entirety.

FIELD OF THE INVENTION

Provided herein are methods, compounds, and compositions useful for reducing expression of long noncoding RNAs (lncRNAs), specifically, Mammary Tumor Associated RNAs (hereinafter referred to as MaTARs) in an animal. Also, provided herein are methods, compounds, and compositions comprising MaTAR inhibitors, which can be useful in reducing MaTAR-related diseases or conditions in an animal. Such methods, compounds, and compositions can be useful, for example, to treat, prevent, delay or ameliorate breast cancer in an animal.

BACKGROUND

Breast cancer is the most frequent malignancy in women worldwide and the second leading cause of cancer mortality in women (Siegel et al. Cancer Statistics, 2015. CA: A Cancer Journal for Clinicians 65: 5-29, 2015). The challenge of finding more efficient treatments is complicated by the diversity of the disease, resulting in the classification of numerous breast cancer subtypes. The most common type, invasive ductal carcinoma, can be stratified into two fundamental classes: the estrogen receptor (ER) and/or progesterone receptor (PR) positive subtypes (luminal A and luminal B) and ER-negative (HER2/neu-amplified and basal-like) disease. These "intrinsic" breast cancer subtypes differ in gene expression patterns, histo-pathology, patient prognosis and treatment strategy (Perou et al. Nature. 406: 747-752, 2000; Sorlie et al. Proc. Natl. Acad. Sci. USA 100: 8418-8423, 2003; Cancer Genome Atlas Network Nature. 490: 61-70, 2012; Anderson et al. J. Natl. Cancer Inst. 106, 2014).

While currently available endocrine and targeted therapies have lead to improved overall survival rates, many breast tumors are intrinsically resistant or acquire resistance after initial responsiveness (Ali and Coombes Nat. Rev. Cancer 2: 101-112, 2002; Higgins and Baselga J. Clin. Invest. 121: 3797-3803, 2011). To improve the existing treatment regimens, it is critical to identify and investigate new molecular targets that have the potential to inhibit breast cancer progression and metastasis by impacting alternative pathways and/or restoring drug sensitivity.

SUMMARY

Provided herein are compositions, compounds and methods for modulating expression of lncRNAs associated with breast cancer. In certain embodiments, these compositions, compounds and methods are for modulating the expression of mammary tumor associated RNAs (MaTARs). In certain embodiments, the MaTAR modulator is a MaTAR-specific inhibitor. In certain embodiments, the MaTAR-specific inhibitor decreases expression of a MaTAR. In certain embodiments, MaTAR-specific inhibitors include nucleic acids, proteins and small molecules. In certain embodiments, the MaTAR-specific inhibitor is a nucleic acid. In certain embodiments, the nucleic acid is a compound. In certain embodiments, the compound comprises a modified oligonucleotide. In certain embodiments, the modified oligonucleotide can be single stranded or double stranded.

Certain embodiments relate to the novel findings of a comprehensive catalog of lncRNAs that are upregulated in mammary tumors compared to mammary gland epithelia. Certain embodiments relate to the novel identification of MaTARs as the key drivers in tumor progression. Certain embodiments relate to the novel findings of MaTAR involvement in mammary tumor proliferation and carcinogenesis. Certain embodiments are directed to MaTAR inhibitors useful for inhibiting a MaTAR, which can be useful for treating, ameliorating, or slowing progression of breast cancer.

DETAILED DESCRIPTION OF THE INVENTION

It is to be understood that both the foregoing general description and the following detailed description are exemplary and explanatory only and are not restrictive of the embodiments, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting.

The section headings used herein are for organizational purposes only and are not to be construed as limiting the subject matter described. All documents, or portions of documents, cited in this application, including, but not limited to, patents, patent applications, articles, books, treatises, and GenBank and NCBI reference sequence records are hereby expressly incorporated by reference for the portions of the document discussed herein, as well as in their entirety.

It is understood that the sequence set forth in each SEQ ID NO in the examples contained herein is independent of any modification to a sugar moiety, an internucleoside linkage, or a nucleobase. As such, compounds defined by a SEQ ID NO may comprise, independently, one or more modifications to a sugar moiety, an internucleoside linkage, or a nucleobase. Compounds described by ISIS number (ISIS #) indicate a combination of nucleobase sequence, chemical modification, and motif.

Unless otherwise indicated, the following terms have the following meanings:

"2'-deoxynucleoside" means a nucleoside comprising 2'-H(H) furanosyl sugar moiety, as found in naturally occurring deoxyribonucleic acids (DNA). In certain embodiments, a 2'-deoxynucleoside may comprise a modified nucleobase or may comprise an RNA nucleobase (uracil).

"2'-O-methoxyethyl" (also 2'-MOE and 2'-O(CH$_2$)$_2$—OCH$_3$) refers to an O-methoxy-ethyl modification at the 2' position of a furanosyl ring. A 2'-O-methoxyethyl modified sugar is a modified sugar.

"2'-MOE nucleoside" (also 2'-O-methoxyethyl nucleoside) means a nucleoside comprising a 2'-MOE modified sugar moiety.

"2'-substituted nucleoside" or "2-modified nucleoside" means a nucleoside comprising a 2'-substituted or 2'-modified sugar moiety. As used herein, "2'-substituted" or "2-modified" in reference to a sugar moiety means a sugar moiety comprising at least one 2'-substituent group other than H or OH.

"3' target site" refers to the nucleotide of a target nucleic acid which is complementary to the 3'-most nucleotide of a particular compound.

"5' target site" refers to the nucleotide of a target nucleic acid which is complementary to the 5'-most nucleotide of a particular compound.

"5-methylcytosine" means a cytosine with a methyl group attached to the 5 position.

"About" means within ±10% of a value. For example, if it is stated, "the compounds affected about 70% inhibition of a MaTAR", it is implied that MaTAR levels are inhibited within a range of 60% and 80%.

"Administration" or "administering" refers to routes of introducing a compound or composition provided herein to an individual to perform its intended function. An example of a route of administration that can be used includes, but is not limited to parenteral administration, such as subcutaneous, intravenous, or intramuscular injection or infusion.

"Administered concomitantly" or "co-administration" means administration of two or more compounds in any manner in which the pharmacological effects of both are manifest in the patient. Concomitant administration does not require that both compounds be administered in a single pharmaceutical composition, in the same dosage form, by the same route of administration, or at the same time. The effects of both compounds need not manifest themselves at the same time. The effects need only be overlapping for a period of time and need not be coextensive. Concomitant administration or co-administration encompasses administration in parallel or sequentially.

"Amelioration" refers to an improvement or lessening of at least one indicator, sign, or symptom of an associated disease, disorder, or condition. In certain embodiments, amelioration includes a delay or slowing in the progression or severity of one or more indicators of a condition or disease. The progression or severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antisense activity" means any detectable and/or measurable activity attributable to the hybridization of an antisense compound to its target nucleic acid. In certain embodiments, antisense activity is a decrease in the amount or expression of a target nucleic acid or protein encoded by such target nucleic acid compared to target nucleic acid levels or target protein levels in the absence of the antisense compound to the target.

"Antisense compound" means a compound comprising an oligonucleotide and optionally one or more additional features, such as a conjugate group or terminal group. Examples of antisense compounds include single-stranded and double-stranded compounds, such as, oligonucleotides, ribozymes, siRNAs, shRNAs, ssRNAs, and occupancy-based compounds.

"Antisense inhibition" means reduction of target nucleic acid levels in the presence of an antisense compound complementary to a target nucleic acid compared to target nucleic acid levels in the absence of the antisense compound.

"Antisense mechanisms" are all those mechanisms involving hybridization of a compound with target nucleic acid, wherein the outcome or effect of the hybridization is either target degradation or target occupancy with concomitant stalling of the cellular machinery involving, for example, transcription or splicing.

"Antisense oligonucleotide" means an oligonucleotide having a nucleobase sequence that is complementary to a target nucleic acid or region or segment thereof. In certain embodiments, an antisense oligonucleotide is specifically hybridizable to a target nucleic acid or region or segment thereof.

"Bicyclic nucleoside" or "BNA" means a nucleoside comprising a bicyclic sugar moiety. "Bicyclic sugar" or "bicyclic sugar moiety" means a modified sugar moiety comprising two rings, wherein the second ring is formed via a bridge connecting two of the atoms in the first ring thereby forming a bicyclic structure. In certain embodiments, the first ring of the bicyclic sugar moiety is a furanosyl moiety. In certain embodiments, the bicyclic sugar moiety does not comprise a furanosyl moiety.

"Branching group" means a group of atoms having at least 3 positions that are capable of forming covalent linkages to at least 3 groups. In certain embodiments, a branching group provides a plurality of reactive sites for connecting tethered ligands to an oligonucleotide via a conjugate linker and/or a cleavable moiety.

"Cell-targeting moiety" means a conjugate group or portion of a conjugate group that is capable of binding to a particular cell type or particular cell types.

"cEt" or "constrained ethyl" means a bicyclic furanosyl sugar moiety comprising a bridge connecting the 4'-carbon and the 2'-carbon, wherein the bridge has the formula: 4'-CH(CH$_3$)—O-2'.

"Constrained ethyl nucleoside" (also cEt nucleoside) means a nucleoside comprising a cEt.

"Chemical modification" in a compound describes the substitutions or changes through chemical reaction, of any of the units in the compound. "Modified nucleoside" means a nucleoside having, independently, a modified sugar moiety and/or modified nucleobase. "Modified oligonucleotide" means an oligonucleotide comprising at least one modified internucleoside linkage, a modified sugar, and/or a modified nucleobase.

"Chemically distinct region" refers to a region of a compound that is in some way chemically different than another region of the same compound. For example, a region having 2'-O-methoxyethyl nucleotides is chemically distinct from a region having nucleotides without 2'-O-methoxyethyl modifications.

"Chimeric antisense compounds" means antisense compounds that have at least 2 chemically distinct regions, each position having a plurality of subunits.

"Cleavable bond" means any chemical bond capable of being split. In certain embodiments, a cleavable bond is selected from among: an amide, a polyamide, an ester, an ether, one or both esters of a phosphodiester, a phosphate ester, a carbamate, a di-sulfide, or a peptide.

"Cleavable moiety" means a bond or group of atoms that is cleaved under physiological conditions, for example, inside a cell, an animal, or a human.

"Complementary" in reference to an oligonucleotide means the nucleobase sequence of such oligonucleotide or one or more regions thereof matches the nucleobase sequence of another oligonucleotide or nucleic acid or one or more regions thereof when the two nucleobase sequences are aligned in opposing directions. Nucleobase matches or complementary nucleobases, as described herein, are limited to the following pairs: adenine (A) and thymine (T), adenine (A) and uracil (U), cytosine (C) and guanine (G), and 5-methyl cytosine ($^m$C) and guanine (G) unless otherwise specified. Complementary oligonucleotides and/or nucleic acids need not have nucleobase complementarity at each nucleoside and may include one or more nucleobase mismatches. By contrast, "fully complementary" or "100% complementary" in reference to oligonucleotides means that such oligonucleotides have nucleobase matches at each nucleoside without any nucleobase mismatches.

"Conjugate group" means a group of atoms that is attached to an oligonucleotide. Conjugate groups include a conjugate moiety and a conjugate linker that attaches the conjugate moiety to the oligonucleotide.

"Conjugate linker" means a group of atoms comprising at least one bond that connects a conjugate moiety to an oligonucleotide.

"Conjugate moiety" means a group of atoms that is attached to an oligonucleotide via a conjugate linker.

"Contiguous" in the context of an oligonucleotide refers to nucleosides, nucleobases, sugar moieties, or internucleoside linkages that are immediately adjacent to each other. For example, "contiguous nucleobases" means nucleobases that are immediately adjacent to each other in a sequence.

"Designing" or "Designed to" refer to the process of designing a compound that specifically hybridizes with a selected nucleic acid molecule.

"Diluent" means an ingredient in a composition that lacks pharmacological activity, but is pharmaceutically necessary or desirable. For example, the diluent in an injected composition can be a liquid, e.g. saline solution.

"Differently modified" mean chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

"Dose" means a specified quantity of a compound or pharmaceutical agent provided in a single administration, or in a specified time period. In certain embodiments, a dose may be administered in two or more boluses, tablets, or injections. For example, in certain embodiments, where subcutaneous administration is desired, the desired dose may require a volume not easily accommodated by a single injection. In such embodiments, two or more injections may be used to achieve the desired dose. In certain embodiments, a dose may be administered in two or more injections to minimize injection site reaction in an individual. In other embodiments, the compound or pharmaceutical agent is administered by infusion over an extended period of time or continuously. Doses may be stated as the amount of pharmaceutical agent per hour, day, week or month.

"Dosing regimen" is a combination of doses designed to achieve one or more desired effects.

"Double-stranded compound" means a compound comprising two oligomeric compounds that are complementary to each other and form a duplex, and wherein one of the two said oligomeric compounds comprises an oligonucleotide.

"Effective amount" means the amount of compound sufficient to effectuate a desired physiological outcome in an individual in need of the compound. The effective amount may vary among individuals depending on the health and physical condition of the individual to be treated, the taxonomic group of the individuals to be treated, the formulation of the composition, assessment of the individual's medical condition, and other relevant factors.

"Ensembl ID" is an identification number consisting of letters and numbers assigned to a gene sequence by Ensembl, which is a joint project between EMBL-EBI and the Wellcome Trust Sanger Institute to develop a software system that produces and maintains automatic annotation of selected eukaryotic genomes. Ensembl annotation helps identify a gene location in a particular genome and can be used to configure the equivalent gene on another species' genome.

"Expression" includes all the functions by which a gene's coded information is converted into structures present and operating in a cell. Such structures include, but are not limited to the products of transcription and translation.

"Gapmer" means an oligonucleotide comprising an internal region having a plurality of nucleosides that support RNase H cleavage positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings."

"Hybridization" means annealing of oligonucleotides and/or nucleic acids. While not limited to a particular mechanism, the most common mechanism of hybridization involves hydrogen bonding, which may be Watson-Crick, Hoogsteen or reversed Hoogsteen hydrogen bonding, between complementary nucleobases. In certain embodiments, complementary nucleic acid molecules include, but are not limited to, an antisense compound and a nucleic acid target. In certain embodiments, complementary nucleic acid molecules include, but are not limited to, an oligonucleotide and a nucleic acid target.

"Immediately adjacent" means there are no intervening elements between the immediately adjacent elements of the same kind (e.g. no intervening nucleobases between the immediately adjacent nucleobases).

"Individual" means a human or non-human animal selected for treatment or therapy.

"Inhibiting the expression or activity" refers to a reduction or blockade of the expression or activity relative to the expression of activity in an untreated or control sample and does not necessarily indicate a total elimination of expression or activity.

"Internucleoside linkage" means a group or bond that forms a covalent linkage between adjacent nucleosides in an oligonucleotide. "Modified internucleoside linkage" means any internucleoside linkage other than a naturally occurring, phosphate internucleoside linkage. Non-phosphate linkages are referred to herein as modified internucleoside linkages.

"Intravenous administration" means administration into a vein.

"Lengthened oligonucleotides" are those that have one or more additional nucleosides relative to an oligonucleotide disclosed herein, e.g. a parent oligonucleotide.

"lncRNA" means any long transcript that is not classified as protein-coding, including, but not limited to pseudogenes and antisense transcripts.

"Linked nucleosides" means adjacent nucleosides linked together by an internucleoside linkage.

"Linker-nucleoside" means a nucleoside that links an oligonucleotide to a conjugate moiety. Linker-nucleosides are located within the conjugate linker of a compound. Linker-nucleosides are not considered part of the oligonucleotide portion of a compound even if they are contiguous with the oligonucleotide.

"MaTAR" means Mammary Tumor Associated RNA and are potentially oncogenic lncRNAs that differentially expressed in breast cancer.

"MaTAR nucleic acid" means any nucleic acid encoding a MaTAR. For example, in certain embodiments, a MaTAR nucleic acid includes a DNA sequence encoding the MaTAR, an RNA sequence transcribed from DNA encoding the MaTAR (including genomic DNA comprising introns and exons), including a non-protein encoding (i.e. non-coding) RNA sequence. The target may be referred to in either upper or lower case.

"MaTAR-specific inhibitor" refers to any agent capable of specifically inhibiting the MaTAR expression or activity at the molecular level. For example, MaTAR-specific inhibitors include nucleic acids (including antisense compounds), peptides, antibodies, small molecules, and other agents capable of inhibiting the expression of the MaTAR.

"Mismatch" or "non-complementary" means a nucleobase of a first oligonucleotide that is not complementary to the corresponding nucleobase of a second oligonucleotide or target nucleic acid when the first and second oligonucleotides are aligned. For example, nucleobases including but not limited to a universal nucleobase, inosine, and hypoxanthine, are capable of hybridizing with at least one nucleobase but are still mismatched or non-complementary with respect to nucleobase to which it hybridized. As another example, a nucleobase of a first oligonucleotide that is not capable of hybridizing to the corresponding nucleobase of a second oligonucleotide or target nucleic acid when the first and second oligonucleotides are aligned is a mismatch or non-complementary nucleobase.

"Modulating" refers to changing or adjusting a feature in a cell, tissue, organ or organism. For example, modulating a MaTAR can mean to increase or decrease the level of the MaTAR in a cell, tissue, organ or organism. A "modulator" effects the change in the cell, tissue, organ or organism. For example, a compound can be a modulator of MaTAR that decreases the amount of MaTAR in a cell, tissue, organ or organism.

"MOE" means methoxyethyl.

"Monomer" refers to a single unit of an oligomer. Monomers include, but are not limited to, nucleosides and nucleotides.

"Motif" means the pattern of unmodified and/or modified sugar moieties, nucleobases, and/or internucleoside linkages, in an oligonucleotide.

"Natural" or "naturally occurring" means found in nature.

"Non-bicyclic modified sugar" or "non-bicyclic modified sugar moiety" means a modified sugar moiety that comprises a modification, such as a substituent, that does not form a bridge between two atoms of the sugar to form a second ring.

"Nucleic acid" refers to molecules composed of monomeric nucleotides. A nucleic acid includes, but is not limited to, ribonucleic acids (RNA), deoxyribonucleic acids (DNA), single-stranded nucleic acids, and double-stranded nucleic acids.

"Nucleobase" means a heterocyclic moiety capable of pairing with a base of another nucleic acid. As used herein a "naturally occurring nucleobase" is adenine (A), thymine (T), cytosine (C), uracil (U), and guanine (G). A "modified nucleobase" is a naturally occurring nucleobase that is chemically modified. A "universal base" or "universal nucleobase" is a nucleobase other than a naturally occurring nucleobase and modified nucleobase, and is capable of pairing with any nucleobase.

"Nucleobase sequence" means the order of contiguous nucleobases in a nucleic acid or oligonucleotide independent of any sugar or internucleoside linkage.

"Nucleoside" means a compound comprising a nucleobase and a sugar moiety. The nucleobase and sugar moiety are each, independently, unmodified or modified. "Modified nucleoside" means a nucleoside comprising a modified nucleobase and/or a modified sugar moiety. Modified nucleosides include abasic nucleosides, which lack a nucleobase.

"Nulliparous" is the medical term for a female who has never given birth to a viable, or live, baby.

"Oligomeric compound" means a compound comprising a single oligonucleotide and optionally one or more additional features, such as a conjugate group or terminal group.

"Oligonucleotide" means a polymer of linked nucleosides each of which can be modified or unmodified, independent one from another. Unless otherwise indicated, oligonucleotides consist of 8-80 linked nucleosides. "Modified oligonucleotide" means an oligonucleotide, wherein at least one sugar, nucleobase, or internucleoside linkage is modified. "Unmodified oligonucleotide" means an oligonucleotide that does not comprise any sugar, nucleobase, or internucleoside modification.

"Parent oligonucleotide" means an oligonucleotide whose sequence is used as the basis of design for more oligonucleotides of similar sequence but with different lengths, motifs, and/or chemistries. The newly designed oligonucleotides may have the same or overlapping sequence as the parent oligonucleotide.

"Parenteral administration" means administration through injection or infusion. Parenteral administration includes subcutaneous administration, intravenous administration, intramuscular administration, intraarterial administration, intraperitoneal administration, or intracranial administration, e.g. intrathecal or intracerebroventricular administration.

"Pharmaceutically acceptable carrier or diluent" means any substance suitable for use in administering to an animal. For example, a pharmaceutically acceptable carrier can be a sterile aqueous solution, such as PBS or water-for-injection.

"Pharmaceutically acceptable salts" means physiologically and pharmaceutically acceptable salts of compounds, such as oligomeric compounds or oligonucleotides, i.e., salts that retain the desired biological activity of the parent compound and do not impart undesired toxicological effects thereto.

"Pharmaceutical agent" means a compound that provides a therapeutic benefit when administered to an individual.

"Pharmaceutical composition" means a mixture of substances suitable for administering to an individual. For example, a pharmaceutical composition may comprise one or more compounds or salt thereof and a sterile aqueous solution.

"Phosphorothioate linkage" means a modified phosphate linkage in which one of the non-bridging oxygen atoms is replaced with a sulfur atom. A phosphorothioate internucleoside linkage is a modified internucleoside linkage.

"Phosphorus moiety" means a group of atoms comprising a phosphorus atom. In certain embodiments, a phosphorus moiety comprises a mono-, di-, or tri-phosphate, or phosphorothioate.

"Portion" means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an oligomeric compound.

"Prevent" refers to delaying or forestalling the onset, development or progression of a disease, disorder, or condition for a period of time from minutes to indefinitely.

"Prodrug" means a compound in a form outside the body which, when administered to an individual, is metabolized to another form within the body or cells thereof. In certain embodiments, the metabolized form is the active, or more active, form of the compound (e.g., drug). Typically conversion of a prodrug within the body is facilitated by the action of an enzyme(s) (e.g., endogenous or viral enzyme) or chemical(s) present in cells or tissues, and/or by physiologic conditions.

"Reduce" means to bring down to a smaller extent, size, amount, or number.

"RefSeq No." is a unique combination of letters and numbers assigned to a sequence to indicate the sequence is for a particular target transcript (e.g., target gene). Such sequence and information about the target gene (collectively, the gene record) can be found in a genetic sequence database. Genetic sequence databases include the NCBI Reference Sequence database, GenBank, the European Nucleotide Archive, and the DNA Data Bank of Japan (the latter three forming the International Nucleotide Sequence Database Collaboration or INSDC).

"Region" is defined as a portion of the target nucleic acid having at least one identifiable structure, function, or characteristic.

"RNAi compound" means an antisense compound that acts, at least in part, through RISC or Ago2, but not through RNase H, to modulate a target nucleic acid and/or protein encoded by a target nucleic acid. RNAi compounds include, but are not limited to double-stranded siRNA, single-stranded RNA (ssRNA), and microRNA, including microRNA mimics.

"Segments" are defined as smaller or sub-portions of regions within a nucleic acid.

"Side effects" means physiological disease and/or conditions attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum may indicate liver toxicity or liver function abnormality. For example, increased bilirubin may indicate liver toxicity or liver function abnormality.

"Single-stranded" in reference to a compound means the compound has only one oligonucleotide.

"Self-complementary" means an oligonucleotide that at least partially hybridizes to itself. A compound consisting of one oligonucleotide, wherein the oligonucleotide of the compound is self-complementary, is a single-stranded compound. A single-stranded compound may be capable of binding to a complementary compound to form a duplex.

"Sites," are defined as unique nucleobase positions within a target nucleic acid.

"Specifically hybridizable" refers to an oligonucleotide having a sufficient degree of complementarity between the oligonucleotide and a target nucleic acid to induce a desired effect, while exhibiting minimal or no effects on non-target nucleic acids. In certain embodiments, specific hybridization occurs under physiological conditions.

"Specifically inhibit" a target nucleic acid means to reduce or block expression of the target nucleic acid while exhibiting fewer, minimal, or no effects on non-target nucleic acids reduction and does not necessarily indicate a total elimination of the target nucleic acid's expression.

"Standard cell assay" means assay(s) described in the Examples and reasonable variations thereof "Standard in vivo experiment" means the procedure(s) described in the Example(s) and reasonable variations thereof.

"Sugar moiety" means an unmodified sugar moiety or a modified sugar moiety. "Unmodified sugar moiety" or "unmodified sugar" means a 2'-OH(H) furanosyl moiety, as found in RNA (an "unmodified RNA sugar moiety"), or a 2'-H(H) moiety, as found in DNA (an "unmodified DNA sugar moiety"). Unmodified sugar moieties have one hydrogen at each of the 1', 3', and 4' positions, an oxygen at the 3' position, and two hydrogens at the 5' position. "Modified sugar moiety" or "modified sugar" means a modified furanosyl sugar moiety or a sugar surrogate. "Modified furanosyl sugar moiety" means a furanosyl sugar comprising a non-hydrogen substituent in place of at least one hydrogen of an unmodified sugar moiety. In certain embodiments, a modified furanosyl sugar moiety is a 2'-substituted sugar moiety. Such modified furanosyl sugar moieties include bicyclic sugars and non-bicyclic sugars.

"Sugar surrogate" means a modified sugar moiety having other than a furanosyl moiety that can link a nucleobase to another group, such as an internucleoside linkage, conjugate group, or terminal group in an oligonucleotide. Modified nucleosides comprising sugar surrogates can be incorporated into one or more positions within an oligonucleotide and such oligonucleotides are capable of hybridizing to complementary oligomeric compounds or nucleic acids.

"Subcutaneous administration" means administration just below the skin.

"Target gene" refers to a gene encoding a target.

"Targeting" means specific hybridization of a compound that to a target nucleic acid in order to induce a desired effect.

"Target nucleic acid," "target RNA," "target RNA transcript" and "nucleic acid target" all mean a nucleic acid capable of being targeted by compounds described herein.

"Target region" means a portion of a target nucleic acid to which one or more compounds is targeted.

"Target segment" means the sequence of nucleotides of a target nucleic acid to which a compound described herein is targeted. "5' target site" refers to the 5'-most nucleotide of a target segment. "3' target site" refers to the 3'-most nucleotide of a target segment.

"Terminal group" means a chemical group or group of atoms that is covalently linked to a terminus of an oligonucleotide.

"Therapeutically effective amount" means an amount of a compound, pharmaceutical agent, or composition that provides a therapeutic benefit to an individual.

"Treat" refers to administering a compound or pharmaceutical composition to an animal in order to effect an alteration or improvement of a disease, disorder, or condition in the animal.

Certain Embodiments

Certain embodiments provide methods, compounds, and compositions for modulating a breast cancer condition, or a symptom thereof, in an animal by administering a therapeutically effective amount of the compound or composition to the animal, wherein the compound or composition comprises a MaTAR modulator. Modulation of a MaTAR can lead to a decrease of the MaTAR level or expression in order to treat, prevent, ameliorate or delay breast cancer, or a symptom thereof. In certain embodiments, the MaTAR modulator is a MaTAR-specific inhibitor. In certain embodiments, MaTAR-specific inhibitors are nucleic acids (including antisense compounds), peptides, antibodies, small molecules, and other agents capable of inhibiting the expression of the MaTAR.

In certain embodiments disclosed herein, each MaTAR has the sequences recited in the Tables of the specification disclosed herein. In certain embodiments disclosed herein, each MaTAR has the human sequence recited in SEQ ID Nos: 1-111 and SEQ ID Nos: 193-280.

Certain embodiments disclosed herein provide compounds or compositions comprising a MaTAR modulator. In certain embodiments, the MaTAR modulator is a MaTAR-specific inhibitor. In certain embodiments, the MaTAR-specific inhibitor is a nucleic acid, polypeptide, antibody, small molecules, or other agent capable of inhibiting the expression of a MaTAR. In certain embodiments, the nucleic acid is a compound or composition targeting a MaTAR. In certain embodiments, the compound or composition is single stranded. In certain embodiments, the compound or composition is double stranded. In certain embodiments, the compound or composition targeting a MaTAR comprises an oligonucleotide. In certain embodiments, the oligonucleotide is single stranded. In certain embodiments, the compound comprises deoxyribonucleotides. In certain embodiments, the compound is double-stranded and comprises ribonucleotides. In certain embodiments, the oligonucleotide is a modified oligonucleotide. In certain embodiments, the modified oligonucleotide is single stranded. In any of the foregoing embodiments, the compound can be an antisense compound or oligomeric compound.

In any of the foregoing embodiments, the compound can consist of 8 to 80, 10 to 30, 12 to 50, 13 to 30, 13 to 50, 14 to 30, 14 to 50, 15 to 30, 15 to 50, 16 to 30, 16 to 50, 17 to 30, 17 to 50, 18 to 22, 18 to 24, 18 to 30, 18 to 50, 19 to 22, 19 to 30, 19 to 50, or 20 to 30 linked nucleosides. In certain embodiments, these compounds are oligonucleotides.

Certain embodiments disclosed herein provide a compound or composition comprising a modified oligonucleotide that is 10 to 30 linked nucleosides in length targeted to a MaTAR. The MaTAR target can have a nucleobase sequence selected from any one of SEQ ID NOs: 1-111 and SEQ ID Nos: 193-280. In certain embodiments, the nucleobase sequence of the modified oligonucleotide is at least 70%, 75%, 80%, 85%, 90%, 95% or 100% complementary to the nucleobase sequences recited in any one of SEQ ID NOs: 1-111 and SEQ ID Nos: 193-280 as measured over the entirety of the modified oligonucleotide. In certain embodiments, the modified oligonucleotide comprises a nucleobase sequence comprising a portion of at least 8, at least 9, at least 10, at least 11, at least 12, at least 13, at least 14, at least 15, or 16 contiguous nucleobases complementary to an equal length portion of SEQ ID NO: 1-111 and SEQ ID Nos: 193-280.

Certain embodiments provide a compound comprising a modified oligonucleotide 8 to 80 linked nucleosides in length and having a nucleobase sequence comprising the nucleobase sequence of any one of SEQ ID NOs: 112-156 and SEQ ID Nos: 169-192. In certain embodiments, the compound is an antisense compound or oligomeric compound. In certain embodiments, the compound is single-stranded. In certain embodiments, the compound is double-stranded. In certain embodiments, the modified oligonucleotide consists of 12 to 30 linked nucleosides.

Certain embodiments provide a compound comprising a modified oligonucleotide consisting of the nucleobase sequence of any one of SEQ ID NOs: 112-156 and SEQ ID Nos: 169-192. In certain embodiments, the compound is an antisense compound or oligomeric compound. In certain embodiments, the compound is single-stranded. In certain embodiments, the compound is double-stranded.

In certain embodiments, the modified oligonucleotide consists of 10 to 50, 10 to 30, 12 to 30, 13 to 24, 14 to 24, 15 to 30, 15 to 24, 15 to 20, 15 to 18, 16 to 30, 16 to 24, 16 to 20, 16 to 18, 18 to 24 or 19 to 22 linked nucleosides. In certain embodiments, the modified oligonucleotide consists of 8, 9, 10, 11, 12, 13, 14, 15, 16, 17, 18, 19, 20, 21, 22, 23, 24, 25, 26, 27, 28, 29 or 30 linked nucleosides or a range defined by any two of these values.

In certain embodiments, at least one internucleoside linkage of said modified oligonucleotide is a modified internucleoside linkage. In certain embodiments, each internucleoside linkage is a phosphorothioate internucleoside linkage.

In certain embodiments, any of the foregoing oligonucleotides comprises at least one modified sugar. In certain embodiments, at least one modified sugar comprises a 2'-O-methoxyethyl group. In certain embodiments, at least one modified sugar is a bicyclic sugar, such as a 4'-CH(CH$_3$)—O-2' group, a 4'-CH$_2$—O-2' group, or a 4'-(CH$_2$)$_2$—O-2' group.

In certain embodiments, at least one nucleoside of said modified oligonucleotide comprises a modified nucleobase. In certain embodiments, the modified nucleobase is a 5-methylcytosine.

Certain embodiments disclosed herein provide a compound or composition comprising a modified oligonucleotide with: a) a gap segment consisting of linked deoxynucleosides; b) a 5' wing segment consisting of linked nucleosides; and c) a 3' wing segment consisting of linked nucleosides. The gap segment is positioned between the 5' wing segment and the 3' wing segment and each nucleoside of each wing segment comprises a modified sugar. In certain embodiments, at least one internucleoside linkage is a phosphorothioate linkage. In certain embodiments, and at least one cytosine is a 5-methylcytosine.

Certain embodiments disclosed herein provide a method of reducing a MaTAR expression in an animal comprising administering to the animal a compound or composition comprising a MaTAR-specific inhibitor. In certain embodiments, the MaTAR-specific inhibitor is a nucleic acid, peptide, antibody, small molecule or other agent capable of inhibiting the expression of the MaTAR. In certain embodiments, the MaTAR-specific inhibitor comprises a compound described herein. In certain embodiments, the compound comprises an antisense compound or an oligomeric compound. In certain embodiments, the compound comprises a modified oligonucleotide. In certain embodiments, the compound or composition comprises a modified oligonucleotide 8 to 80 linked nucleosides in length and having a nucleobase sequence comprising at least an 8, 9, 10, 11, 12, 13, 14, 15, or 16 contiguous nucleobase portion of any one of SEQ ID NOs: 112-156 and SEQ ID Nos: 169-192. In certain embodiments, the modified oligonucleotide consists of 10 to 30 linked nucleosides. In certain embodiments disclosed herein, the MaTAR has the human sequence recited in SEQ ID Nos: 1-111 and SEQ ID Nos: 193-280.

In certain embodiments, the compounds or compositions disclosed herein further comprise a conjugate group. In certain embodiments, the conjugate group is a carbohydrate group. In certain embodiments, the conjugate group is a GalNAc group.

In certain embodiments, the compounds or compositions disclosed herein comprise a salt of the compound. In certain embodiments, the compounds or compositions disclosed herein comprise a salt of the modified oligonucleotide. In certain embodiments, the salt is a sodium salt. In certain embodiments, the salt is a potassium salt.

In certain embodiments, the compounds or compositions disclosed herein further comprise a pharmaceutically acceptable carrier or diluent.

Certain embodiments disclosed herein provide a method of treating, preventing, delaying or ameliorating breast cancer in an animal comprising administering to the animal a compound or composition comprising a MaTAR-specific inhibitor. In certain embodiments, the MaTAR-specific inhibitor is a nucleic acid, peptide, antibody, small molecule or other agent capable of inhibiting the expression of the MaTAR. In certain embodiments, the MaTAR-specific inhibitor comprises a compound described herein. In certain embodiments, the compound comprises an antisense compound or an oligomeric compound. In certain embodiments, the compound comprises a modified oligonucleotide In certain embodiments, the compound or composition comprises a modified oligonucleotide 8 to 80 linked nucleosides in length and having a nucleobase sequence comprising at least an 8, 9, 10, 11, 12, 13, 14, 15, or 16 contiguous nucleobase portion of any one of SEQ ID NOs: 112-156 and SEQ ID Nos: 169-192. In certain embodiments disclosed herein, the MaTAR has the human sequence recited in SEQ ID Nos: 1-111 and SEQ ID Nos: 193-280. In certain embodiments, the modified oligonucleotide consists of 10 to 30 linked nucleosides.

Certain embodiments disclosed herein provide a method of treating an animal at risk for breast cancer comprising administering to the animal a compound or composition comprising a MaTAR-specific inhibitor. In certain embodiments, the MaTAR-specific inhibitor is a nucleic acid, peptide, antibody, small molecule or other agent capable of inhibiting the expression of the MaTAR. In certain embodiments, the MaTAR-specific inhibitor comprises a compound. In certain embodiments, the compound comprises an antisense compound or an oligomeric compound. In certain embodiments, the compound comprises a modified oligonucleotide. In certain embodiments, the compound or composition comprises a modified oligonucleotide 8 to 80 linked nucleosides in length and having a nucleobase sequence comprising at least an 8, 9, 10, 11, 12, 13, 14, 15, or 16 contiguous nucleobase portion of any one of SEQ ID NOs: 112-156 and SEQ ID Nos: 169-192. In certain embodiments, the modified oligonucleotide consists of 10 to 30 linked nucleosides. In certain embodiments disclosed herein, the MaTAR has the human sequence recited in SEQ ID Nos: 1-111 and SEQ ID Nos: 193-280.

Certain embodiments disclosed herein provide a method of reducing tumor progression in an animal with breast cancer comprising administering to the animal a compound or composition comprising a MaTAR-specific inhibitor. In certain embodiments, the MaTAR-specific inhibitor is a nucleic acid, peptide, antibody, small molecule or other agent capable of inhibiting the expression of the MaTAR. In certain embodiments, the MaTAR-specific inhibitor comprises a compound described herein. In certain embodiments, the MaTAR-specific inhibitor comprises an antisense compound or an oligomeric compound. In certain embodiments, the compound comprises a modified oligonucleotide. In certain embodiments, the compound or composition comprises a modified oligonucleotide 8 to 80 linked nucleosides in length and having a nucleobase sequence comprising at least an 8, 9, 10, 11, 12, 13, 14, 15, or 16 contiguous nucleobase portion of any one of SEQ ID NOs: 112-156 and SEQ ID Nos: 169-192. In certain embodiments, the modified oligonucleotide consists of 10 to 30 linked nucleosides. In certain embodiments disclosed herein, the MaTAR has the human sequence recited in SEQ ID Nos: 1-111 and SEQ ID Nos: 193-280.

Certain embodiments disclosed herein provide a method of reducing metastasis in an animal with breast cancer comprising administering to the animal a compound or composition comprising a MaTAR-specific inhibitor. In certain embodiments, the MaTAR-specific inhibitor is a nucleic acid, peptide, antibody, small molecule or other agent capable of inhibiting the expression of the MaTAR. In certain embodiments, the MaTAR-specific inhibitor comprises a compound described herein. In certain embodiments, the MaTAR-specific inhibitor comprises an antisense compound or an oligomeric compound. In certain embodiments, the compound comprises a modified oligonucleotide. In certain embodiments, the compound or composition comprises a modified oligonucleotide 8 to 80 linked nucleosides in length and having a nucleobase sequence comprising at least an 8, 9, 10, 11, 12, 13, 14, 15, or 16 contiguous nucleobase portion of any one of SEQ ID NOs: 112-156 and SEQ ID Nos: 169-192. In certain embodiments, the modified oligonucleotide consists of 10 to 30 linked nucleosides. In certain embodiments disclosed herein, the MaTAR has the human sequence recited in SEQ ID Nos: 1-111 and SEQ ID Nos: 193-280.

Certain embodiments disclosed herein provide a method of reducing cell proliferation in an animal with breast cancer comprising administering to the animal a compound or composition comprising a MaTAR-specific inhibitor. In certain embodiments, the MaTAR-specific inhibitor is a nucleic acid, peptide, antibody, small molecule or other agent capable of inhibiting the expression of a MaTAR In certain embodiments, the MaTAR-specific inhibitor comprises a compound described herein. In certain embodiments, the MaTAR-specific inhibitor comprises an antisense compound or an oligomeric compound. In certain embodiments, the compound comprises a modified oligonucleotide. In certain embodiments, the compound or composition comprises a modified oligonucleotide 8 to 80 linked nucleosides in length and having a nucleobase sequence comprising at least an 8, 9, 10, 11, 12, 13, 14, 15, or 16 contiguous nucleobase portion of any one of SEQ ID NOs: 112-156 and SEQ ID Nos: 169-192. In certain embodiments, the modified oligonucleotide consists of 10 to 30 linked nucleosides. In certain embodiments disclosed herein, the MaTAR has the human sequence recited in SEQ ID Nos: 1-111 and SEQ ID Nos: 193-280.

Certain embodiments disclosed herein provide a method of reducing tumor cell invasion in an animal with breast cancer comprising administering to the animal a compound or composition comprising a MaTAR-specific inhibitor. In certain embodiments, the MaTAR-specific inhibitor is a nucleic acid, peptide, antibody, small molecule or other agent capable of inhibiting the expression of a MaTAR. In certain embodiments, the MaTAR-specific inhibitor comprises a compound described herein. In certain embodiments, the MaTAR-specific inhibitor comprises an antisense compound or an oligomeric compound. In certain embodiments, the compound comprises a modified oligonucleotide. In certain embodiments, the compound or composition comprises a modified oligonucleotide 8 to 80 linked nucleosides in length and having a nucleobase sequence comprising at least an 8, 9, 10, 11, 12, 13, 14, 15, or 16 contiguous nucleobase portion of any one of SEQ ID NOs: 112-156 and SEQ ID Nos: 169-192. In certain embodiments, the modified oligonucleotide consists of 10 to 30 linked nucleosides. In certain embodiments disclosed herein, the MaTAR has the human sequence recited in SEQ ID Nos: 1-111 and SEQ ID Nos: 193-280.

Certain embodiments disclosed herein provide a method of reducing collective cell migration in an animal with breast cancer comprising administering to the animal a compound or composition comprising a MaTAR-specific inhibitor. In certain embodiments, the MaTAR-specific inhibitor is a nucleic acid, peptide, antibody, small molecule or other agent capable of inhibiting the expression of the MaTAR. In certain embodiments, the MaTAR-specific inhibitor comprises a compound described herein. In certain embodiments, the MaTAR-specific inhibitor comprises an antisense compound or an oligomeric compound. In certain embodiments, the compound comprises a modified oligonucleotide. In certain embodiments, the compound or composition comprises a modified oligonucleotide 8 to 80 linked nucleosides in length and having a nucleobase sequence comprising at least an 8, 9, 10, 11, 12, 13, 14, 15, or 16 contiguous nucleobase portion of any one of SEQ ID NOs: 112-156 and SEQ ID Nos: 169-192. In certain embodiments, the modified oligonucleotide consists of 10 to 30 linked nucleosides. In certain embodiments disclosed herein, the MaTAR has the human sequence recited in SEQ ID Nos: 1-111 and SEQ ID Nos: 193-280.

Certain embodiments disclosed herein provide a method of ameliorating breast cancer in an animal comprising administering to the animal a therapeutically effective amount of a compound or composition comprising a MaTAR-specific inhibitor. In certain embodiments, the breast cancer is luminal B breast cancer. In certain embodiments, the breast cancer is HER2/neu-amplified breast cancer. In certain embodiments, the MaTAR-specific inhibitor is a nucleic acid, peptide, antibody, small molecule or other agent capable of inhibiting the expression of the MaTAR. In certain embodiments, the MaTAR-specific inhibitor comprises a compound described herein. In certain embodiments, the MaTAR-specific inhibitor comprises an antisense compound or an oligomeric compound. In certain embodiments, the compound comprises a modified oligonucleotide. In certain embodiments, the therapeutically effective amount of the compound or composition administered to the animal ameliorates breast cancer in the animal. In certain embodiments, the compound or composition comprises a modified oligonucleotide 8 to 80 linked nucleosides in length and having a nucleobase sequence comprising at least an 8, 9, 10, 11, 12, 13, 14, 15, or 16 contiguous nucleobase portion of any one of SEQ ID NOs: 112-156 and SEQ ID Nos: 169-192. In certain embodiments, the modified oligonucleotide consists of 10 to 30 linked nucleosides. In certain embodiments disclosed herein, the MaTAR has the human sequence recited in SEQ ID Nos: 1-111 and SEQ ID Nos: 193-280.

Certain embodiments disclosed herein provide a method for treating an animal at risk for breast cancer comprising administering to said animal a therapeutically effective amount of a compound or composition comprising a MaTAR-specific inhibitor. In certain embodiments, the breast cancer is luminal B breast cancer. In certain embodiments, the breast cancer is HER2/neu-amplified breast cancer. In certain embodiments, the MaTAR-specific inhibitor is a nucleic acid, peptide, antibody, small molecule or other agent capable of inhibiting the expression of the MaTAR. In certain embodiments, the MaTAR-specific inhibitor comprises a compound described herein. In certain embodiments, the MaTAR-specific inhibitor comprises an antisense compound or an oligomeric compound. In certain embodiments, the compound comprises a modified oligonucleotide. In certain embodiments, the therapeutically effective amount of the compound or composition administered to the animal reduces the risk of breast cancer in the animal. In certain embodiments, the compound or composition comprises a modified oligonucleotide 8 to 80 linked nucleosides in length and having a nucleobase sequence comprising at least an 8, 9, 10, 11, 12, 13, 14, 15, or 16 contiguous nucleobase portion of any one of SEQ ID NOs: 112-156 and SEQ ID Nos: 169-192. In certain embodiments, the modified oligonucleotide consists of 10 to 30 linked nucleosides. In certain embodiments disclosed herein, the MaTAR has the human sequence recited in SEQ ID Nos: 1-111 and SEQ ID Nos: 193-280.

Certain embodiments disclosed herein provide a method of differentiating a primary breast tumor in an animal comprising administering to the animal a therapeutically effective amount of a compound comprising a MaTAR-specific inhibitor. In certain embodiments, differentiation is specific to breast tumor tissue and not in normal mammary gland tissue. In certain embodiments, the MaTAR is expressed in breast tumors and not in normal mammary gland tissue. In certain embodiments, the breast tumor is luminal B breast cancer. In certain embodiments, the breast tumor is HER2/neu-amplified breast cancer. In certain embodiments, the MaTAR-specific inhibitor is a nucleic acid, peptide, antibody, small molecule or other agent capable of inhibiting the expression of the MaTAR. In certain embodiments, the MaTAR-specific inhibitor comprises a compound described herein. In certain embodiments, the MaTAR-specific inhibitor comprises an antisense compound or an oligomeric compound. In certain embodiments, the compound comprises a modified oligonucleotide. In certain embodiments, the therapeutically effective amount of the compound or composition administered to the animal results in differentiation of the primary breast tumor in the animal. In certain embodiments, the compound or composition comprises a modified oligonucleotide 8 to 80 linked nucleosides in length and having a nucleobase sequence comprising at least an 8, 9, 10, 11, 12, 13, 14, 15, or 16 contiguous nucleobase portion of any one of SEQ ID NOs: 112-156 and SEQ ID Nos: 169-192. In certain embodiments, the modified oligonucleotide consists of 10 to 30 linked nucleosides. In certain embodiments disclosed herein, the MaTAR has the human sequence recited in SEQ ID Nos: 1-111 and SEQ ID Nos: 193-280.

Certain embodiments disclosed herein provide a method of modulating the gene expression pattern of a breast tumor in an animal comprising administering to the animal a therapeutically effective amount of a compound comprising a MaTAR-specific inhibitor to the animal. In certain embodiments, gene expression modulation is specific to breast tumor tissue and not in normal mammary gland tissue. In certain embodiments, the MaTAR is expressed in breast tumors and not in normal mammary gland tissue. In certain embodiments, the breast tumor is luminal B breast cancer. In certain embodiments, the breast tumor is HER2/neu-amplified breast cancer. In certain embodiments, the MaTAR-specific inhibitor is a nucleic acid, peptide, antibody, small molecule or other agent capable of inhibiting the expression of the MaTAR. In certain embodiments, the MaTAR-specific inhibitor comprises a compound described herein. In certain embodiments, the MaTAR-specific inhibitor comprises an antisense compound or an oligomeric compound. In certain embodiments, the compound comprises a modified oligonucleotide. In certain embodiments, the therapeutically effective amount of the compound or composition administered to the animal results in modulation of the gene expression of the primary breast tumor in the animal. In certain embodiments, the compound or composition comprises a modified oligonucleotide 8 to 80 linked nucleosides in length and having a nucleobase sequence comprising at least an 8, 9, 10, 11, 12, 13, 14, 15, or 16 contiguous nucleobase portion of any one of SEQ ID NOs: 112-156 and SEQ ID Nos: 169-192. In certain embodiments, the modified oligonucleotide consists of 10 to 30 linked nucleosides. In certain embodiments disclosed herein, the MaTAR has the human sequence recited in SEQ ID Nos: 1-111 and SEQ ID Nos: 193-280.

In certain embodiments, the breast tumor or cancer is luminal B or HER2/neu-amplified subtypes of human breast cancer.

In certain embodiments, administering the compound or composition disclosed herein reduces the levels of tumor progression, metastasis, cell proliferation, tumor cell invasion, or collective cell migration, or a combination thereof. In certain embodiments, tumor cell invasion was independently reduced by at least 5%, at least 10%, at least 20%, at least 30%, at least 35%, at least 40%, at least 45% or at least 50%. In certain embodiments, tumor organoid branching was independently reduced by at least 5%, at least 10%, at least 20%, at least 30%, at least 35%, at least 40%, at least 45% or at least 50%. In certain embodiments, tumor cell viability was reduced by at least 5%, at least 10%, at least 20%, at least 30%, at least 35%, at least 40%, at least 45% or at least 50%.

Certain embodiments provide uses of the compounds and compositions described herein for inhibiting a MaTAR expression. In certain embodiments, the compounds or compositions inhibit a MaTAR by at least 5%, at least 10%, at least 20%, at least 30%, at least 35%, at least 40%, at least 45%, at least 50%, at least 55%, at least 60%, at least 65%, at least 70%, at least 75%, at least 80%, at least 85%, or at least 90%.

Certain embodiments provide uses of the compounds and compositions described herein for use in therapy. In certain embodiments, the therapy is used in treating, preventing, delaying the onset or slowing progression of a disease related to elevated expression of a MaTAR. In certain embodiments, the disease is breast cancer. In certain embodiments, the breast cancer is luminal B breast cancer. In certain embodiments, the breast cancer is HER2/neu-amplified breast cancer. In certain embodiments, the compound or composition comprises a modified oligonucleotide 8 to 80 linked nucleosides in length and having a nucleobase sequence comprising at least an 8, 9, 10, 11, 12, 13, 14, 15, or 16 contiguous nucleobase portion of any one of SEQ ID NOs: 112-156 and SEQ ID Nos: 169-192. In certain embodiments, the modified oligonucleotide consists of 10 to 30 linked nucleosides. In certain embodiments disclosed herein, the MaTAR has the human sequence recited in SEQ ID Nos: 1-111 and SEQ ID Nos: 193-280.

In certain embodiments, the animal is a human.

In certain embodiments, administration comprises parenteral administration. In certain embodiments, parenteral administration comprises subcutaneous administration. In certain embodiments, parenteral administration comprises intravenous administration.

In certain embodiments, the compounds or compositions disclosed herein are designated as a first agent and the methods or uses disclosed herein further comprise administering a second agent. In certain embodiments, the first agent and the second agent are co-administered. In certain embodiments the first agent and the second agent are co-administered sequentially or concomitantly.

In certain embodiments, use of a compound or composition disclosed herein results in tumor cell invasion independently reduced by at least 5%, at least 10%, at least 20%, at least 30%, at least 35%, at least 40%, at least 45% or at least 50%. In certain embodiments, use of a compound or composition disclosed herein results in tumor organoid branching independently reduced by at least 5%, at least 10%, at least 20%, at least 30%, at least 35%, at least 40%, at least 45% or at least 50%. In certain embodiments, use of a compound or composition disclosed herein results in tumor cell viability reduced by at least 5%, at least 10%, at least 20%, at least 30%, at least 35%, at least 40%, at least 45% or at least 50%.

Certain embodiments provide the use of a compound or composition as described herein in the manufacture of a medicament for treating, ameliorating, delaying or preventing one or more diseases, disorders, conditions, symptoms or physiological markers associated with a MaTAR. In certain embodiments, the compound or composition as described herein is used in the manufacture of a medicament for treating, ameliorating, delaying or preventing breast cancer, or a symptom or physiological marker thereof. In certain embodiments, the breast cancer is luminal B breast cancer. In certain embodiments, the breast cancer is HER2/neu-amplified breast cancer. In certain embodiments, the compound or composition comprises a modified oligonucleotide 8 to 80 linked nucleosides in length and having a nucleobase sequence comprising at least an 8, 9, 10, 11, 12, 13, 14, 15, or 16 contiguous nucleobase portion of any one of SEQ ID NOs: 112-156 and SEQ ID Nos: 169-192. In certain embodiments, the modified oligonucleotide consists of 10 to 30 linked nucleosides. In certain embodiments disclosed herein, the MaTAR has the human sequence recited in SEQ ID Nos: 1-111 and SEQ ID Nos: 193-280.

Certain Indications

Certain embodiments provided herein relate to methods of inhibiting a MaTAR expression, which can be useful for treating, preventing, or ameliorating a disease associated with a MaTAR in an individual, by administration of a compound that targets a MaTAR. In certain embodiments, such a compound is a MaTAR-specific inhibitor. In certain embodiments, the compound is an antisense compound or an oligomeric compound targeted to a MaTAR. In certain embodiments, the compound comprises a modified oligonucleotide targeted to a MaTAR.

In certain embodiments disclosed herein, MaTARs have the human and murine coordinates and sequences as set forth in the Tables in this specification and also as recited in SEQ ID Nos: 1-111 and SEQ ID Nos: 193-280.

Examples of diseases associated with a MaTAR treatable, preventable, and/or ameliorable with the methods provided herein include breast cancer. In certain embodiments, the breast cancer is luminal B breast cancer. In certain embodiments, the breast cancer is HER2/neu-amplified breast cancer.

In certain embodiments, a method of treating, preventing, or ameliorating a disease associated with a breast cancer in an individual comprises administering to the individual a MaTAR-specific inhibitor of a MaTAR, thereby treating, preventing, or ameliorating the disease. In certain embodiments, the MaTAR-specific inhibitor is a compound targeted to a MaTAR, such as an oligonucleotide targeted to a MaTAR. In certain embodiments, the MaTAR-specific inhibitor is a compound comprising a modified oligonucleotide consisting of 8 to 80 linked nucleosides and having a nucleobase sequence complementary to any of the nucleobase sequences of SEQ ID NOs: 1-111 and SEQ ID Nos: 193-280. In any of the foregoing embodiments, the compound can be single-stranded. In any of the foregoing embodiments, the compound can be an antisense compound or oligomeric compound. In certain embodiments, the compound is administered to the individual parenterally. In certain embodiments, administering the compound improves, preserves, or prevents breast cancer. In certain embodiments, the compound or composition comprises a modified oligonucleotide 8 to 80 linked nucleosides in length and having a nucleobase sequence comprising at least an 8, 9, 10, 11, 12, 13, 14, 15, or 16 contiguous nucleobase portion of any one of SEQ ID NOs: 112-156 and SEQ ID Nos: 169-192. In certain embodiments, the modified oligonucleotide consists of 10 to 30 linked nucleosides.

In certain embodiments, a method of treating, preventing, or ameliorating tumor progression, metastasis, cell proliferation, tumor cell invasion, or collective migration comprises administering to the individual a MaTAR-specific inhibitor, thereby treating, preventing, or ameliorating tumor progression, metastasis, cell proliferation, tumor cell invasion, or collective migration. In certain embodiments, the MaTAR-specific inhibitor is a compound targeted to a MaTAR, such as an oligonucleotide targeted to a MaTAR. In certain embodiments, the MaTAR-specific inhibitor is a compound comprising a modified oligonucleotide consisting of 8 to 80 linked nucleosides and having a nucleobase sequence complementary to any of the nucleobase sequences of SEQ ID NOs: 1-111 and SEQ ID Nos: 193-280. In any of the foregoing embodiments, the compound can be single-stranded. In any of the foregoing embodiments, the compound can be an antisense compound or oligomeric compound. In certain embodiments, the compound is administered to the individual parenterally. In certain embodiments, administering the compound improves, preserves, or prevents tumor progression, metastasis, cell proliferation, tumor cell invasion, or collective migration. In certain embodiments, the individual is identified as having or at risk of having a disease associated with a MaTAR. In certain embodiments, the compound or composition comprises a modified oligonucleotide 8 to 80 linked nucleosides in length and having a nucleobase sequence comprising at least an 8, 9, 10, 11, 12, 13, 14, 15, or 16 contiguous nucleobase portion of any one of SEQ ID NOs: 112-156 and SEQ ID Nos: 169-192. In certain embodiments, the modified oligonucleotide consists of 10 to 30 linked nucleosides.

In certain embodiments, a method of inhibiting expression of a MaTAR in an individual having, or at risk of having, a disease associated with breast cancer comprises administering a MaTAR-specific inhibitor to the individual, thereby inhibiting expression of a MaTAR in the individual. In certain embodiments, the individual has, or is at risk of having breast cancer. In certain embodiments, the breast cancer is luminal B breast cancer. In certain embodiments, the breast cancer is HER2/neu-amplified breast cancer. In certain embodiments, the MaTAR-specific inhibitor is a compound targeted to a MaTAR, such as an oligonucleotide targeted to a MaTAR. In certain embodiments, the MaTAR-specific inhibitor is a compound comprising a modified oligonucleotide consisting of 8 to 80 linked nucleosides and having a nucleobase sequence complementary to any of the nucleobase sequences of SEQ ID NOs: 1-111 and SEQ ID Nos: 193-280. In any of the foregoing embodiments, the compound can be an antisense compound or oligomeric compound. In any of the foregoing embodiments, the compound can be single-stranded or double-stranded. In certain embodiments, the compound or composition comprises a modified oligonucleotide 8 to 80 linked nucleosides in length and having a nucleobase sequence comprising at least an 8, 9, 10, 11, 12, 13, 14, 15, or 16 contiguous nucleobase portion of any one of SEQ ID NOs: 112-156 and SEQ ID Nos: 169-192. In certain embodiments, the modified oligonucleotide consists of 10 to 30 linked nucleosides.

In certain embodiments, a method of inhibiting expression of a MaTAR in a cell comprises contacting the cell with a MaTAR-specific inhibitor, thereby inhibiting expression of a MaTAR in the cell. In certain embodiments, the cell is in an individual who has, or is at risk of having breast cancer. In certain embodiments, the breast cancer is luminal B breast cancer. In certain embodiments, the breast cancer is HER2/neu-amplified breast cancer. In certain embodiments, the MaTAR-specific inhibitor is a compound targeted to a MaTAR, such as an oligonucleotide targeted to a MaTAR. In certain embodiments, the MaTAR-specific inhibitor is a compound comprising a modified oligonucleotide consisting of 8 to 80 linked nucleosides and having a nucleobase sequence complementary to any of the nucleobase sequences of SEQ ID NOs: 1-111 and SEQ ID Nos: 193-280. In any of the foregoing embodiments, the compound can be an antisense compound or oligomeric compound. In any of the foregoing embodiments, the compound can be single-stranded or double-stranded. In certain embodiments, the compound or composition comprises a modified oligonucleotide 8 to 80 linked nucleosides in length and having a nucleobase sequence comprising at least an 8, 9, 10, 11, 12, 13, 14, 15, or 16 contiguous nucleobase portion of any one of SEQ ID NOs: 112-156 and SEQ ID Nos: 169-192. In certain embodiments, the modified oligonucleotide consists of 10 to 30 linked nucleosides.

In certain embodiments, a method of reducing or inhibiting tumor progression, metastasis, cell proliferation, tumor cell invasion, or collective migration in an individual having, or at risk of having, a disease associated with breast cancer comprises administering a MaTAR-specific inhibitor to the individual, thereby reducing or inhibiting tumor progression, metastasis, cell proliferation, tumor cell invasion, or collective migration in the individual. In certain embodiments, the individual has, or is at risk of having, breast cancer. In certain embodiments, the breast cancer is luminal B breast cancer. In certain embodiments, the breast cancer is HER2/neu-amplified breast cancer. In certain embodiments, the MaTAR-specific inhibitor is a compound targeted to a MaTAR, such as an oligonucleotide targeted to a MaTAR. In certain embodiments, the MaTAR-specific inhibitor is a compound comprising a modified oligonucleotide consisting of 8 to 80 linked nucleosides and having a nucleobase sequence complementary to any of the nucleobase sequences of SEQ ID NOs: 1-111 and SEQ ID Nos: 193-280. In any of the foregoing embodiments, the compound can be an antisense compound or oligomeric compound. In any of the foregoing embodiments, the compound can be single-stranded or double-stranded. In certain embodiments, the compound or composition comprises a modified oligonucleotide 8 to 80 linked nucleosides in length and having a nucleobase sequence comprising at least an 8, 9, 10, 11, 12, 13, 14, 15, or 16 contiguous nucleobase portion of any one of SEQ ID NOs: 112-156 and SEQ ID Nos: 169-192. In certain embodiments, the modified oligonucleotide consists of 10 to 30 linked nucleosides.

Certain embodiments are drawn to a MaTAR-specific inhibitor for use in treating a disease associated with breast cancer. In certain embodiments, the breast cancer is luminal B breast cancer. In certain embodiments, the breast cancer is HER2/neu-amplified breast cancer. In certain embodiments, the MaTAR-specific inhibitor is a compound targeted to a MaTAR, such as an oligonucleotide targeted to a MaTAR. In certain embodiments, the MaTAR-specific inhibitor is a compound comprising a modified oligonucleotide consisting of 8 to 80 linked nucleosides and having a nucleobase sequence complementary to any of the nucleobase sequences of SEQ ID NOs: 1-111 and SEQ ID Nos: 193-280. In any of the foregoing embodiments, the compound can be an antisense compound or oligomeric compound. In any of the foregoing embodiments, the compound can be single-stranded or double-stranded. In certain embodiments, the compound or composition comprises a modified oligonucleotide 8 to 80 linked nucleosides in length and having a nucleobase sequence comprising at least an 8, 9, 10, 11, 12, 13, 14, 15, or 16 contiguous nucleobase portion of any one of SEQ ID NOs: 112-156 and SEQ ID Nos: 169-192. In certain embodiments, the modified oligonucleotide consists of 10 to 30 linked nucleosides.

Certain embodiments are drawn to a MaTAR-specific inhibitor for use in reducing or inhibiting tumor progression, metastasis, cell proliferation, tumor cell invasion, or collective migration in an individual having or at risk of having breast cancer. In certain embodiments, the breast cancer is luminal B breast cancer. In certain embodiments, the breast cancer is HER2/neu-amplified breast cancer. In certain embodiments, the MaTAR-specific inhibitor is a compound targeted to a MaTAR, such as an oligonucleotide targeted to a MaTAR. In certain embodiments, the MaTAR-specific inhibitor is a compound comprising a modified oligonucleotide consisting of 8 to 80 linked nucleosides and having a nucleobase sequence complementary to any of the nucleobase sequences of SEQ ID NOs: 1-111 and SEQ ID Nos: 193-280. In any of the foregoing embodiments, the compound can be an antisense compound or oligomeric compound. In any of the foregoing embodiments, the compound can be single-stranded or double-stranded. In certain embodiments, the compound or composition comprises a modified oligonucleotide 8 to 80 linked nucleosides in length and having a nucleobase sequence comprising at least an 8, 9, 10, 11, 12, 13, 14, 15, or 16 contiguous nucleobase portion of any one of SEQ ID NOs: 112-156 and SEQ ID Nos: 169-192. In certain embodiments, the modified oligonucleotide consists of 10 to 30 linked nucleosides.

Certain embodiments are drawn to use of a MaTAR-specific inhibitor for the manufacture of a medicament for treating a disease associated with breast cancer. Certain embodiments are drawn to use of a MaTAR-specific inhibitor for the preparation of a medicament for treating breast cancer. In certain embodiments, the breast cancer is luminal B breast cancer. In certain embodiments, the breast cancer is HER2/neu-amplified breast cancer. In certain embodiments, the MaTAR-specific inhibitor is a compound targeted to a MaTAR, such as an oligonucleotide targeted to a MaTAR. In certain embodiments, the MaTAR-specific inhibitor is a compound comprising a modified oligonucleotide consisting of 8 to 80 linked nucleosides and having a nucleobase sequence complementary to any of the nucleobase sequences of SEQ ID NOs: 1-111 and SEQ ID Nos: 193-280. In any of the foregoing embodiments, the compound can be an antisense compound or oligomeric compound. In any of the foregoing embodiments, the compound can be single-stranded or double-stranded. In certain embodiments, the compound or composition comprises a modified oligonucleotide 8 to 80 linked nucleosides in length and having a nucleobase sequence comprising at least an 8, 9, 10, 11, 12, 13, 14, 15, or 16 contiguous nucleobase portion of any one of SEQ ID NOs: 112-156 and SEQ ID Nos: 169-192. In certain embodiments, the modified oligonucleotide consists of 10 to 30 linked nucleosides.

Certain embodiments are drawn to use of a MaTAR-specific inhibitor for the manufacture of a medicament for reducing or inhibiting tumor progression, metastasis, cell proliferation, tumor cell invasion, or collective migration in an individual having or at risk of having breast cancer. In certain embodiments, the breast cancer is luminal B breast cancer. In certain embodiments, the breast cancer is HER2/neu-amplified breast cancer. In certain embodiments, the MaTAR-specific inhibitor is a compound targeted to a MaTAR, such as an oligonucleotide targeted to a MaTAR. In certain embodiments, the MaTAR-specific inhibitor is a compound comprising a modified oligonucleotide consisting of 8 to 80 linked nucleosides and having a nucleobase sequence complementary to any of the nucleobase sequences of SEQ ID NOs: 1-111 and SEQ ID Nos: 193-280. In any of the foregoing embodiments, the compound can be an antisense compound or oligomeric compound. In any of the foregoing embodiments, the compound can be single-stranded or double-stranded. In certain embodiments, the compound or composition comprises a modified oligonucleotide 8 to 80 linked nucleosides in length and having a nucleobase sequence comprising at least an 8, 9, 10, 11, 12, 13, 14, 15, or 16 contiguous nucleobase portion of any one of SEQ ID NOs: 112-156 and SEQ ID Nos: 169-192. In certain embodiments, the modified oligonucleotide consists of 10 to 30 linked nucleosides.

In any of the foregoing methods or uses, the compound can be an antisense compound targeted to a MaTAR. In certain embodiments, the compound comprises an oligonucleotide, for example an oligonucleotide consisting of 8 to 80 linked nucleosides, 10 to 30 linked nucleosides, 12 to 30 linked nucleosides, or 20 linked nucleosides. In certain embodiments, the oligonucleotide is at least 80%, 85%, 90%, 95% or 100% complementary to any of the nucleobase sequences recited in SEQ ID NOs: 1-111 and SEQ ID Nos: 193-280. In certain embodiments, the oligonucleotide comprises at least one modified internucleoside linkage, at least one modified sugar and/or at least one modified nucleobase. In certain embodiments, the modified internucleoside linkage is a phosphorothioate internucleoside linkage, the modified sugar is a bicyclic sugar or a 2'-O-methoxyethyl, and the modified nucleobase is a 5-methylcytosine. In certain embodiments, the modified oligonucleotide comprises a gap segment consisting of linked deoxynucleosides; a 5' wing segment consisting of linked nucleosides; and a 3' wing segment consisting of linked nucleosides, wherein the gap segment is positioned immediately adjacent to and between the 5' wing segment and the 3' wing segment and wherein each nucleoside of each wing segment comprises a modified sugar. In certain embodiments, the compound or composition comprises a modified oligonucleotide 8 to 80 linked nucleosides in length and having a nucleobase sequence comprising at least an 8, 9, 10, 11, 12, 13, 14, 15, or 16 contiguous nucleobase portion of any one of SEQ ID NOs: 112-156 and SEQ ID Nos: 169-192. In certain embodiments, the modified oligonucleotide consists of 10 to 30 linked nucleosides.

In any of the foregoing embodiments, the oligonucleotide consists of 12 to 30, 15 to 30, 15 to 25, 15 to 24, 16 to 24, 17 to 24, 18 to 24, 19 to 24, 20 to 24, 19 to 22, 20 to 22, 16 to 20, or 17 or 20 linked nucleosides. In certain aspects, the oligonucleotide is at least 80%, 85%, 90%, 95% or 100% complementary to any of the nucleobase sequences recited in SEQ ID NOs: 1-111 and SEQ ID Nos: 193-280. In certain aspects, the oligonucleotide comprises at least one modified internucleoside linkage, at least one modified sugar and/or at least one modified nucleobase. In certain aspects, the modified internucleoside linkage is a phosphorothioate internucleoside linkage, the modified sugar is a bicyclic sugar or a 2'-O-methoxyethyl, and the modified nucleobase is a 5-methylcytosine. In certain aspects, the modified oligonucleotide comprises a gap segment consisting of linked 2'-deoxynucleosides; a 5' wing segment consisting of linked nucleosides; and a 3' wing segment consisting of linked nucleosides, wherein the gap segment is positioned immediately adjacent to and between the 5' wing segment and the 3' wing segment and wherein each nucleoside of each wing segment comprises a modified sugar. In certain embodiments, the compound or composition comprises a modified oligonucleotide 8 to 80 linked nucleosides in length and having a nucleobase sequence comprising at least an 8, 9, 10, 11, 12, 13, 14, 15, or 16 contiguous nucleobase portion of any one of SEQ ID NOs: 112-156 and SEQ ID Nos: 169-192. In certain embodiments, the modified oligonucleotide consists of 10 to 30 linked nucleosides.

In any of the foregoing methods or uses, the compound comprises or consists of a modified oligonucleotide 12 to 30 linked nucleosides in length and having a nucleobase sequence complementary to any one of SEQ ID NOs: 1-111 and SEQ ID Nos: 193-280, wherein the modified oligonucleotide comprises:
   a gap segment consisting of linked 2'-deoxynucleosides;
   a 5' wing segment consisting of linked nucleosides; and
   a 3' wing segment consisting of linked nucleosides;
   wherein the gap segment is positioned between the 5' wing segment and the 3' wing segment and wherein each nucleoside of each wing segment comprises a modified sugar. In certain embodiments, the compound or composition comprises a modified oligonucleotide 8 to 80 linked nucleosides in length and having a nucleobase sequence comprising at least an 8, 9, 10, 11, 12, 13, 14, 15, or 16 contiguous nucleobase portion of any one of SEQ ID NOs: 112-156 and SEQ ID Nos: 169-192. In certain embodiments, the modified oligonucleotide consists of 10 to 30 linked nucleosides.

In any of the foregoing methods or uses, the compound can be administered parenterally. For example, in certain embodiments the compound can be administered through injection or infusion. Parenteral administration includes subcutaneous administration, intravenous administration, intramuscular administration, intraarterial administration, intraperitoneal administration, or intracranial administration.

Certain Compounds

In certain embodiments, compounds described herein are antisense compounds. In certain embodiments, the antisense compound comprises or consists of an oligomeric compound. In certain embodiments, the oligomeric compound comprises a modified oligonucleotide. In certain embodiments, the modified oligonucleotide has a nucleobase sequence complementary to that of a target nucleic acid.

In certain embodiments, a compound described herein comprises or consists of a modified oligonucleotide. In certain embodiments, the modified oligonucleotide has a nucleobase sequence complementary to that of a target nucleic acid.

In certain embodiments, a compound or antisense compound is single-stranded. Such a single-stranded compound or antisense compound comprises or consists of an oligomeric compound. In certain embodiments, such an oligomeric compound comprises or consists of an oligonucleotide and optionally a conjugate group. In certain embodiments, the oligonucleotide is an antisense oligonucleotide. In certain embodiments, the oligonucleotide is modified. In certain embodiments, the oligonucleotide of a single-stranded antisense compound or oligomeric compound comprises a self-complementary nucleobase sequence.

In certain embodiments, compounds are double-stranded. Such double-stranded compounds comprise a first modified oligonucleotide having a region complementary to a target nucleic acid and a second modified oligonucleotide having a region complementary to the first modified oligonucleotide. In certain embodiments, the modified oligonucleotide is an RNA oligonucleotide. In such embodiments, the thymine nucleobase in the modified oligonucleotide is replaced by a uracil nucleobase. In certain embodiments, compound comprises a conjugate group. In certain embodiments, one of the modified oligonucleotides is conjugated. In certain embodiments, both the modified oligonucleotides are conjugated. In certain embodiments, the first modified oligonucleotide is conjugated. In certain embodiments, the second modified oligonucleotide is conjugated. In certain embodiments, each modified oligonucleotide is 12-30 linked nucleosides in length.

In certain embodiments, compounds are double-stranded. Such double-stranded compounds comprise a first oligomeric compound having a region complementary to a target nucleic acid and a second oligomeric compound having a region complementary to the first oligomeric compound. The first oligomeric compound of such double stranded compounds typically comprises or consists of a modified oligonucleotide and optionally a conjugate group. The oligonucleotide of the second oligomeric compound of such double-stranded compound may be modified or unmodified. Either or both oligomeric compounds of a double-stranded compound may comprise a conjugate group. The oligomeric compounds of double-stranded compounds may include non-complementary overhanging nucleosides.

Examples of single-stranded and double-stranded compounds include but are not limited to oligonucleotides, siRNAs, microRNA targeting oligonucleotides, and single-stranded RNAi compounds, such as small hairpin RNAs (shRNAs), single-stranded siRNAs (ssRNAs), and microRNA mimics.

In certain embodiments, a compound described herein has a nucleobase sequence that, when written in the 5' to 3' direction, comprises the reverse complement of the target segment of a target nucleic acid to which it is targeted.

In certain embodiments, a compound described herein comprises an oligonucleotide 10 to 30 linked subunits in length. In certain embodiments, compound described herein comprises an oligonucleotide is 12 to 30 linked subunits in length. In certain embodiments, compound described herein comprises an oligonucleotide is 12 to 22 linked subunits in length. In certain embodiments, compound described herein comprises an oligonucleotide is 14 to 30 linked subunits in length. In certain embodiments, compound described herein comprises an oligonucleotide is 14 to 20 linked subunits in length. In certain embodiments, compound described herein comprises an oligonucleotide is 15 to 30 linked subunits in length. In certain embodiments, compound described herein comprises an oligonucleotide is 15 to 20 linked subunits in length. In certain embodiments, compound described herein comprises an oligonucleotide is 16 to 30 linked subunits in length. In certain embodiments, compound described herein comprises an oligonucleotide is 16 to 20 linked subunits in length. In certain embodiments, compound described herein comprises an oligonucleotide is 17 to 30 linked subunits in length. In certain embodiments, compound described herein comprises an oligonucleotide is 17 to 20 linked subunits in length. In certain embodiments, compound described herein comprises an oligonucleotide is 18 to 30 linked subunits in length. In certain embodiments, compound described herein comprises an oligonucleotide is 18 to 21 linked subunits in length. In certain embodiments, compound described herein comprises an oligonucleotide is 18 to 20 linked subunits in length. In certain embodiments, compound described herein comprises an oligonucleotide is 20 to 30 linked subunits in length. In other words, such oligonucleotides are from 12 to 30 linked subunits, 14 to 30 linked subunits, 14 to 20 subunits, 15 to 30 subunits, 15 to 20 subunits, 16 to 30 subunits, 16 to 20 subunits, 17 to 30 subunits, 17 to 20 subunits, 18 to 30 subunits, 18 to 20 subunits, 18 to 21 subunits, 20 to 30 subunits, or 12 to 22 linked subunits, respectively. In certain embodiments, a compound described herein comprises an oligonucleotide 14 linked subunits in length. In certain embodiments, a compound described herein comprises an oligonucleotide 16 linked subunits in length. In certain embodiments, a compound described herein comprises an oligonucleotide 17 linked subunits in length. In certain embodiments, compound described herein comprises an oligonucleotide 18 linked subunits in length. In certain embodiments, a compound described herein comprises an oligonucleotide 19 linked subunits in length. In certain embodiments, a compound described herein comprises an oligonucleotide 20 linked subunits in length. In other embodiments, a compound described herein comprises an oligonucleotide 8 to 80, 12 to 50, 13 to 30, 13 to 50, 14 to 30, 14 to 50, 15 to 30, 15 to 50, 16 to 30, 16 to 50, 17 to 30, 17 to 50, 18 to 22, 18 to 24, 18 to 30, 18 to 50, 19 to 22, 19 to 30, 19 to 50, or 20 to 30 linked subunits. In certain such embodiments, the compound described herein comprises an oligonucleotide 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments the linked subunits are nucleotides, nucleosides, or nucleobases.

In certain embodiments, the compound may further comprise additional features or elements, such as a conjugate group, that are attached to the oligonucleotide. In certain embodiments, such compounds are antisense compounds. In certain embodiments, such compounds are oligomeric compounds. In embodiments where a conjugate group comprises a nucleoside (i.e. a nucleoside that links the conjugate group to the oligonucleotide), the nucleoside of the conjugate group is not counted in the length of the oligonucleotide.

In certain embodiments, compounds may be shortened or truncated. For example, a single subunit may be deleted from the 5' end (5' truncation), or alternatively from the 3' end (3' truncation). A shortened or truncated compound targeted to a MaTAR nucleic acid may have two subunits deleted from the 5' end, or alternatively may have two subunits deleted from the 3' end, of the compound. Alternatively, the deleted nucleosides may be dispersed throughout the compound.

When a single additional subunit is present in a lengthened compound, the additional subunit may be located at the 5' or 3' end of the compound. When two or more additional subunits are present, the added subunits may be adjacent to each other, for example, in a compound having two subunits added to the 5' end (5' addition), or alternatively to the 3' end (3' addition), of the compound. Alternatively, the added subunits may be dispersed throughout the compound.

It is possible to increase or decrease the length of a compound, such as an oligonucleotide, and/or introduce mismatch bases without eliminating activity (Woolf et al. (Proc. Natl. Acad. Sci. USA 89:7305-7309, 1992; Gautschi et al. *J. Natl. Cancer Inst.* 93:463-471, March 2001; Maher and Dolnick *Nuc. Acid. Res.* 16:3341-3358, 1988). However, seemingly small changes in oligonucleotide sequence, chemistry and motif can make large differences in one or more of the many properties required for clinical development (Seth et al. *J. Med. Chem.* 2009, 52, 10; Egli et al. *J. Am. Chem. Soc.* 2011, 133, 16642).

In certain embodiments, compounds described herein are interfering RNA compounds (RNAi), which include double-stranded RNA compounds (also referred to as short-interfering RNA or siRNA) and single-stranded RNAi compounds (or ssRNA). Such compounds work at least in part through the RISC pathway to degrade and/or sequester a target nucleic acid (thus, include microRNA/microRNA-mimic compounds). As used herein, the term siRNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically modified siRNA, post-transcriptional gene silencing RNA (ptgsRNA), and others. In addition, as used herein, the term RNAi is meant to be equivalent to other terms used to describe sequence specific RNA interference, such as post transcriptional gene silencing, translational inhibition, or epigenetics.

In certain embodiments, a double-stranded compound described herein can comprise any of the oligonucleotide sequences targeted to a MaTAR described herein. In certain embodiments, a double-stranded compound comprises a first strand comprising sequence complementary to any one of SEQ ID NOs: 1-111 and SEQ ID Nos: 193-280 and a second strand.

In certain embodiments, a double-stranded compound comprises a first strand comprising the nucleobase sequence complementary to any one of SEQ ID NOs: 1-111 and SEQ ID Nos: 193-280 and a second strand. In certain embodiments, the double-stranded compound comprises ribonucleotides in which the first strand has uracil (U) in place of thymine (T) and is complementary to any one of SEQ ID NOs: 1-111 and SEQ ID Nos: 193-280. In certain embodiments, a double-stranded compound comprises (i) a first strand comprising a nucleobase sequence complementary to the site on a MaTAR of any of SEQ ID NOs: 1-111 and SEQ ID Nos: 193-280, and (ii) a second strand. In certain embodiments, the double-stranded compound comprises one or more modified nucleotides in which the 2' position in the sugar contains a halogen (such as fluorine group; 2'-F) or contains an alkoxy group (such as a methoxy group; 2'-OMe). In certain embodiments, the double-stranded compound comprises at least one 2'-F sugar modification and at least one 2'-OMe sugar modification. In certain embodiments, the at least one 2'-F sugar modification and at least one 2'-OMe sugar modification are arranged in an alternating pattern for at least 2, 3, 4, 5, 6, 7, 8, 9, 10, 11, 12, 13, 14, 15, 16, 17, 18, 19, or 20 contiguous nucleobases along a strand of the dsRNA compound. In certain embodiments, the double-stranded compound comprises one or more linkages between adjacent nucleotides other than a naturally-occurring phosphodiester linkage. Examples of such linkages include phosphoramide, phosphorothioate, and phosphorodithioate linkages. The double-stranded compounds may also be chemically modified nucleic acid molecules as taught in U.S. Pat. No. 6,673,661. In other embodiments, the dsRNA contains one or two capped strands, as disclosed, for example, by WO 00/63364, filed Apr. 19, 2000. In certain embodiments, the first strand of the double-stranded compound is an siRNA guide strand and the second strand of the double-stranded compound is an siRNA passenger strand. In certain embodiments, the second strand of the double-stranded compound is complementary to the first strand. In certain embodiments, each strand of the double-stranded compound consists of 16, 17, 18, 19, 20, 21, 22, or 23 linked nucleosides. In certain embodiments, the first or second strand of the double-stranded compound can comprise a conjugate group.

In certain embodiments, a single-stranded compound described herein can comprise any of the oligonucleotide sequences targeted to a MaTAR described herein. In certain embodiments, such a single-stranded compound is a single-stranded RNAi (ssRNAi) compound. In certain embodiments, a ssRNAi compound comprises at least an 8, 9, 10, 11, 12, 13, 14, 15, 16, 17, 18, 19, or 20 contiguous nucleobase portion complementary to any one of SEQ ID NOs: 1-111 and SEQ ID Nos: 193-280. In certain embodiments, a ssRNAi compound comprises the nucleobase sequence complementary to any one of SEQ ID NOs: 1-111 and SEQ ID Nos: 193-280. In certain embodiments, the ssRNAi compound comprises ribonucleotides in which uracil (U) is in place of thymine (T). In certain embodiments, ssRNAi compound comprises a nucleobase sequence complementary to the site on a MaTAR with any of the the sequences of SEQ ID NOs: 1-111 and SEQ ID Nos: 193-280. In certain embodiments, a ssRNAi compound comprises one or more modified nucleotides in which the 2' position in the sugar contains a halogen (such as fluorine group; 2'-F) or contains an alkoxy group (such as a methoxy group; 2'-OMe). In certain embodiments, a ssRNAi compound comprises at least one 2'-F sugar modification and at least one 2'-OMe sugar modification. In certain embodiments, the at least one 2'-F sugar modification and at least one 2'-OMe sugar modification are arranged in an alternating pattern for at least 2, 3, 4, 5, 6, 7, 8, 9, 10, 11, 12, 13, 14, 15, 16, 17, 18, 19, or 20 contiguous nucleobases along a strand of the ssRNAi compound. In certain embodiments, the ssRNAi compound comprises one or more linkages between adjacent nucleotides other than a naturally-occurring phosphodiester linkage. Examples of such linkages include phosphoramide, phosphorothioate, and phosphorodithioate linkages. The ssRNAi compounds may also be chemically modified nucleic acid molecules as taught in U.S. Pat. No. 6,673,661. In other embodiments, the ssRNAi contains a capped strand, as disclosed, for example, by WO 00/63364, filed Apr. 19, 2000. In certain embodiments, the ssRNAi compound consists of 16, 17, 18, 19, 20, 21, 22, or 23 linked nucleosides. In certain embodiments, the ssRNAi compound can comprise a conjugate group.

In certain embodiments, compounds described herein comprise modified oligonucleotides. Certain modified oligonucleotides have one or more asymmetric center and thus give rise to enantiomers, diastereomers, and other stereoisomeric configurations that may be defined, in terms of absolute stereochemistry, as (R) or (S), as a or 13 such as for sugar anomers, or as (D) or (L) such as for amino acids etc. Included in the modified oligonucleotides provided herein are all such possible isomers, including their racemic and optically pure forms, unless specified otherwise. Likewise, all cis- and trans-isomers and tautomeric forms are also included.

Certain Mechanisms

In certain embodiments, compounds described herein comprise or consist of modified oligonucleotides. In certain embodiments, compounds described herein are antisense compounds. In certain embodiments, such antisense compounds comprise oligomeric compounds. In certain embodiments, compounds described herein are capable of hybridizing to a target nucleic acid, resulting in at least one antisense activity. In certain embodiments, compounds described herein selectively affect one or more target nucleic acid. Such selective compounds comprise a nucleobase sequence that hybridizes to one or more target nucleic acid, resulting in one or more desired antisense activity and does not hybridize to one or more non-target nucleic acid or does not hybridize to one or more non-target nucleic acid in such a way that results in a significant undesired antisense activity.

In certain antisense activities, hybridization of a compound described herein to a target nucleic acid results in recruitment of a protein that cleaves the target nucleic acid. For example, certain compounds described herein result in RNase H mediated cleavage of the target nucleic acid. RNase H is a cellular endonuclease that cleaves the RNA strand of an RNA:DNA duplex. The DNA in such an RNA:DNA duplex need not be unmodified DNA. In certain embodiments, compounds described herein are sufficiently "DNA-like" to elicit RNase H activity. Further, in certain embodiments, one or more non-DNA-like nucleoside in the gap of a gapmer is tolerated.

In certain antisense activities, compounds described herein or a portion of the compound is loaded into an RNA-induced silencing complex (RISC), ultimately resulting in cleavage of the target nucleic acid. For example, certain compounds described herein result in cleavage of the target nucleic acid by Argonaute. Compounds that are loaded into RISC are RNAi compounds. RNAi compounds may be double-stranded (siRNA) or single-stranded (ssRNA).

In certain embodiments, hybridization of compounds described herein to a target nucleic acid does not result in recruitment of a protein that cleaves that target nucleic acid. In certain such embodiments, hybridization of the compound to the target nucleic acid results in alteration of splicing of the target nucleic acid. In certain embodiments, hybridization of the compound to a target nucleic acid results in inhibition of a binding interaction between the target nucleic acid and a protein or other nucleic acid. In certain such embodiments, hybridization of the compound to a target nucleic acid results in alteration of translation of the target nucleic acid.

Antisense activities may be observed directly or indirectly. In certain embodiments, observation or detection of an antisense activity involves observation or detection of a change in an amount of a target nucleic acid or protein encoded by such target nucleic acid, a change in the ratio of splice variants of a nucleic acid or protein, and/or a phenotypic change in a cell or animal.

Target Nucleic Acids, Target Regions and Nucleotide Sequences

In certain embodiments, compounds described herein comprise or consist of an oligonucleotide comprising a region that is complementary to a target nucleic acid. In certain embodiments, the target nucleic acid is an endogenous RNA molecule. In certain such embodiments, the target nucleic acid is selected from: an mRNA and a pre-mRNA, including intronic, exonic and untranslated regions. In certain embodiments, the target nucleic acid is a pre-mRNA. In certain such embodiments, the target region is entirely within an intron. In certain embodiments, the target region spans an intron/exon junction. In certain embodiments, the target region is at least 50% within an intron. In certain embodiments, the target region is an lncRNA.

Human gene sequences that encode a MaTAR include, without limitation, the following gene sequences, as listed in the Tables below:

TABLE 1

Bioinformatically identified human gene sequences for MaTARs identified in murine models of human breast cancer

| MaTAR # | Human gene sequence | SEQ ID NO |
|---|---|---|
| 1 | The complement of NC_000005.10 truncated from nucleotides 88540779 to 88684803 | 1 |
| 2 | The complement of NC_000016.10 truncated from nucleotides 66932055 to 66934423 | 2 |
| 3 | The complement of NC_000004.12 truncated from nucleotides 90121784 to 90121954 | 3 |
| 4 | NC_000007.14 truncated from nucleotides 27096094 to 27100258 | 4 |
| 5 | NC_000021.9 truncated from nucleotides 18857779 to 18858276 | 5 |
| 6 | NC_000006.12 truncated from nucleotides 30766825 to 30792250 | 6 |
|   | The complement of NC_000006.12 truncated from nucleotides 30812866-30830659 | 7 |
| 7 | The complement of NC_000001.11 truncated from nucleotides 47432133 to 47434641 | 8 |
| 8 | NC_000018.10 truncated from nucleotides 48955665 to 48956059 | 9 |
|   | The complement of NC_000018.10 truncated from nucleotides 48962951 to 48963941 | 10 |
| 9 | NC_000007.14 truncated from nucleotides 99374675 to 99394781 | 11 |
|   | The complement of NC_000007.14 truncated from nucleotides 99394676 to 99408682 | 12 |
| 10 | The complement of NC_000001.11 truncated from nucleotides 183555563 to 183590876 | 13 |
|   | The complement of NC_000005.10 truncated from nucleotides 56504635 to 56505072 | 14 |
|   | NC_000005.10 truncated from nucleotides 56381781 to 56382075 | 15 |
|   | The complement of NC_000005.10 truncated from nucleotides 56275304 to 56276630 | 16 |
|   | The complement of NC_000005.10 truncated from nucleotides 56504635 to 56505073 | 17 |
| 11 | NC_000009.12 truncated from nucleotides 104927553 to 104928892 | 18 |
| 12 | The complement of NC_000003.12 truncated from nucleotides 141050613 to 141052013 | 19 |
|   | The complement of NC_000003.12 truncated from nucleotides 141115124 to 141124182 | 20 |
| 13 | NC_000002.12 truncated from nucleotides 230125310 to 230167494 | 21 |
| 14 | The complement of NC_000002.12 truncated from nucleotides 230309741 to 230311581 | 22 |
|   | The complement of NC_000002.12 truncated from nucleotides 230401360 to 230401793 | 23 |
| 15 | NC_000023.11 truncated from nucleotides 148052233 to 148052746 | 24 |
|   | The complement of NC_000023.11 truncated from nucleotides 30290047 to 30290351 | 25 |
|   | The complement of NC_000023.11 truncated from nucleotides 30017160 to 30017881 | 26 |
| 16 | NC_000001.11 truncated from nucleotides 55217861 to 55234177 | 27 |
|   | NC_000001.11 truncated from nucleotides 55215408 to 55217455 | 28 |
| 17 | NC_000007.14 truncated from nucleotides 101299613 to 101301270 | 29 |
|   | NC_000007.14 truncated from nucleotides 101308346 to 101310985 | 30 |

TABLE 1-continued

Bioinformatically identified human gene sequences for MaTARs identified in murine models of human breast cancer

| MaTAR # | Human gene sequence | SEQ ID NO |
|---|---|---|
|  | The complement of NC_000007.14 truncated from nucleotides 101287482 to 101289771 | 31 |
| 18 | NC_000001.11 truncated from nucleotides 51329654 to 51331281 | 32 |
| 19 | NC_000007.14 truncated from nucleotides 100509717 to 100519926 | 33 |
| 20 | NC_000009.12 truncated from nucleotides 137286112 to 137287236 | 34 |
|  | The complement of NC_000009.12 truncated from nucleotides 137293868 to 137295721 | 35 |
| 21 | NC_000022.11 truncated from nucleotides 31617011 to 31617070 | 36 |
| 22 | NC_000008.11 truncated from nucleotides 58503588 to 58504068 | 37 |
| 23 | The complement of NC_000005.10 truncated from nucleotides 70968483 to 71025114 | 38 |
| 24 | NC_000013.11 truncated from nucleotides 81689911 to 81691072 | 39 |
|  | The complement of NC_000009.12 truncated from nucleotides 36303499 to 36304924 | 40 |
| 25 | The complement of NC_000020.11 truncated from nucleotides 50310711 to 50321342 | 41 |
|  | NC_000020.11 truncated from nucleotides 50292720 to 50314922 | 42 |
|  | NC_000020.11 truncated from nucleotides 50267486 to 50279795 | 43 |
| 26 | NC_000006.12 truncated from nucleotides 144216543 to 144216627 | 44 |
|  | The complement of NC_000006.12 truncated from nucleotides 144200447 to 144200965 | 45 |
|  | The complement of NC_000006.12 truncated from nucleotides 144257034 to 144257624 | 46 |
| 27 | The complement of NC_000007.14 truncated from nucleotides 5527155 to 5529569 | 47 |
|  | NC_000023.11 truncated from nucleotides 53001527 to 53001617 | 48 |
| 28 | NC_000001.11 truncated from nucleotides 55222379 to 55223372 | 49 |
|  | NC_000001.11 truncated from nucleotides 55217861 to 55234178 | 50 |
|  | NC_000001.11 truncated from nucleotides 55215408 to 55217456 | 51 |
| 29 | The complement of NC_000011.10 truncated from nucleotides 59781318 to 59781722 | 52 |
|  | The complement of NC_000018.10 truncated from nucleotides 50256036 to 50256461 | 53 |
| 30 | The complement of NC_000015.10 truncated from nucleotides 74976240 to 74976573 | 54 |
|  | The complement of NC_000015.10 truncated from nucleotides 74983274 to 74983376 | 55 |
|  | The complement of NC000011.10 truncated from nucleotides 59781318 to 59781723 | 56 |

The human equivalent gene sequences that were found to be upregulated in mammary carcinoma tissue (as exemplified in the Examples below) are further provided in the Table below:

TABLE 2

Human equivalent gene sequences of lncRNAs

| Gene name | Gene sequence | SEQ ID NO |
|---|---|---|
| predicted gene, OTTMUSG00000005723 | NC_000005.10 truncated from nucleotides 154993598 to 154994445 | 57 |
| ENSMUST00000180755 | NC_000012.12 truncated from nucleotides 6533927 to 6538371 | 58 |
| ENSMUST00000180755 | The complement of NC_000004.12 truncated from nucleotides 77350370 to 77351235 | 59 |

TABLE 2-continued

Human equivalent gene sequences of lncRNAs

| Gene name | Gene sequence | SEQ ID NO |
|---|---|---|
| ENSMUST00000180755 | The complement of NC_000004.12 truncated from nucleotides 77311397 to 77312111 | 60 |
| ENSMUST00000180755 | The complement of NC_000004.12 truncated from nucleotides 77216416 to 77216878 | 61 |
| ENSMUST00000187117 | NC_000006.12 truncated from nucleotides 69745871 to 69746851 | 62 |
| ENSMUST00000187117 | The complement of NC_000006.12 truncated from nucleotides 69705287 to 69706160 | 63 |
| ENSMUST00000187117 | The complement of NC_000006.12 truncated from nucleotides 70098390 to 70098676 | 64 |
| ENSMUST00000181833 | NC_000004.12 truncated from nucleotides 128768228 to 128769948 | 65 |
| ENSMUST00000181833 | The complement of NC_000004.12 truncated from nucleotides 128582999 to 128601400 | 66 |
| ENSMUST00000186885 | NC_000002.12 truncated from nucleotides 125710969 to 125765842 | 67 |
| ENSMUST00000186885 | The complement of NC_000002.12 truncated from nucleotides 126110099 to 126117985 | 68 |
| ENSMUST00000187677 | NC_000002.12 truncated from nucleotides 192629919 to 192645706 | 69 |
| ENSMUST00000187677 | The complement of NC_000002.12 truncated from nucleotides 192644102 to 192645387 | 70 |
| ENSMUST00000187677 | NC_000002.12 truncated from nucleotides 192749845 to 192776899 | 71 |
| ENSMUST00000189594 | The complement of NC_000001.11 truncated from nucleotides 224175476 to 224175706 | 72 |
| ENSMUST00000189594 | The complement of NC_000001.11 truncated from nucleotides 224208747 to 224213279 | 73 |
| ENSMUST00000189594 | NC_000001.11 truncated from nucleotides 224219613 to 224228043 | 74 |
| ENSMUST00000191042 | NC_000005.10 truncated from nucleotides 102144077 to 102146572 | 75 |
| ENSMUST00000192612 | NC_000003.12 truncated from nucleotides 143111802 to 143112359 | 76 |
| ENSMUST00000195727 | The complement of NC_000008.11 truncated from nucleotides 81275399 to 81277570 | 77 |
| ENSMUST00000195727 | The complement of NC_000008.11 truncated from nucleotides 81279871 to 81281446 | 78 |
| ENSMUST00000195727 | NC_000008.11 truncated from nucleotides 81154279 to 81159083 | 79 |
| ENSMUST00000197386 | The complement of NC_000004.12 truncated from nucleotides 106003317 to 106022478 | 80 |
| ENSMUST00000199279 | NC_000012.12 truncated from nucleotides 121190868 to 121191518 | 81 |
| ENSMUST00000199279 | NC_000012.12 truncated from nucleotides 121391962 to 121399859 | 82 |
| ENSMUST00000200473 | NC_000004.12 truncated from nucleotides 16178939 to 16183120 | 83 |
| ENSMUST00000200473 | NC_000004.12 truncated from nucleotides 16400430 to 16512187 | 84 |
| ENSMUST00000123623 | NC_000011.10 truncated from nucleotides 30584130 to 30630508 | 85 |
| ENSMUST00000139492 | The complement of NC_000002.12 truncated from nucleotides 188035596 to 188287691 | 86 |
| ENSMUST00000143673 | The complement of NC_000017.11 truncated from nucleotides 35540039 to 35540797 | 87 |
| ENSMUST00000155384 | The complement of NC_000017.11 truncated from nucleotides 77879027 to 77884087 | 88 |
| ENSMUST00000181029 | The complement of NC_000006.12 truncated from nucleotides 35733867 to 35736947 | 89 |
| ENSMUST00000185425 | NC_000002.12 truncated from nucleotides 234682668 to 234717764 | 90 |
| ENSMUST00000185425 | The complement of NC_000002.12 truncated from nucleotides 234882279 to 234888802 | 91 |
| ENSMUST00000191737 | NC_000001.11 truncated from nucleotides 111250254 to 111256715 | 92 |
| ENSMUST00000191737 | The complement of NC_000001.11 truncated from nucleotides 111184415 to 111185061 | 93 |
| ENSMUST00000196337 | NC_000004.12 truncated from nucleotides 128428070 to 128519394 | 94 |
| ENSMUST00000196668 | The complement of NC_000001.11 truncated from nucleotides 87353524 to 87371655 | 95 |
| ENSMUST00000196668 | The complement of NC_000001.11 truncated from nucleotides 87899909 to 87905714 | 96 |

TABLE 2-continued

Human equivalent gene sequences of lncRNAs

| Gene name | Gene sequence | SEQ ID NO |
|---|---|---|
| ENSMUST00000196668 | The complement of NC_000001.11 truncated from nucleotides 87805286 to 87808372 | 97 |
| ENSMUST00000198677 | The complement of NC_000004.12 truncated from nucleotides 16360686 to 16361826 | 98 |
| ENSMUST00000198677 | NC_000004.12 truncated from nucleotides 16400430 to 16512188 | 99 |
| ENSMUST00000200327 | NC_000004.12 truncated from nucleotides 104490965 to 104697592 | 100 |
| ENSMUST00000200327 | NC_000004.12 truncated from nucleotides 104973712 to 105120000 | 101 |
| ENSMUST00000200327 | The complement of NC_000004.12 truncated from nucleotides 104653874 to 104966793 | 102 |
| ENSMUST00000188231 | NC_000006.12 truncated from nucleotides 69745871 to 69746852 | 103 |
| ENSMUST00000188231 | The complement of NC_000006.12 truncated from nucleotides 69705287 to 69706161 | 104 |
| ENSMUST00000188231 | The complement of NC_000006.12 truncated from nucleotides 70098390 to 70098677 | 105 |
| ENSMUST00000187714 | NC_000006.12 truncated from nucleotides 69745870 to 69746851 | 106 |
| ENSMUST00000187714 | The complement of NC_000006.12 truncated from nucleotides 69705286 to 69706160 | 107 |
| ENSMUST00000187714 | The complement of NC_000006.12 truncated from nucleotides 70098389 to 70098676 | 108 |
| ENSMUST00000146576 | The complement of NC_000009.12 truncated from nucleotides 36303499 to 36304925 | 109 |
| ENSMUST00000195679 | NC_000001.11 truncated from nucleotides 55215407 to 55217455 | 110 |
| ENSMUST00000195679 | NC_000001.11 truncated from nucleotides 55217860 to 55234177 | 111 |

Hybridization

In some embodiments, hybridization occurs between a compound disclosed herein and a MaTAR nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Hybridization conditions are sequence-dependent and are determined by the nature and composition of the nucleic acid molecules to be hybridized.

Methods of determining whether a sequence is specifically hybridizable to a target nucleic acid are well known in the art. In certain embodiments, the compounds provided herein are specifically hybridizable with a MaTAR nucleic acid.

Complementarity

An oligonucleotide is said to be complementary to another nucleic acid when the nucleobase sequence of such oligonucleotide or one or more regions thereof matches the nucleobase sequence of another oligonucleotide or nucleic acid or one or more regions thereof when the two nucleobase sequences are aligned in opposing directions. Nucleobase matches or complementary nucleobases, as described herein, are limited to adenine (A) and thymine (T), adenine (A) and uracil (U), cytosine (C) and guanine (G), and 5-methyl cytosine (mC) and guanine (G) unless otherwise specified. Complementary oligonucleotides and/or nucleic acids need not have nucleobase complementarity at each nucleoside and may include one or more nucleobase mismatches. An oligonucleotide is fully complementary or 100% complementary when such oligonucleotides have nucleobase matches at each nucleoside without any nucleobase mismatches.

In certain embodiments, compounds described herein comprise or consist of modified oligonucleotides. In certain embodiments, compounds described herein are antisense compounds. In certain embodiments, compounds comprise oligomeric compounds. Non-complementary nucleobases between a compound and a MaTAR nucleic acid may be tolerated provided that the compound remains able to specifically hybridize to a target nucleic acid. Moreover, a compound may hybridize over one or more segments of a MaTAR nucleic acid such that intervening or adjacent segments are not involved in the hybridization event (e.g., a loop structure, mismatch or hairpin structure).

In certain embodiments, the compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a MaTAR nucleic acid, a target region, target segment, or specified portion thereof. Percent complementarity of a compound with a target nucleic acid can be determined using routine methods.

For example, a compound in which 18 of 20 nucleobases of the compound are complementary to a target region, and would therefore specifically hybridize, would represent 90 percent complementarity. In this example, the remaining non-complementary nucleobases may be clustered or interspersed with complementary nucleobases and need not be contiguous to each other or to complementary nucleobases. As such, a compound which is 18 nucleobases in length having four non-complementary nucleobases which are flanked by two regions of complete complementarity with the target nucleic acid would have 77.8% overall complementarity with the target nucleic acid and would thus fall within the scope of the present invention. Percent complementarity of a compound with a region of a target nucleic acid can be determined routinely using BLAST programs (basic local alignment search tools) and PowerBLAST programs known in the art (Altschul et al., *J. Mol. Biol.*, 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, compounds described herein, or specified portions thereof, are fully complementary (i.e. 100% complementary) to a target nucleic acid, or specified portion thereof. For example, a compound may be fully complementary to a MaTAR nucleic acid, or a target region, or a target segment or target sequence thereof. As used herein, "fully complementary" means each nucleobase of a compound is capable of precise base pairing with the corresponding nucleobases of a target nucleic acid. For example, a 20 nucleobase compound is fully complementary to a target sequence that is 400 nucleobases long, so long as there is a corresponding 20 nucleobase portion of the target nucleic acid that is fully complementary to the compound. Fully complementary can also be used in reference to a specified portion of the first and/or the second nucleic acid. For example, a 20 nucleobase portion of a 30 nucleobase compound can be "fully complementary" to a target sequence that is 400 nucleobases long. The 20 nucleobase portion of the 30 nucleobase compound is fully complementary to the target sequence if the target sequence has a corresponding 20 nucleobase portion wherein each nucleobase is complementary to the 20 nucleobase portion of the compound. At the same time, the entire 30 nucleobase compound may or may not be fully complementary to the target sequence, depending on whether the remaining 10 nucleobases of the compound are also complementary to the target sequence.

In certain embodiments, compounds described herein comprise one or more mismatched nucleobases relative to the target nucleic acid. In certain such embodiments, antisense activity against the target is reduced by such mismatch, but activity against a non-target is reduced by a greater amount. Thus, in certain such embodiments selectivity of the compound is improved. In certain embodiments, the mismatch is specifically positioned within an oligonucleotide having a gapmer motif. In certain such embodiments, the mismatch is at position 1, 2, 3, 4, 5, 6, 7, or 8 from the 5'-end of the gap region. In certain such embodiments, the mismatch is at position 9, 8, 7, 6, 5, 4, 3, 2, 1 from the 3'-end of the gap region. In certain such embodiments, the mismatch is at position 1, 2, 3, or 4 from the 5'-end of the wing region. In certain such embodiments, the mismatch is at position 4, 3, 2, or 1 from the 3'-end of the wing region. In certain embodiments, the mismatch is specifically positioned within an oligonucleotide not having a gapmer motif. In certain such embodiments, the mismatch is at position 1, 2, 3, 4, 5, 6, 7, 8, 9, 10, 11, or 12 from the 5'-end of the oligonucleotide. In certain such embodiments, the mismatch is at position, 2, 3, 4, 5, 6, 7, 8, 9, 10, 11, or 12 from the 3'-end of the oligonucleotide.

The location of a non-complementary nucleobase may be at the 5' end or 3' end of the compound. Alternatively, the non-complementary nucleobase or nucleobases may be at an internal position of the compound. When two or more non-complementary nucleobases are present, they may be contiguous (i.e. linked) or non-contiguous. In one embodiment, a non-complementary nucleobase is located in the wing segment of a gapmer oligonucleotide.

In certain embodiments, compounds described herein that are, or are up to 11, 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a MaTAR nucleic acid, or specified portion thereof.

In certain embodiments, compounds described herein that are, or are up to 11, 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a MaTAR nucleic acid, or specified portion thereof.

In certain embodiments, compounds described herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of a compound. In certain embodiments, the compounds, are complementary to at least an 8 nucleobase portion of a target segment. In certain embodiments, the compounds are complementary to at least a 9 nucleobase portion of a target segment. In certain embodiments, the compounds are complementary to at least a 10 nucleobase portion of a target segment. In certain embodiments, the compounds are complementary to at least an 11 nucleobase portion of a target segment. In certain embodiments, the compounds are complementary to at least a 12 nucleobase portion of a target segment. In certain embodiments, the compounds are complementary to at least a 13 nucleobase portion of a target segment. In certain embodiments, the compounds are complementary to at least a 14 nucleobase portion of a target segment. In certain embodiments, the compounds are complementary to at least a 15 nucleobase portion of a target segment. In certain embodiments, the compounds are complementary to at least a 16 nucleobase portion of a target segment. Also contemplated are compounds that are complementary to at least a 9, 10, 11, 12, 13, 14, 15, 16, 17, 18, 19, 20, or more nucleobase portion of a target segment, or a range defined by any two of these values.

Identity

The compounds provided herein may also have a defined percent identity to a particular nucleotide sequence, SEQ ID NO, or compound represented by a specific Isis number, or portion thereof. In certain embodiments, compounds described herein are antisense compounds or oligomeric compounds. In certain embodiments, compounds described herein are modified oligonucleotides. As used herein, a compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the compounds described herein as well as compounds having non-identical bases relative to the compounds provided herein also are contemplated. The non-identical bases may be adjacent to each other or dispersed throughout the compound. Percent identity of an compound is calculated according to the number of bases that have identical base pairing relative to the sequence to which it is being compared.

In certain embodiments, compounds described herein, or portions thereof, are, or are at least, 70%, 75%, 80%, 85%, 90%, 91%, 92%, 93%, 94%, 95%, 96%, 97%, 98%, 99% or 100% identical to one or more of the compounds or SEQ ID NOs, or a portion thereof, disclosed herein. In certain embodiments, compounds described herein are about 70%, 75%, 80%, 85%, 90%, 91%, 92%, 93%, 94%, 95%, 96%, 97%, 98%, or 99% identical, or any percentage between such values, to a particular nucleotide sequence, SEQ ID NO, or compound represented by a specific Isis number, or portion thereof, in which the compounds comprise an oligonucleotide having one or more mismatched nucleobases. In certain such embodiments, the mismatch is at position 1, 2, 3, 4, 5, 6, 7, 8, 9, 10, 11, or 12 from the 5'-end of the oligonucleotide. In certain such embodiments, the mismatch is at position, 2, 3, 4, 5, 6, 7, 8, 9, 10, 11, or 12 from the 3'-end of the oligonucleotide.

In certain embodiments, compounds described herein are antisense compounds. In certain embodiments, a portion of the compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, compounds described herein are oligonucleotides. In certain embodiments, a portion of the oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Certain Modified Compounds

In certain embodiments, compounds described herein comprise or consist of oligonucleotides consisting of linked nucleosides. Oligonucleotides may be unmodified oligonucleotides (RNA or DNA) or may be modified oligonucleotides. Modified oligonucleotides comprise at least one modification relative to unmodified RNA or DNA (i.e., comprise at least one modified nucleoside (comprising a modified sugar moiety and/or a modified nucleobase) and/or at least one modified internucleoside linkage).

A. Modified Nucleosides

Modified nucleosides comprise a modified sugar moiety or a modified nucleobase or both a modified sugar moiety and a modified nucleobase.

1. Modified Sugar Moieties

In certain embodiments, sugar moieties are non-bicyclic modified sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of other types of modified sugar moieties.

In certain embodiments, modified sugar moieties are non-bicyclic modified sugar moieties comprising a furanosyl ring with one or more acyclic substituent, including but not limited to substituents at the 2', 4', and/or 5' positions. In certain embodiments one or more acyclic substituent of non-bicyclic modified sugar moieties is branched. Examples of 2'-substituent groups suitable for non-bicyclic modified sugar moieties include but are not limited to: 2'-F, 2'-OCH$_3$ ("OMe" or "O-methyl"), and 2'-O(CH$_2$)$_2$OCH$_3$ ("MOE"). In certain embodiments, 2'-substituent groups are selected from among: halo, allyl, amino, azido, SH, CN, OCN, CF$_3$, OCF$_3$, alkoxy, O—C$_1$-C$_{10}$ substituted alkoxy, O—C$_1$-C$_{10}$ alkyl, O—C$_1$-C$_{10}$ substituted alkyl, S-alkyl, N(R$_m$)-alkyl, O-alkenyl, S-alkenyl, N(R$_m$)-alkenyl, O-alkynyl, S-alkynyl, N(R$_m$)-alkynyl, O-alkylenyl-O-alkyl, alkynyl, alkaryl, aralkyl, O-alkaryl, O-aralkyl, O(CH$_2$)$_2$SCH$_3$, O(CH$_2$)$_2$ON(R$_m$)(R$_n$) or OCH$_2$C(=O)—N(R$_m$)(R$_n$), where each R$_m$ and R$_n$ is, independently, H, an amino protecting group, or substituted or unsubstituted C$_1$-C$_{10}$ alkyl, and the 2'-substituent groups described in Cook et al., U.S. Pat. No. 6,531,584; Cook et al., U.S. Pat. No. 5,859,221; and Cook et al., U.S. Pat. No. 6,005,087. Certain embodiments of these 2'-substituent groups can be further substituted with one or more substituent groups independently selected from among: hydroxyl, amino, alkoxy, carboxy, benzyl, phenyl, nitro (NO$_2$), thiol, thioalkoxy, thioalkyl, halogen, alkyl, aryl, alkenyl and alkynyl. Examples of 4'-substituent groups suitable for linearlynon-bicyclic modified sugar moieties include but are not limited to alkoxy (e.g., methoxy), alkyl, and those described in Manoharan et al., WO 2015/106128. Examples of 5'-substituent groups suitable for non-bicyclic modified sugar moieties include but are not limited to: 5'-methyl (R or S), 5'-vinyl, and 5'-methoxy. In certain embodiments, non-bicyclic modified sugars comprise more than one non-bridging sugar substituent, for example, 2'-F-5'-methyl sugar moieties and the modified sugar moieties and modified nucleosides described in Migawa et al., WO 2008/101157 and Rajeev et al., US2013/0203836.

In certain embodiments, a 2'-substituted nucleoside or 2'-non-bicyclic modified nucleoside comprises a sugar moiety comprising a linear 2'-substituent group selected from: F, NH$_2$, N$_3$, OCF$_3$, OCH$_3$, O(CH$_2$)$_3$NH$_2$, CH$_2$CH=CH$_2$, OCH$_2$CH=CH$_2$, OCH$_2$CH$_2$OCH$_3$, O(CH$_2$)$_2$SCH$_3$, O(CH$_2$)$_2$ON(R$_m$)(R$_n$), O(CH$_2$)$_2$O(CH$_2$)$_2$N(CH$_3$)$_2$, and N-substituted acetamide (OCH$_2$C(=O)—N(R$_m$)(R$_n$)), where each R$_m$ and R$_n$ is, independently, H, an amino protecting group, or substituted or unsubstituted C$_1$-C$_{10}$ alkyl.

In certain embodiments, a 2'-substituted nucleoside or 2'-non-bicyclic modified nucleoside comprises a sugar moiety comprising a linear 2'-substituent group selected from: F, OCF$_3$, OCH$_3$, OCH$_2$CH$_2$OCH$_3$, O(CH$_2$)$_2$SCH$_3$, O(CH$_2$)$_2$ON(CH$_3$)$_2$, O(CH$_2$)$_2$O(CH$_2$)$_2$N(CH$_3$)$_2$, and OCH$_2$C(=O)—N(H)CH$_3$ ("NMA").

In certain embodiments, a 2'-substituted nucleoside or 2'-non-bicyclic modified nucleoside comprises a sugar moiety comprising a linear 2'-substituent group selected from: F, OCH$_3$, and OCH$_2$CH$_2$OCH$_3$.

Nucleosides comprising modified sugar moieties, such as non-bicyclic modified sugar moieties, are referred to by the position(s) of the substitution(s) on the sugar moiety of the nucleoside. For example, nucleosides comprising 2'-substituted or 2-modified sugar moieties are referred to as 2'-substituted nucleosides or 2-modified nucleosides.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' bridging sugar substituents include but are not limited to: 4'-CH$_2$-2', 4'-(CH$_2$)$_2$-2', 4'-(CH$_2$)$_3$-2', ("LNA"), 4'-CH$_2$—S-2', 4'-(CH$_2$)$_2$—O-2' ("ENA"), 4'-CH(CH$_3$)—O-2' (referred to as "constrained ethyl" or "cEt" when in the S configuration), 4'-CH$_2$—O—CH$_2$-2', 4'-CH$_2$—N(R)-2', 4'-CH(CH$_2$OCH$_3$)—O-2' ("constrained MOE" or "cMOE") and analogs thereof (see, e.g., Seth et al., U.S. Pat. No. 7,399,845, Bhat et al., U.S. Pat. No. 7,569,686, Swayze et al., U.S. 7,741,457, and Swayze et al., U.S. Pat. No. 8,022,193), 4'-C(CH$_3$)(CH$_3$)—O-2' and analogs thereof (see, e.g., Seth et al., U.S. Pat. No. 8,278,283), 4'-CH$_2$—N(OCH$_3$)-2' and analogs thereof (see, e.g., Prakash et al., U.S. Pat. No. 8,278,425), 4'-CH2-O—N(CH$_3$)-2' (see, e.g., Allerson et al., U.S. Pat. No. 7,696,345 and Allerson et al., U.S. Pat. No. 8,124,745), 4'-CH$_2$—C(H)(CH$_3$)-2' (see, e.g., Zhou, et al., *J. Org. Chem.*, 2009, 74, 118-134), 4'-CH$_2$—C(=CH$_2$)-2' and analogs thereof (see e.g., Seth et al., U.S. Pat. No. 8,278, 426), 4'-C(R$_a$R$_b$)—N(R)—O-2', 4'-C(R$_a$R$_b$)—O—N(R)-2', 4'-CH2-O—N(R)-2', and 4'-CH2-N(R)—O-2', wherein each R, R$_a$, and R$_b$ is, independently, H, a protecting group, or C$_1$-C$_{12}$ alkyl (see, e.g. Imanishi et al., U.S. Pat. No. 7,427, 672).

In certain embodiments, such 4' to 2' bridges independently comprise from 1 to 4 linked groups independently selected from: —[C(R$_a$)(R$_b$)]$_n$—, —[C(R$_a$)(R$_b$)]$_n$—O—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—;

wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl, or a protecting group.

Additional bicyclic sugar moieties are known in the art, see, for example: Freier et al., *Nucleic Acids Research*, 1997, 25(22), 4429-4443, Albaek et al., *J. Org. Chem.*, 2006, 71, 7731-7740, Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A.*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 20017, 129, 8362-8379; Elayadi et al., *Curr. Opinion Invens. Drugs*, 2001, 2, 558-561; Braasch et al., *Chem. Biol.*, 2001, 8, 1-7; Orum et al., *Curr. Opinion Mol. Ther.*, 2001, 3, 239-243; Wengel et al., U.S. Pat. No. 7,053,207, Imanishi et al., U.S. Pat. No. 6,268,490, Imanishi et al. U.S. Pat. No. 6,770,748, Imanishi et al., U.S. Pat. No. RE44,779; Wengel et al., U.S. Pat. No. 6,794,499, Wengel et al., U.S. Pat. No. 6,670,461; Wengel et al., U.S. Pat. No. 7,034,133, Wengel et al., U.S. Pat. No. 8,080,644; Wengel et al., U.S. Pat. No. 8,034,909; Wengel et al., U.S. Pat. No. 8,153,365; Wengel et al., U.S. Pat. No. 7,572,582; and Ramasamy et al., U.S. Pat. No. 6,525,191, Torsten et al., WO 2004/106356, Wengel et al., WO 91999/014226; Seth et al., WO 2007/134181; Seth et al., U.S. Pat. No. 7,547,684; Seth et al., U.S. Pat. No. 7,666,854; Seth et al., U.S. Pat. No. 8,088,746; Seth et al., U.S. Pat. No. 7,750,131; Seth et al., U.S. Pat. No. 8,030,467; Seth et al., U.S. Pat. No. 8,268,980; Seth et al., U.S. Pat. No. 8,546,556; Seth et al., U.S. Pat. No. 8,530,640; Migawa et al., U.S. Pat. No. 9,012,421; Seth et al., U.S. Pat. No. 8,501,805; and U.S. Patent Publication Nos. Allerson et al., US2008/0039618 and Migawa et al., US2015/0191727.

In certain embodiments, bicyclic sugar moieties and nucleosides incorporating such bicyclic sugar moieties are further defined by isomeric configuration. For example, an LNA nucleoside (described herein) may be in the α-L configuration or in the β-D configuration.

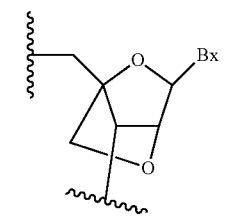

LNA (β-D-configuration)
bridge = 4'-CH$_2$—O-2'

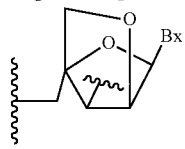

α-L-LNA (α-L-configuration)
bridge = 4'-CH$_2$—O-2'

α-L-methyleneoxy (4'-CH$_2$—O-2') or α-L-LNA bicyclic nucleosides have been incorporated into oligonucleotides that showed antisense activity (Frieden et al., *Nucleic Acids Research*, 2003, 21, 6365-6372). Herein, general descriptions of bicyclic nucleosides include both isomeric configurations. When the positions of specific bicyclic nucleosides (e.g., LNA or cEt) are identified in exemplified embodiments herein, they are in the β-D configuration, unless otherwise specified.

In certain embodiments, modified sugar moieties comprise one or more non-bridging sugar substituent and one or more bridging sugar substituent (e.g., 5'-substituted and 4'-2' bridged sugars).

In certain embodiments, modified sugar moieties are sugar surrogates. In certain such embodiments, the oxygen atom of the sugar moiety is replaced, e.g., with a sulfur, carbon or nitrogen atom. In certain such embodiments, such modified sugar moieties also comprise bridging and/or non-bridging substituents as described herein. For example, certain sugar surrogates comprise a 4'-sulfur atom and a substitution at the 2'-position (see, e.g., Bhat et al., U.S. Pat. No. 7,875,733 and Bhat et al., U.S. Pat. No. 7,939,677) and/or the 5' position.

In certain embodiments, sugar surrogates comprise rings having other than 5 atoms. For example, in certain embodiments, a sugar surrogate comprises a six-membered tetrahydropyran ("THP"). Such tetrahydropyrans may be further modified or substituted. Nucleosides comprising such modified tetrahydropyrans include but are not limited to hexitol nucleic acid ("HNA"), anitol nucleic acid ("ANA"), manitol nucleic acid ("MNA") (see e.g., Leumann, C J. *Bioorg. & Med. Chem.* 2002, 10, 841-854), fluoro HNA:

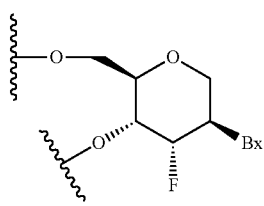

F-HNA ("F-HNA", see e.g., Swayze et al., U.S. Pat. No. 8,088,904; Swayze et al., U.S. Pat. No. 8,440,803; Swayze et al., U.S.; and Swayze et al., U.S. Pat. No. 9,005,906, F-HNA can also be referred to as a F-THP or 3'-fluoro tetrahydropyran), and nucleosides comprising additional modified THP compounds having the formula:

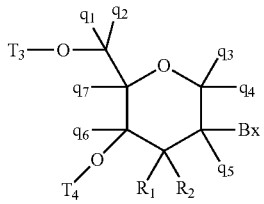

wherein, independently, for each of said modified THP nucleoside: Bx is a nucleobase moiety; $T_3$ and $T_4$ are each, independently, an internucleoside linking group linking the modified THP nucleoside to the remainder of an oligonucleotide or one of $T_3$ and $T_4$ is an internucleoside linking group linking the modified THP nucleoside to the remainder of an oligonucleotide and the other of $T_3$ and $T_4$ is H, a hydroxyl protecting group, a linked conjugate group, or a 5' or 3'-terminal group; $q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, modified THP nucleosides are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, modified THP nucleosides are provided wherein one of $R_1$ and $R_2$ is F. In certain embodiments, $R_1$ is F and $R_2$ is H, in certain embodiments, $R_1$ is methoxy and $R_2$ is H, and in certain embodiments, $R_1$ is methoxyethoxy and $R_2$ is H.

In certain embodiments, sugar surrogates comprise rings having more than 5 atoms and more than one heteroatom. For example, nucleosides comprising morpholino sugar moieties and their use in oligonucleotides have been reported (see, e.g., Braasch et al., Biochemistry, 2002, 41, 4503-4510 and Summerton et al., U.S. Pat. No. 5,698,685; Summerton et al., U.S. Pat. No. 5,166,315; Summerton et al., U.S. Pat. No. 5,185,444; and Summerton et al., U.S. Pat. No. 5,034,506). As used here, the term "morpholino" means a sugar surrogate having the following structure:

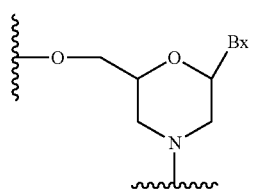

In certain embodiments, morpholinos may be modified, for example by adding or altering various substituent groups from the above morpholino structure. Such sugar surrogates are referred to herein as "modified morpholinos."

In certain embodiments, sugar surrogates comprise acyclic moieties. Examples of nucleosides and oligonucleotides comprising such acyclic sugar surrogates include but are not limited to: peptide nucleic acid ("PNA"), acyclic butyl nucleic acid (see, e.g., Kumar et al., Org. Biomol. Chem., 2013, 11, 5853-5865), and nucleosides and oligonucleotides described in Manoharan et al., WO2011/133876.

Many other bicyclic and tricyclic sugar and sugar surrogate ring systems are known in the art that can be used in modified nucleosides.

2. Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications can impart nuclease stability, binding affinity or some other beneficial biological property to compounds described herein.

In certain embodiments, compounds described herein comprise modified oligonucleotides. In certain embodiments, modified oligonucleotides comprise one or more nucleoside comprising an unmodified nucleobase. In certain embodiments, modified oligonucleotides comprise one or more nucleoside comprising a modified nucleobase. In certain embodiments, modified oligonucleotides comprise one or more nucleoside that does not comprise a nucleobase, referred to as an abasic nucleoside.

In certain embodiments, modified nucleobases are selected from: 5-substituted pyrimidines, 6-azapyrimidines, alkyl or alkynyl substituted pyrimidines, alkyl substituted purines, and N-2, N-6 and O-6 substituted purines. In certain embodiments, modified nucleobases are selected from: 2-aminopropyladenine, 5-hydroxymethyl cytosine, 5-methylcytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl (C≡C—CH3) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in Merigan et al., U.S. Pat. No. 3,687,808, those disclosed in The Concise Encyclopedia Of Polymer Science And Engineering, Kroschwitz, J. I., Ed., John Wiley & Sons, 1990, 858-859; Englisch et al., Angewandte Chemie, International Edition, 1991, 30, 613; Sanghvi, Y. S., Chapter 15, Antisense Research and Applications, Crooke, S. T. and Lebleu, B., Eds., CRC Press, 1993, 273-288; and those disclosed in Chapters 6 and 15, Antisense Drug Technology, Crooke S. T., Ed., CRC Press, 2008, 163-166 and 442-443.

Publications that teach the preparation of certain of the above noted modified nucleobases as well as other modified nucleobases include without limitation, Manoharan et al., US2003/0158403, Manoharan et al., US2003/0175906; Dinh et al., U.S. Pat. No. 4,845,205; Spielvogel et al., U.S. Pat. No. 5,130,302; Rogers et al., U.S. Pat. No. 5,134,066; Bischofberger et al., U.S. Pat. No. 5,175,273; Urdea et al., U.S. Pat. No. 5,367,066; Benner et al., U.S. Pat. No. 5,432,272; Matteucci et al., U.S. Pat. No. 5,434,257; Gmeiner et al., U.S. Pat. No. 5,457,187; Cook et al., U.S. Pat. No. 5,459,255; Froehler et al., U.S. Pat. No. 5,484,908; Matteucci et al., U.S. Pat. No. 5,502,177; Hawkins et al., U.S. Pat. No. 5,525,711; Haralambidis et al., U.S. 5,552,540; Cook et al., U.S. Pat. No. 5,587,469; Froehler et al., U.S. Pat. No. 5,594,121; Switzer et al., U.S. Pat. No. 5,596,091; Cook et al., U.S. Pat. No. 5,614,617; Froehler et al., U.S. Pat. No. 5,645,985; Cook et al., U.S. Pat. No. 5,681,941; Cook et al., U.S. Pat. No. 5,811,534; Cook et al., U.S. Pat. No. 5,750,692; Cook et al., U.S. Pat. No. 5,948,903; Cook et al., U.S. Pat. No. 5,587,470; Cook et al., U.S. Pat. No. 5,457,191; Matteucci et al., U.S. Pat. No. 5,763,588; Froehler et al., U.S. Pat. No. 5,830,653; Cook et al., U.S. Pat. No. 5,808,027; Cook et al., 6,166,199; and Matteucci et al., U.S. Pat. No. 6,005,096.

In certain embodiments, compounds targeted to a MaTAR nucleic acid comprise one or more modified nucleobases. In certain embodiments, the modified nucleobase is 5-methylcytosine. In certain embodiments, each cytosine is a 5-methylcytosine.

Modified Internucleoside Linkages

The naturally occurring internucleoside linkage of RNA and DNA is a 3' to 5' phosphodiester linkage. In certain embodiments, compounds described herein having one or more modified, i.e. non-naturally occurring, internucleoside linkages are often selected over compounds having naturally occurring internucleoside linkages because of desirable properties such as, for example, enhanced cellular uptake, enhanced affinity for target nucleic acids, and increased stability in the presence of nucleases.

In certain embodiments, compounds targeted to a MaTAR nucleic acid comprise one or more modified internucleoside linkages. In certain embodiments, the modified internucleoside linkages are phosphorothioate linkages. In certain embodiments, each internucleoside linkage of the compound is a phosphorothioate internucleoside linkage.

In certain embodiments, compounds described herein comprise oligonucleotides. Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, nucleosides of modified oligonucleotides may be linked together using any internucleoside linkage. The two main classes of internucleoside linking groups are defined by the presence or absence of a phosphorus atom. Representative phosphorus-containing internucleoside linkages include but are not limited to phosphates, which contain a phosphodiester bond ("P=O") (also referred to as unmodified or naturally occurring linkages), phosphotriesters, methylphosphonates, phosphoramidates, and phosphorothioates ("P=S"), and phosphorodithioates ("HS—P=S"). Representative non-phosphorus containing internucleoside linking groups include but are not limited to methylenemethylimino (—CH2-N(CH3)-O—CH2-), thiodiester, thionocarbamate (—O—C(=O)(NH)—S—); siloxane (—O—SiH2-O—); and N,N'-dimethylhydrazine (—CH2-N(CH3)-N(CH3)-). Modified internucleoside linkages, compared to naturally occurring phosphate linkages, can be used to alter, typically increase, nuclease resistance of the oligonucleotide. In certain embodiments, internucleoside linkages having a chiral atom can be prepared as a racemic mixture, or as separate enantiomers. Representative chiral internucleoside linkages include but are not limited to alkylphosphonates and phosphorothioates. Methods of preparation of phosphorous-containing and non-phosphorous-containing internucleoside linkages are well known to those skilled in the art.

Neutral internucleoside linkages include, without limitation, phosphotriesters, methylphosphonates, MMI (3'-CH2-N(CH3)-O-5'), amide-3 (3'-CH2-C(=O)—N(H)-5'), amide-4 (3'-CH2-N(H)—C(=O)-5'), formacetal (3'-O—CH2-O-5'), methoxypropyl, and thioformacetal (3'-S—CH2-O-5'). Further neutral internucleoside linkages include nonionic linkages comprising siloxane (dialkylsiloxane), carboxylate ester, carboxamide, sulfide, sulfonate ester and amides (See for example: Carbohydrate Modifications in Antisense Research; Y. S. Sanghvi and P. D. Cook, Eds., ACS Symposium Series 580; Chapters 3 and 4, 40-65). Further neutral internucleoside linkages include nonionic linkages comprising mixed N, O, S and CH2 component parts.

In certain embodiments, oligonucleotides comprise modified internucleoside linkages arranged along the oligonucleotide or region thereof in a defined pattern or modified internucleoside linkage motif. In certain embodiments, internucleoside linkages are arranged in a gapped motif. In such embodiments, the internucleoside linkages in each of two wing regions are different from the internucleoside linkages in the gap region. In certain embodiments the internucleoside linkages in the wings are phosphodiester and the internucleoside linkages in the gap are phosphorothioate. The nucleoside motif is independently selected, so such oligonucleotides having a gapped internucleoside linkage motif may or may not have a gapped nucleoside motif and if it does have a gapped nucleoside motif, the wing and gap lengths may or may not be the same.

In certain embodiments, oligonucleotides comprise a region having an alternating internucleoside linkage motif. In certain embodiments, oligonucleotides of the present invention comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

In certain embodiments, oligonucleotides comprise one or more methylphosponate linkages. In certain embodiments, oligonucleotides having a gapmer nucleoside motif comprise a linkage motif comprising all phosphorothioate linkages except for one or two methylphosponate linkages. In certain embodiments, one methylphosponate linkage is in the central gap of an oligonucleotide having a gapmer nucleoside motif.

In certain embodiments, it is desirable to arrange the number of phosphorothioate internucleoside linkages and phosphodiester internucleoside linkages to maintain nuclease resistance. In certain embodiments, it is desirable to arrange the number and position of phosphorothioate internucleoside linkages and the number and position of phosphodiester internucleoside linkages to maintain nuclease resistance. In certain embodiments, the number of phosphorothioate internucleoside linkages may be decreased and the number of phosphodiester internucleoside linkages may be increased. In certain embodiments, the number of phosphorothioate internucleoside linkages may be decreased and the number of phosphodiester internucleoside linkages may be increased while still maintaining nuclease resistance. In certain embodiments it is desirable to decrease the number of phosphorothioate internucleoside linkages while retaining nuclease resistance. In certain embodiments it is desirable to increase the number of phosphodiester internucleoside linkages while retaining nuclease resistance.

B. Certain Motifs

In certain embodiments, compounds described herein comprise oligonucleotides. Oligonucleotides can have a motif, e.g. a pattern of unmodified and/or modified sugar moieties, nucleobases, and/or internucleoside linkages. In certain embodiments, modified oligonucleotides comprise one or more modified nucleoside comprising a modified sugar. In certain embodiments, modified oligonucleotides comprise one or more modified nucleosides comprising a modified nucleobase. In certain embodiments, modified oligonucleotides comprise one or more modified internucleoside linkage. In such embodiments, the modified, unmodified, and differently modified sugar moieties, nucleobases, and/or internucleoside linkages of a modified oligonucleotide define a pattern or motif. In certain embodiments, the patterns of sugar moieties, nucleobases, and internucleoside linkages are each independent of one another. Thus, a modified oligonucleotide may be described by its sugar motif, nucleobase motif and/or internucleoside linkage motif (as used herein, nucleobase motif describes the modifications to the nucleobases independent of the sequence of nucleobases).

1. Certain Sugar Motifs

In certain embodiments, compounds described herein comprise oligonucleotides. In certain embodiments, oligonucleotides comprise one or more type of modified sugar and/or unmodified sugar moiety arranged along the oligonucleotide or region thereof in a defined pattern or sugar motif. In certain instances, such sugar motifs include but are not limited to any of the sugar modifications discussed herein.

In certain embodiments, modified oligonucleotides comprise or consist of a region having a gapmer motif, which comprises two external regions or "wings" and a central or internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap (i.e., the wing/gap junction). In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric gapmer). In certain embodiments, the sugar motif of the 5'-wing differs from the sugar motif of the 3¹-wing (asymmetric gapmer).

In certain embodiments, the wings of a gapmer comprise 1-5 nucleosides. In certain embodiments, the wings of a gapmer comprise 2-5 nucleosides. In certain embodiments, the wings of a gapmer comprise 3-5 nucleosides. In certain embodiments, the nucleosides of a gapmer are all modified nucleosides.

In certain embodiments, the gap of a gapmer comprises 7-12 nucleosides. In certain embodiments, the gap of a gapmer comprises 7-10 nucleosides. In certain embodiments, the gap of a gapmer comprises 8-10 nucleosides. In certain embodiments, the gap of a gapmer comprises 10 nucleosides. In certain embodiment, each nucleoside of the gap of a gapmer is an unmodified 2'-deoxy nucleoside.

In certain embodiments, the gapmer is a deoxy gapmer. In such embodiments, the nucleosides on the gap side of each wing/gap junction are unmodified 2'-deoxy nucleosides and the nucleosides on the wing sides of each wing/gap junction are modified nucleosides. In certain such embodiments, each nucleoside of the gap is an unmodified 2'-deoxy nucleoside. In certain such embodiments, each nucleoside of each wing is a modified nucleoside.

In certain embodiments, a modified oligonucleotide has a fully modified sugar motif wherein each nucleoside of the modified oligonucleotide comprises a modified sugar moiety. In certain embodiments, modified oligonucleotides comprise or consist of a region having a fully modified sugar motif wherein each nucleoside of the region comprises a modified sugar moiety. In certain embodiments, modified oligonucleotides comprise or consist of a region having a fully modified sugar motif, wherein each nucleoside within the fully modified region comprises the same modified sugar moiety, referred to herein as a uniformly modified sugar motif. In certain embodiments, a fully modified oligonucleotide is a uniformly modified oligonucleotide. In certain embodiments, each nucleoside of a uniformly modified comprises the same 2'-modification.

2. Certain Nucleobase Motifs In certain embodiments, compounds described herein comprise oligonucleotides. In certain embodiments, oligonucleotides comprise modified and/or unmodified nucleobases arranged along the oligonucleotide or region thereof in a defined pattern or motif. In certain embodiments, each nucleobase is modified. In certain embodiments, none of the nucleobases are modified. In certain embodiments, each purine or each pyrimidine is modified. In certain embodiments, each adenine is modified. In certain embodiments, each guanine is modified. In certain embodiments, each thymine is modified. In certain embodiments, each uracil is modified. In certain embodiments, each cytosine is modified. In certain embodiments, some or all of the cytosine nucleobases in a modified oligonucleotide are 5-methylcytosines.

In certain embodiments, modified oligonucleotides comprise a block of modified nucleobases. In certain such embodiments, the block is at the 3'-end of the oligonucleotide. In certain embodiments the block is within 3 nucleosides of the 3'-end of the oligonucleotide. In certain embodiments, the block is at the 5'-end of the oligonucleotide. In certain embodiments the block is within 3 nucleosides of the 5'-end of the oligonucleotide.

In certain embodiments, oligonucleotides having a gapmer motif comprise a nucleoside comprising a modified nucleobase. In certain such embodiments, one nucleoside comprising a modified nucleobase is in the central gap of an oligonucleotide having a gapmer motif. In certain such embodiments, the sugar moiety of said nucleoside is a 2'-deoxyribosyl moiety. In certain embodiments, the modified nucleobase is selected from: a 2-thiopyrimidine and a 5-propynepyrimidine.

3. Certain Internucleoside Linkage Motifs

In certain embodiments, compounds described herein comprise oligonucleotides. In certain embodiments, oligonucleotides comprise modified and/or unmodified internucleoside linkages arranged along the oligonucleotide or region thereof in a defined pattern or motif. In certain embodiments, essentially each internucleoside linking group is a phosphate internucleoside linkage (P=O). In certain embodiments, each internucleoside linking group of a modified oligonucleotide is a phosphorothioate (P=S). In certain embodiments, each internucleoside linking group of a modified oligonucleotide is independently selected from a phosphorothioate and phosphate internucleoside linkage. In certain embodiments, the sugar motif of a modified oligonucleotide is a gapmer and the internucleoside linkages within the gap are all modified. In certain such embodiments, some or all of the internucleoside linkages in the wings are unmodified phosphate linkages. In certain embodiments, the terminal internucleoside linkages are modified.

C. Certain Modified Oligonucleotides

In certain embodiments, compounds described herein comprise modified oligonucleotides. In certain embodiments, the above modifications (sugar, nucleobase, internucleoside linkage) are incorporated into a modified oligonucleotide. In certain embodiments, modified oligonucleotides are characterized by their modification, motifs, and overall lengths. In certain embodiments, such parameters are each independent of one another. Thus, unless otherwise indicated, each internucleoside linkage of an oligonucleotide having a gapmer sugar motif may be modified or unmodified and may or may not follow the gapmer modification pattern of the sugar modifications. For example, the internucleoside linkages within the wing regions of a sugar gapmer may be the same or different from one another and may be the same or different from the internucleoside linkages of the gap region of the sugar motif. Likewise, such gapmer oligonucleotides may comprise one or more modified nucleobase independent of the gapmer pattern of the sugar modifications. Furthermore, in certain instances, an oligonucleotide is described by an overall length or range and by lengths or length ranges of two or more regions (e.g., a regions of nucleosides having specified sugar modifications), in such circumstances it may be possible to select numbers for each range that result in an oligonucleotide having an overall length falling outside the specified range. In such circumstances, both elements must be satisfied. For example, in certain embodiments, a modified oligonucleotide consists of 15-20 linked nucleosides and has a sugar motif consisting of three regions, A, B, and C, wherein region A consists of 2-6 linked nucleosides having a specified sugar motif, region B consists of 6-10 linked nucleosides having a specified sugar motif, and region C consists of 2-6 linked nucleosides having a specified sugar motif. Such embodiments do not include modified oligonucleotides where A and C each consist of 6 linked nucleosides and B consists of 10 linked nucleosides (even though those numbers of nucleosides are permitted within the requirements for A, B, and C) because the overall length of such oligonucleotide is 22, which exceeds the upper limit of the overall length of the modified oligonucleotide (20). Herein, if a description of an oligonucleotide is silent with respect to one or more parameter, such parameter is not limited. Thus, a modified oligonucleotide described only as having a gapmer sugar motif without further description may have any length, internucleoside linkage motif, and nucleobase motif. Unless otherwise indicated, all modifications are independent of nucleobase sequence.

Certain Conjugated Compounds

In certain embodiments, the compounds described herein comprise or consist of an oligonucleotide (modified or unmodified) and optionally one or more conjugate groups and/or terminal groups. Conjugate groups consist of one or more conjugate moiety and a conjugate linker which links the conjugate moiety to the oligonucleotide. Conjugate groups may be attached to either or both ends of an oligonucleotide and/or at any internal position. In certain embodiments, conjugate groups are attached to the 2'-position of a nucleoside of a modified oligonucleotide. In certain embodiments, conjugate groups that are attached to either or both ends of an oligonucleotide are terminal groups. In certain such embodiments, conjugate groups or terminal groups are attached at the 3' and/or 5'-end of oligonucleotides. In certain such embodiments, conjugate groups (or terminal groups) are attached at the 3'-end of oligonucleotides. In certain embodiments, conjugate groups are attached near the 3'-end of oligonucleotides. In certain embodiments, conjugate groups (or terminal groups) are attached at the 5'-end of oligonucleotides. In certain embodiments, conjugate groups are attached near the 5'-end of oligonucleotides.

In certain embodiments, the oligonucleotide of a compound is modified. In certain embodiments, the oligonucleotide of a compound may have any nucleobase sequence. In certain embodiments, the oligonucleotide of a compound has a nucleobase sequence that is complementary to a target nucleic acid. In certain embodiments, oligonucleotides are complementary to a messenger RNA (mRNA). In certain embodiments, oligonucleotides are complementary to a sense transcript. In certain embodiments, oligonucleotides are complementary to a long non-coding RNA (lncRNA).

Examples of terminal groups include but are not limited to conjugate groups, capping groups, phosphate moieties, protecting groups, modified or unmodified nucleosides, and two or more nucleosides that are independently modified or unmodified.

A. Certain Conjugate Groups

In certain embodiments, oligonucleotides are covalently attached to one or more conjugate groups. In certain embodiments, conjugate groups modify one or more properties of the attached oligonucleotide, including but not limited to pharmacodynamics, pharmacokinetics, stability, binding, absorption, tissue distribution, cellular distribution, cellular uptake, charge and clearance. In certain embodiments, conjugate groups impart a new property on the attached oligonucleotide, e.g., fluorophores or reporter groups that enable detection of the oligonucleotide.

Certain conjugate groups and conjugate moieties have been described previously, for example: cholesterol moiety (Letsinger et al., *Proc. Natl. Acad. Sci. USA,* 1989, 86, 6553-6556), cholic acid (Manoharan et al., *Bioorg. Med. Chem. Lett.,* 1994, 4, 1053-1060), a thioether, e.g., hexyl-S-tritylthiol (Manoharan et al., *Ann. N.Y. Acad. Sci.,* 1992, 660, 306-309; Manoharan et al., *Bioorg. Med. Chem. Lett.,* 1993, 3, 2765-2770), a thiocholesterol (Oberhauser et al., *Nucl. Acids Res.,* 1992, 20, 533-538), an aliphatic chain, e.g., do-decan-diol or undecyl residues (Saison-Behmoaras et al., *EMBO J.,* 1991, 10, 1111-1118; Kabanov et al., *FEBS Lett.,* 1990, 259, 327-330; Svinarchuk et al., *Biochimie,* 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.,* 1995, 36, 3651-3654; Shea et al., *Nucl. Acids Res.,* 1990, 18, 3777-3783), a polyamine or a polyethylene glycol chain (Manoharan et al., *Nucleosides & Nucleotides,* 1995, 14, 969-973), or adamantane acetic acid, a palmityl moiety (Mishra et al., *Biochim. Biophys. Acta,* 1995, 1264, 229-237), an octadecylamine or hexylamino-carbonyl-oxycholesterol moiety (Crooke et al., *J. Pharmacol. Exp. Ther.,* 1996, 277, 923-937), a tocopherol group (Nishina et al., *Molecular Therapy Nucleic Acids,* 2015, 4, e220; doi:10.1038/mtna.2014.72 and Nishina et al., *Molecular Therapy,* 2008, 16, 734-740), or a GalNAc cluster (e.g., WO2014/179620).

1. Conjugate Moieties

Conjugate moieties include, without limitation, intercalators, reporter molecules, polyamines, polyamides, peptides, carbohydrates (e.g., GalNAc), vitamin moieties, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins, fluorophores, and dyes.

In certain embodiments, a conjugate moiety comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, fingolimod, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

2. Conjugate Linkers

Conjugate moieties are attached to oligonucleotides through conjugate linkers. In certain compounds, a conjugate group is a single chemical bond (i.e. conjugate moiety is attached to an oligonucleotide via a conjugate linker through a single bond). In certain embodiments, the conjugate linker comprises a chain structure, such as a hydrocarbyl chain, or an oligomer of repeating units such as ethylene glycol, nucleosides, or amino acid units.

In certain embodiments, a conjugate linker comprises one or more groups selected from alkyl, amino, oxo, amide, disulfide, polyethylene glycol, ether, thioether, and hydroxylamino. In certain such embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus moiety. In certain embodiments, the conjugate linker comprises at least one phosphate group. In certain embodiments, the conjugate linker includes at least one neutral linking group.

In certain embodiments, conjugate linkers, including the conjugate linkers described above, are bifunctional linking moieties, e.g., those known in the art to be useful for attaching conjugate groups to parent compounds, such as the oligonucleotides provided herein. In general, a bifunctional linking moiety comprises at least two functional groups. One of the functional groups is selected to bind to a particular site on a compound and the other is selected to bind to a conjugate group. Examples of functional groups used in a bifunctional linking moiety include but are not limited to electrophiles for reacting with nucleophilic groups and nucleophiles for reacting with electrophilic groups. In certain embodiments, bifunctional linking moieties comprise one or more groups selected from amino, hydroxyl, carboxylic acid, thiol, alkyl, alkenyl, and alkynyl.

Examples of conjugate linkers include but are not limited to pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other conjugate linkers include but are not limited to substituted or unsubstituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, conjugate linkers comprise 1-10 linker-nucleosides. In certain embodiments, such linker-nucleosides are modified nucleosides. In certain embodiments such linker-nucleosides comprise a modified sugar moiety. In certain embodiments, linker-nucleosides are unmodified. In certain embodiments, linker-nucleosides comprise an optionally protected heterocyclic base selected from a purine, substituted purine, pyrimidine or substituted pyrimidine. In certain embodiments, a cleavable moiety is a nucleoside selected from uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine. It is typically desirable for linker-nucleosides to be cleaved from the compound after it reaches a target tissue. Accordingly, linker-nucleosides are typically linked to one another and to the remainder of the compound through cleavable bonds. In certain embodiments, such cleavable bonds are phosphodiester bonds.

Herein, linker-nucleosides are not considered to be part of the oligonucleotide. Accordingly, in embodiments in which a compound comprises an oligonucleotide consisting of a specified number or range of linked nucleosides and/or a specified percent complementarity to a reference nucleic acid and the compound also comprises a conjugate group comprising a conjugate linker comprising linker-nucleosides, those linker-nucleosides are not counted toward the length of the oligonucleotide and are not used in determining the percent complementarity of the oligonucleotide for the reference nucleic acid. For example, a compound may comprise (1) a modified oligonucleotide consisting of 8-30 nucleosides and (2) a conjugate group comprising 1-10 linker-nucleosides that are contiguous with the nucleosides of the modified oligonucleotide. The total number of contiguous linked nucleosides in such a compound is more than 30. Alternatively, an compound may comprise a modified oligonucleotide consisting of 8-30 nucleosides and no conjugate group. The total number of contiguous linked nucleosides in such a compound is no more than 30. Unless otherwise indicated conjugate linkers comprise no more than 10 linker-nucleosides. In certain embodiments, conjugate linkers comprise no more than 5 linker-nucleosides. In certain embodiments, conjugate linkers comprise no more than 3 linker-nucleosides. In certain embodiments, conjugate linkers comprise no more than 2 linker-nucleosides. In certain embodiments, conjugate linkers comprise no more than 1 linker-nucleoside.

In certain embodiments, it is desirable for a conjugate group to be cleaved from the oligonucleotide. For example, in certain circumstances compounds comprising a particular conjugate moiety are better taken up by a particular cell type, but once the compound has been taken up, it is desirable that the conjugate group be cleaved to release the unconjugated or parent oligonucleotide. Thus, certain conjugate may comprise one or more cleavable moieties, typically within the conjugate linker. In certain embodiments, a cleavable moiety is a cleavable bond. In certain embodiments, a cleavable moiety is a group of atoms comprising at least one cleavable bond. In certain embodiments, a cleavable moiety comprises a group of atoms having one, two, three, four, or more than four cleavable bonds. In certain embodiments, a cleavable moiety is selectively cleaved inside a cell or subcellular compartment, such as a lysosome. In certain embodiments, a cleavable moiety is selectively cleaved by endogenous enzymes, such as nucleases.

In certain embodiments, a cleavable bond is selected from among: an amide, an ester, an ether, one or both esters of a phosphodiester, a phosphate ester, a carbamate, or a disulfide. In certain embodiments, a cleavable bond is one or both of the esters of a phosphodiester. In certain embodiments, a cleavable moiety comprises a phosphate or phosphodiester. In certain embodiments, the cleavable moiety is a phosphate linkage between an oligonucleotide and a conjugate moiety or conjugate group.

In certain embodiments, a cleavable moiety comprises or consists of one or more linker-nucleosides. In certain such embodiments, one or more linker-nucleosides are linked to one another and/or to the remainder of the compound through cleavable bonds. In certain embodiments, such cleavable bonds are unmodified phosphodiester bonds. In certain embodiments, a cleavable moiety is 2'-deoxy nucleoside that is attached to either the 3' or 5'-terminal nucleoside of an oligonucleotide by a phosphate internucleoside linkage and covalently attached to the remainder of the conjugate linker or conjugate moiety by a phosphate or phosphorothioate linkage. In certain such embodiments, the cleavable moiety is 2'-deoxyadenosine.

Compositions and Methods for Formulating Pharmaceutical Compositions

Compounds described herein may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

In certain embodiments, the present invention provides pharmaceutical compositions comprising one or more compounds or a salt thereof. In certain embodiments, the compounds are antisense compounds or oligomeric compounds. In certain embodiments, the compounds comprise or consist of a modified oligonucleotide. In certain such embodiments, the pharmaceutical composition comprises a suitable pharmaceutically acceptable diluent or carrier. In certain embodiments, a pharmaceutical composition comprises a sterile saline solution and one or more compound. In certain embodiments, such pharmaceutical composition consists of a sterile saline solution and one or more compound. In certain embodiments, the sterile saline is pharmaceutical grade saline. In certain embodiments, a pharmaceutical composition comprises one or more compound and sterile water. In certain embodiments, a pharmaceutical composition consists of one compound and sterile water. In certain embodiments, the sterile water is pharmaceutical grade water. In certain embodiments, a pharmaceutical composition comprises one or more compound and phosphate-buffered saline (PBS). In certain embodiments, a pharmaceutical composition consists of one or more compound and sterile PBS. In certain embodiments, the sterile PBS is pharmaceutical grade PBS. Compositions and methods for the formulation of pharmaceutical compositions are dependent upon a number of criteria, including, but not limited to, route of administration, extent of disease, or dose to be administered.

A compound described herein targeted to a MaTAR nucleic acid can be utilized in pharmaceutical compositions by combining the compound with a suitable pharmaceutically acceptable diluent or carrier. In certain embodiments, a pharmaceutically acceptable diluent is water, such as sterile water suitable for injection. Accordingly, in one embodiment, employed in the methods described herein is a pharmaceutical composition comprising a compound targeted to a MaTAR nucleic acid and a pharmaceutically acceptable diluent. In certain embodiments, the pharmaceutically acceptable diluent is water. In certain embodiments, the compound comprises or consists of a modified oligonucleotide provided herein.

Pharmaceutical compositions comprising compounds provided herein encompass any pharmaceutically acceptable salts, esters, or salts of such esters, or any other oligonucleotide which, upon administration to an animal, including a human, is capable of providing (directly or indirectly) the biologically active metabolite or residue thereof. In certain embodiments, the compounds are antisense compounds or oligomeric compounds. In certain embodiments, the compound comprises or consists of a modified oligonucleotide. Accordingly, for example, the disclosure is also drawn to pharmaceutically acceptable salts of compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of a compound which are cleaved by endogenous nucleases within the body, to form the active compound.

In certain embodiments, the compounds or compositions further comprise a pharmaceutically acceptable carrier or diluent.

RNA-Sequencing

Total RNA was isolated either directly from cryosections of the tumor tissue or from organotypic epithelial cultures using TRIzol (Life Technologies) according to the manufacturer's instructions. For tissue sections, the tumors were embedded in OCT and cryosectioned. Sections from the middle of the tumor were stained using toluidine blue (Sigma) and assayed regarding the homogeneity of the section. Homogenous 30 μm sections comprising >90% malignant cells were immediately dispersed and homogenized in TRIzol. RNA quality was assayed by running an RNA 6000 Nano chip on a 2100 Bioanalyzer (Agilent). For high-throughput sequencing, RNA samples were required to have an RNA integrity number (RIN) ≥9. TruSeq (Illumina) libraries for polyA+RNA-Seq were prepared from 0.5-1 μg RNA per sample. To ensure efficient cluster generation, an additional gel purification step of the libraries was applied. The libraries were multiplexed (4-6 libraries per lane) and sequenced paired-end 101 bp on the HiSeq2000 platform (Illumina), resulting in on average 40 Mio reads per library.

Computational Analysis

The quality of the raw data was evaluated using FastQC (http://www.bioinformatics.babraham.ac.uk/projects/fastqc/), and reads were mapped to mm10 using STAR v2.4.1 (Dobin et al. Bioinformatics 29: 15-21, 2012), resulting in an overall mapping efficiency of >90%. The GENCODE mV5 GTF was used as a reference and the reads per gene record were counted using the HTSeq package v0.5.4p5 (Anders et al. Bioinformatics 31: 166-169, 2015) and parameters -m union -s no. Differential gene expression was performed with DESeq2 v1.8.1 (Love et al. Genome Biol. 15: 550, 2014). An adjusted p-value of <0.1 was set as threshold for statistical significance of differential gene expression. Functional analysis of KEGG pathways was carried out using the R/Bioconductor packages GAGE (Luo et al. BMC Bioinformatics 10: 161, 2009) and Pathview (Luo and Brouwer, Bioinformatics 29: 1830-1831, 2013). Gene set enrichment analysis was performed using the javaGSEA desktop application (Subramanian et al. 2005). Gene ontology (GO) analysis was carried out using GOrilla (Eden et al. BMC Bioinformatics 10: 48, 2009) separately on genes up- or down-regulated compared to normal mammary gland organoids.

Weighted Gene Coexpression Network Analysis

Weighted gene coexpression network analysis (WGCNA) was carried out as described previously (Bergmann et al. Genome Res. 2015). Briefly, ENCODE data sets (CSHL long RNA sequencing), ESC data as well as the tumor and organoid RNA-Seq datasets were used as input. We performed variance-stabilizing transformation of HTSeq-generated counts and averaged the counts from replicate samples. The WGCNA R package (Langfelder and Horvath BMC Bioinformatics 9: 559, 2008) was used with a value of β=5 as empirically chosen soft-threshold. This analysis identified 39 modules with a median gene number of 274.

Identification of Human MaTAR Counterparts

To identify human counterparts of MaTARs, mouse and human transcripts were compared on the level of both sequence conservation and genomic location.

First, the mouse MaTAR sequence (mm10) was extracted and screened for transcripts with sequence overlap in the human genome (hg38) using the BLAT alignment tool. If the mouse MaTAR sequence overlapped significantly with an annotated human transcript, this transcript was defined as the human counterpart. For some candidates, sequence identities of up to 70% were obtained while any sequence overlap for others was not observed. Next, the analysis was extended to conserved genomic location (=synteny) by analyzing the nearest neighboring genes of each MaTAR. This was carried out using the UCSC Genome Browser. For instance, if the genomic location of a MaTAR is in close proximity to a protein-coding gene, the surrounding genomic position of the same protein-coding gene in the human genome was screened. Many non-coding RNAs are conserved between different species on the level of genomic location rather than based on sequence, implying functional conservation. Human counterparts for almost all MaTARs were identified based on synteny. In several cases, we observed conservation on both sequence and synteny levels.

Advantages of Certain Embodiments

An RNA-Seq screen was performed to identify lncRNAs that are up-regulated in mammary tumors.

A total of 290 lncRNAs that are up-regulated at least two-fold in tumors were identified. Antisense inhibition of several of these transcripts, particularly, MaTAR transcripts, lead to a reduction or complete loss of organoid branching. Provided herein, for the first time, are methods and compositions for the modulation of a MaTAR that can treat, delay, prevent and/or ameliorate a breast cancer disorder or condition, or a physiological marker thereof. In a particular embodiment, for the first time, MaTAR inhibitors (e.g., oligonucleotides targeting a nucleic acid encoding a MaTAR) are provided for reducing tumor progression, metastasis, cell proliferation, tumor cell invasion, an/or collective cell migration in an animal.

EXAMPLES

Non-Limiting Disclosure and Incorporation by Reference

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1: Comparison of the Transcriptome of Mammary Tumors and Corresponding Organoids The expression of several breast cancer markers, such as estrogen receptor (ER), progesterone receptor (PR), and ER-negative (HER2/neu-amplified and basal-like), from mammary tumors of comparable volume and histological profile, were measured. The mammary tumors were from 3 MMTV-PyMT mice, which is a physiologically relevant mouse model of luminal B subtype of breast cancer.

Organoids from WT nulliparous mammary glands, MMTV-PyMT tumors and MMTV-Neu-NDL tumors were prepared and cultured as described in Ewald Cold Spring Harb. Protoc. 2013: 130-133, 2013. For MMTV-PyMT mice, individual tumors were isolated and organoids were generated in a tumor-specific manner. Mammary epithelial fragments (organoids) were mixed with growth factor-reduced matrigel (Corning) at a concentration of 5 organoids/μL and plated as 80 μL domes in Cellstar 24-well dishes (Greiner Bio One). Organoids were grown in DMEM/F12 medium supplemented with 1×ITS (insulin, transferrin, and sodium selenite) media supplement (Sigma), 1% penicillin/streptomycin, and 2.5 nM murine FGF2 (Peprotech). Comparative RNA-Seq analyses revealed that the global gene expression signature of mammary organoids correlates well with the tumor transcriptome (Pearson correlation coefficient=0.82 for day 0 and 0.84 for day 6). Thus, the first direct transcriptomic comparison of cultured organoids and the tumors they were derived from demonstrates that the gene expression signature of day 6 mammary organoids closely resembles the tumor transcriptome and represents a reliable model system to study the expression of non-coding RNAs. The RNA-Seq data presented here is also publicly available at the NCBI Gene Expression Omnibus (GEO; http://www.ncbi/nlm/nih.gov/geo) under accession number GSE72823.

Example 2: Transcriptome of Luminal B and HER2-Amplified Mammary Tumors

RNA-Seq analysis was performed on physiologically relevant transgenic mouse models of luminal B (MMTV-PyMT) and HER2/neu-amplified (MMTV-Neu-NDL and MMTV-Cre; Flox-Neo-Neu-NT) subtypes of breast cancer (Guy et al, Mol. Cell Biol. 12: 954-961, 1992; Siegel et al, EMBO J. 18: 2149-2164, 1999; Andrechek et al, Proc. Natl. Acad. Sci. USA 97: 3444-3449, 2000).

To identify the complement of lncRNAs expressed in different subtypes of mammary carcinomas, organoids were generated from 5 MMTV-PyMT and 3 MMTV-Neu-NDL mice. After 6 days in matrigel, the transcriptome of the organoids was analyzed using RNA-Seq. Organoids from nulliparous mammary glands of 3 age-matched wild type FVB females served as controls.

Gene-set enrichment analyses (GSEA) revealed that the mouse mammary organoid data resembled the transcriptome of human breast cancer. For instance, the down-regulated genes of both models correlated well with expression signatures of invasive breast cancer and metastatic tumors. A similar correlation was found for up-regulated genes in both datasets.

Taken together, the data demonstrated that mouse mammary carcinoma-derived organoids recapitulated the transcriptome of luminal B and HER2/neu-amplified breast cancer. The data also demonstrate that mouse mammary carcinoma-derived organoids are a reliable model system to study the expression of non-coding RNAs.

Example 3: Identification of Up-Regulated lncRNAs in Mammary Tumors

A catalog of lncRNAs that exhibited altered expression levels in mammary tumor organoids was generated to provide a useful resource for research and drug development.

A total of 484 lncRNAs in MMTV-PyMT and 402 lncRNAs in MMTV-Neu-NDL were identified with an overlap of 122 between both models that are differentially expressed in organoids derived from mammary tumors compared to wild-type (WT) mammary glands. Approximately, 30% of the identified RNA genes are classified as 'lincRNA' (long intergenic non-coding RNAs), 23% as 'processed pseudogenes', 16% as 'antisense' transcripts, and 13% as 'processed' transcripts. The gene biotypes of the 484 lncRNAs differentially expressed in MMTV-PyMT tumor organoids and 402 lncRNAs differentially expressed in MMTV-Neu-NDL tumor organoids is presented in the table below. 'TEC' denotes 'to be experimentally confirmed' (GENCODE classification).

TABLE 3

| Gene biotypes (%) of lncRNA | | |
|---|---|---|
| Gene biotype | MMTV-PyMT | MMTV-Neu-NDL |
| Antisense | 18 | 13 |
| lincRNA | 31 | 27 |
| Processed pseudogene | 16 | 28 |
| Processed transcript | 15 | 10 |
| TEC | 7 | 5 |
| Unprocessed pseudogene | 4 | 3 |
| others | 9 | 14 |

Of these, 109 lncRNAs in MMTV-PyMT and 207 lncRNAs in MMTV-Neu-NDL were up-regulated >two-fold, with an overlap of 26 between both models. These up-regulated genes are presented in the Tables below. The genes marked with an asterisk (*) are the overlapping 26 genes. 'log 2FC' denotes the fold-changes compared to WT mammary organoids, on a log 2 scale. 'adj. p-value' indicates the false-discovery rate (FDR) adjusted p-value, a statistical measure of significance. Differentially expressed genes were included in the Tables below if the log 2FC was ≥2 and the adj. p-value was <0.1. These putative oncogenes represent a diverse group of lncRNAs in terms of their biotypes, length, expression levels, and genomic location (depicted by their Ensembl ID).

TABLE 4

| Up-regulated (≥2-fold) lncRNAs in MMTV-PyMT | | | | |
|---|---|---|---|---|
| Ensembl ID | log2FC | adj. p-value | Biotype | Gene name |
| ENSMUSG00000085541* | 6.5 | 7.14E-51 | antisense | Gm16010 |
| ENSMUSG00000091199* | 5.4 | 1.03E-10 | transcribed unprocessed pseudogene | Gm2619 |
| ENSMUSG00000096802* | 4.6 | 3.21E-06 | processed pseudogene | Gm15433 |
| ENSMUSG00000050334* | 4.5 | 8.45E-13 | lincRNA | C130071C03Rik |
| ENSMUSG00000089652* | 4.4 | 8.77E-06 | lincRNA | Gm16025 |
| ENSMUSG00000090186* | 4.2 | 1.00E-05 | transcribed unprocessed pseudogene | Gm7592 |
| ENSMUSG00000103440 | 4.0 | 6.46E-12 | TEC | Gm37131 |
| ENSMUSG00000082082 | 3.8 | 4.54E-04 | transcribed unprocessed | Gm13230 |
| ENSMUSG00000097960* | 3.6 | 8.17E-17 | lincRNA | A330074K22Rik |
| ENSMUSG00000096292* | 3.6 | 1.14E-03 | processed pseudogene | Gm2666 |
| ENSMUSG00000094991 | 3.6 | 1.25E-03 | lincRNA | Gm21718 |
| ENSMUSG00000087659 | 3.3 | 1.59E-03 | lincRNA | Gm12606 |
| ENSMUSG00000100816* | 3.2 | 6.01E-04 | lincRNA | Gm28321 |
| ENSMUSG00000103620 | 3.0 | 1.54E-03 | antisense | Gm37359 |
| ENSMUSG00000104192 | 3.0 | 4.69E-05 | TEC | Gm37253 |
| ENSMUSG00000099693* | 3.0 | 5.35E-03 | unprocessed pseudogene | Gm29284 |
| ENSMUSG00000098224 | 2.9 | 3.41E-03 | processed pseudogene | Gm7985 |
| ENSMUSG00000086748 | 2.8 | 5.56E-03 | processed transcript | Gm13261 |

TABLE 4-continued

Up-regulated (≥2-fold) lncRNAs in MMTV-PyMT

| Ensembl ID | log2FC | adj. p-value | Biotype | Gene name |
|---|---|---|---|---|
| ENSMUSG00000087051 | 2.7 | 8.83E-04 | lincRNA | Gm12730 |
| ENSMUSG00000051832 | 2.7 | 1.08E-05 | processed transcript | E230016K23Rik |
| ENSMUSG00000073821 | 2.7 | 1.16E-05 | processed transcript | 8030451A03Rik |
| ENSMUSG00000097804 | 2.7 | 3.85E-04 | antisense | Gm16685 |
| ENSMUSG00000083563 | 2.6 | 1.90E-03 | unprocessed pseudogene | Gm13340 |
| ENSMUSG00000083863 | 2.5 | 4.59E-06 | unprocessed pseudogene | Gm13341 |
| ENSMUSG00000082978 | 2.5 | 1.14E-02 | processed pseudogene | Rpsa-ps11 |
| ENSMUSG00000082480 | 2.5 | 7.15E-04 | processed pseudogene | Gm11687 |
| ENSMUSG00000043903* | 2.4 | 1.32E-08 | lincRNA | Gm22 |
| ENSMUSG00000084141 | 2.3 | 3.39E-03 | processed pseudogene | Olfr1372-ps1 |
| ENSMUSG00000087028* | 2.3 | 1.33E-06 | lincRNA | Gm13387 |
| ENSMUSG00000095042 | 2.3 | 8.67E-03 | processed pseudogene | Gm12537 |
| ENSMUSG00000094334 | 2.2 | 5.39E-02 | processed pseudogene | Fabp512 |
| ENSMUSG00000105613 | 2.2 | 1.31E-02 | TEC | RP23-31J24.2 |
| ENSMUSG00000100865 | 2.2 | 1.92E-02 | transcribed processed | Gm9320 |
| ENSMUSG00000084289* | 2.2 | 8.13E-07 | processed pseudogene | Gm6977 |
| ENSMUSG00000069939 | 2.1 | 3.95E-03 | processed pseudogene | Gm12070 |
| ENSMUSG00000103032 | 2.1 | 7.42E-02 | TEC | Gm37121 |
| ENSMUSG00000105353 | 2.1 | 2.57E-02 | lincRNA | RP24-230J14.4 |
| ENSMUSG00000067203* | 2.1 | 2.74E-11 | unprocessed pseudogene | H2-K2 |
| ENSMUSG00000083311 | 2.1 | 5.23E-02 | processed pseudogene | Gm5643 |
| ENSMUSG00000082424 | 2.1 | 2.90E-03 | processed pseudogene | Gm13292 |
| ENSMUSG00000096751 | 2.1 | 8.98E-02 | processed transcript | Gm28373 |
| ENSMUSG00000041449 | 2.0 | 4.73E-07 | transcribed unprocessed pseudogene | Serpina3h |
| ENSMUSG00000086249 | 2.0 | 2.84E-03 | processed transcript | Gm12724 |
| ENSMUSG00000101452 | 2.0 | 2.17E-02 | processed pseudogene | Gm28530 |
| ENSMUSG00000097924* | 2.0 | 7.52E-02 | lincRNA | A730020E08Rik |
| ENSMUSG00000085912* | 2.0 | 9.93E-05 | lincRNA | Trp53cor1 |
| ENSMUSG00000097636 | 2.0 | 5.53E-02 | lincRNA | 5830416P10Rik |
| ENSMUSG00000100750 | 2.0 | 1.98E-02 | antisense | Gm29084 |
| ENSMUSG00000095419 | 2.0 | 1.02E-04 | processed pseudogene | Gm14328 |
| ENSMUSG00000090063 | 1.9 | 7.62E-02 | antisense | Dlx6os1 |
| ENSMUSG00000092171* | 1.9 | 5.16E-04 | lincRNA | 4833427F10Rik |
| ENSMUSG00000105520 | 1.9 | 8.31E-03 | TEC | RP23-105B8.4 |
| ENSMUSG00000082179 | 1.9 | 9.69E-02 | processed pseudogene | Gm11407 |
| ENSMUSG00000096617* | 1.8 | 1.95E-02 | processed pseudogene | Gm5559 |
| ENSMUSG00000093405 | 1.8 | 6.36E-02 | processed transcript | Gm20684 |
| ENSMUSG00000091553 | 1.8 | 3.93E-02 | unprocessed pseudogene | Serpina3e-ps |
| ENSMUSG00000098113 | 1.8 | 2.62E-02 | processed pseudogene | Gm2445 |
| ENSMUSG00000085471 | 1.8 | 7.67E-02 | antisense | 4933423P22Rik |
| ENSMUSG00000085786 | 1.7 | 1.39E-02 | antisense | Gm15987 |
| ENSMUSG00000102550 | 1.7 | 3.13E-02 | processed pseudogene | Gm8276 |
| ENSMUSG00000080775 | 1.7 | 9.19E-02 | processed pseudogene | Gm6368 |
| ENSMUSG00000105356 | 1.7 | 6.77E-02 | TEC | RP23-480P21.3 |
| ENSMUSG00000098019 | 1.7 | 2.55E-02 | processed pseudogene | Gm2546 |
| ENSMUSG00000090307 | 1.6 | 1.09E-02 | antisense | 1700071M16Rik |
| ENSMUSG00000089728 | 1.6 | 8.26E-02 | unprocessed pseudogene | Clec2f |
| ENSMUSG00000063586 | 1.6 | 9.97E-02 | processed pseudogene | Gm5513 |
| ENSMUSG00000026729 | 1.6 | 6.21E-02 | lincRNA | 4930562F07Rik |
| ENSMUSG00000104693* | 1.5 | 7.23E-02 | sense intronic | RP23-103P11.1 |
| ENSMUSG00000097728 | 1.5 | 4.95E-03 | lincRNA | Gm26840 |
| ENSMUSG00000103755 | 1.5 | 1.18E-05 | TEC | Gm37805 |
| ENSMUSG00000067389* | 1.5 | 7.68E-05 | antisense | Gm17080 |
| ENSMUSG00000097800 | 1.5 | 5.87E-03 | lincRNA | B230344G16Rik |
| ENSMUSG00000099492 | 1.4 | 3.30E-02 | processed pseudogene | Gm5525 |
| ENSMUSG00000082762 | 1.4 | 8.01E-02 | processed pseudogene | Gm12366 |
| ENSMUSG00000097660* | 1.4 | 7.59E-02 | lincRNA | Gm26762 |
| ENSMUSG00000099471 | 1.4 | 6.99E-03 | processed pseudogene | Gm8451 |
| ENSMUSG00000079311 | 1.4 | 4.13E-03 | processed pseudogene | Gm3222 |
| ENSMUSG00000104018 | 1.4 | 7.37E-02 | TEC | 4833412K13Rik |
| ENSMUSG00000105263 | 1.4 | 8.60E-02 | TEC | RP24-230J14.5 |
| ENSMUSG00000074280 | 1.4 | 2.95E-05 | pseudogene | Gm6166 |
| ENSMUSG00000080746 | 1.4 | 4.49E-02 | processed pseudogene | Rpsa-ps12 |
| ENSMUSG00000085399* | 1.4 | 5.59E-02 | processed transcript | Foxd2os |
| ENSMUSG00000101249 | 1.3 | 1.99E-04 | unprocessed pseudogene | Gm29216 |
| ENSMUSG00000086321 | 1.3 | 5.81E-02 | antisense | Gm11413 |
| ENSMUSG00000094708 | 1.3 | 9.14E-02 | processed pseudogene | Gm10359 |
| ENSMUSG00000100131 | 1.3 | 5.73E-02 | unprocessed pseudogene | Gm28439 |
| ENSMUSG00000087528* | 1.3 | 8.31E-03 | processed transcript | 9830144P21Rik |
| ENSMUSG00000104737* | 1.3 | 2.02E-02 | sense intronic | RP23-103P11.2 |
| ENSMUSG00000105954 | 1.2 | 4.07E-04 | TEC | RP24-299A7.2 |
| ENSMUSG00000097979 | 1.2 | 4.94E-02 | transcribed processed pseudogene | Gm4691 |
| ENSMUSG00000103098 | 1.2 | 8.37E-02 | processed pseudogene | Gm37559 |
| ENSMUSG00000104000* | 1.2 | 6.68E-02 | lincRNA | Gm38335 |

TABLE 4-continued

Up-regulated (≥2-fold) lncRNAs in MMTV-PyMT

| Ensembl ID | log2FC | adj. p-value | Biotype | Gene name |
|---|---|---|---|---|
| ENSMUSG00000083773 | 1.2 | 1.64E-03 | processed pseudogene | Gm13394 |
| ENSMUSG00000097113 | 1.1 | 1.52E-02 | lincRNA | Gm19705 |
| ENSMUSG00000097090 | 1.1 | 9.31E-02 | lincRNA | Gm26724 |
| ENSMUSG00000075391 | 1.1 | 2.13E-02 | processed pseudogene | Gm13443 |
| ENSMUSG00000081208 | 1.1 | 7.94E-03 | processed pseudogene | Gm11400 |
| ENSMUSG00000084974 | 1.1 | 5.82E-02 | processed transcript | Gm15567 |
| ENSMUSG00000043889 | 1.1 | 5.82E-03 | pseudogene | Gm8399 |
| ENSMUSG00000102070 | 1.1 | 1.68E-02 | unprocessed pseudogene | Gm28661 |
| ENSMUSG00000103039 | 1.1 | 5.80E-02 | TEC | Gm37123 |
| ENSMUSG00000066553 | 1.1 | 2.54E-02 | processed pseudogene | Gm6969 |
| ENSMUSG00000105558 | 1.0 | 2.97E-02 | processed pseudogene | RP23-349J3.8 |
| ENSMUSG00000090610 | 1.0 | 5.62E-02 | pseudogene | Gm3571 |
| ENSMUSG00000089776* | 1.0 | 3.73E-02 | antisense | Gm15684 |
| ENSMUSG00000054418 | 1.0 | 3.94E-02 | processed transcript | Gm12715 |
| ENSMUSG00000090330 | 1.0 | 3.02E-02 | antisense | 9130221H12Rik |
| ENSMUSG00000059195 | 1.0 | 1.66E-05 | processed pseudogene | Gm12715 |
| ENSMUSG00000084145 | 1.0 | 5.77E-02 | processed pseudogene | Gm12263 |

TABLE 5

Up-regulated (≥2-fold) lncRNAs in MMTV-Neu-NDL

| Ensembl ID | log2FC | adj. p-value | Biotype | Gene name |
|---|---|---|---|---|
| ENSMUSG00000085541* | 6.2 | 6.02E-35 | antisense | Gm16010 |
| ENSMUSG00000091199* | 5.8 | 6.90E-13 | transcribed unprocessed pseudogene | Gm2619 |
| ENSMUSG00000079457 | 5.6 | 2.97E-09 | transcribed unprocessed pseudogene | Gm7609 |
| ENSMUSG00000096802* | 5.5 | 1.84E-09 | processed pseudogene | Gm15433 |
| ENSMUSG00000087028* | 4.8 | 1.50E-13 | lincRNA | Gm13387 |
| ENSMUSG00000090186* | 4.8 | 2.24E-07 | transcribed unprocessed pseudogene | Gm7592 |
| ENSMUSG00000096292* | 4.7 | 2.74E-06 | processed pseudogene | Gm2666 |
| ENSMUSG00000104645 | 4.6 | 3.40E-08 | lincRNA | RP23-437C24.2 |
| ENSMUSG00000073902 | 4.5 | 1.69E-08 | unprocessed pseudogene | Gm1966 |
| ENSMUSG00000105811 | 4.4 | 2.08E-10 | lincRNA | RP23-327I19.1 |
| ENSMUSG00000082292 | 4.1 | 5.28E-09 | processed pseudogene | Gm12250 |
| ENSMUSG00000075549 | 4.0 | 7.07E-10 | antisense | Gm6878 |
| ENSMUSG00000089652* | 4.0 | 2.50E-04 | lincRNA | Gm16025 |
| ENSMUSG00000106230 | 3.9 | 6.45E-07 | lincRNA | RP23-447N11.2 |
| ENSMUSG00000085452 | 3.8 | 7.54E-04 | lincRNA | 4930554G24Rik |
| ENSMUSG00000085083 | 3.7 | 2.97E-04 | antisense | Gm11615 |
| ENSMUSG00000099375 | 3.6 | 3.24E-06 | lincRNA | Gm28187 |
| ENSMUSG00000082305 | 3.6 | 2.90E-12 | unprocessed pseudogene | Gm2420 |
| ENSMUSG00000086964 | 3.6 | 7.66E-04 | antisense | Gm15948 |
| ENSMUSG00000102801 | 3.6 | 2.17E-03 | TEC | Gm37478 |
| ENSMUSG00000084328 | 3.6 | 1.42E-04 | processed pseudogene | Gm14046 |
| ENSMUSG00000085218 | 3.5 | 2.91E-04 | processed transcript | BB218582 |
| ENSMUSG00000100252 | 3.4 | 2.33E-04 | lincRNA | Mir124-2hg |
| ENSMUSG00000097766 | 3.4 | 2.36E-09 | lincRNA | 5730420D15Rik |
| ENSMUSG00000102160 | 3.3 | 5.52E-04 | TEC | Gm36944 |
| ENSMUSG00000081665 | 3.3 | 1.27E-05 | unprocessed pseudogene | Gm15922 |
| ENSMUSG00000083161 | 3.2 | 3.34E-03 | unprocessed pseudogene | Gm11427 |
| ENSMUSG00000099157 | 3.2 | 7.23E-03 | misc RNA | Gm27804 |
| ENSMUSG00000090252 | 3.2 | 6.22E-03 | antisense | Gm16028 |
| ENSMUSG00000085295 | 3.1 | 6.40E-04 | antisense | 4930430E12Rik |
| ENSMUSG00000102389 | 3.1 | 3.02E-03 | TEC | D630023O14Rik |
| ENSMUSG00000097924* | 3.1 | 2.17E-03 | lincRNA | A730020E08Rik |
| ENSMUSG00000100009 | 3.1 | 2.37E-05 | lincRNA | Gm7967 |
| ENSMUSG00000099693* | 3.1 | 3.25E-03 | unprocessed pseudogene | Gm29284 |
| ENSMUSG00000106004 | 3.0 | 1.34E-02 | antisense | RP24-152F23.2 |
| ENSMUSG00000087326 | 3.0 | 4.18E-05 | processed transcript | Gm12503 |
| ENSMUSG00000087107 | 3.0 | 7.23E-06 | lincRNA | AI662270 |
| ENSMUSG00000087248 | 2.9 | 6.61E-04 | antisense | Gm16120 |
| ENSMUSG00000086605 | 2.9 | 1.62E-06 | lincRNA | Gm14290 |
| ENSMUSG00000082433 | 2.9 | 6.86E-05 | processed pseudogene | Gm9025 |
| ENSMUSG00000063286 | 2.9 | 9.43E-05 | unprocessed pseudogene | Gm8995 |
| ENSMUSG00000085399* | 2.9 | 2.43E-12 | processed transcript | Foxd2os |
| ENSMUSG00000066170 | 2.8 | 2.14E-06 | lincRNA | E230001N04Rik |
| ENSMUSG00000085696 | 2.8 | 1.12E-02 | antisense | Hoxaas3 |
| ENSMUSG00000061852 | 2.8 | 3.05E-02 | unprocessed pseudogene | Gm7582 |
| ENSMUSG00000102788 | 2.8 | 5.19E-03 | TEC | Gm38255 |

TABLE 5-continued

Up-regulated (≥2-fold) lncRNAs in MMTV-Neu-NDL

| Ensembl ID | log2FC | adj. p-value | Biotype | Gene name |
|---|---|---|---|---|
| ENSMUSG00000081723 | 2.7 | 2.79E-04 | unprocessed pseudogene | Gm15931 |
| ENSMUSG00000073538 | 2.7 | 1.53E-02 | processed transcript | E330020D12Rik |
| ENSMUSG00000099848 | 2.7 | 1.13E-04 | lincRNA | Gm29337 |
| ENSMUSG00000087658 | 2.7 | 2.01E-02 | antisense | Hotairm1 |
| ENSMUSG00000078122 | 2.7 | 2.53E-03 | antisense | F630028O10Rik |
| ENSMUSG00000036322 | 2.7 | 1.74E-02 | unprocessed pseudogene | H2-Ea-ps |
| ENSMUSG00000104350 | 2.7 | 1.52E-04 | TEC | Gm38244 |
| ENSMUSG00000087139 | 2.6 | 1.98E-02 | antisense | Gm11683 |
| ENSMUSG00000078952 | 2.6 | 9.17E-04 | lincRNA | Lincenc1 |
| ENSMUSG00000083489 | 2.6 | 4.41E-02 | unprocessed pseudogene | Gm11784 |
| ENSMUSG00000100550 | 2.6 | 5.94E-03 | lincRNA | 2310039L15Rik |
| ENSMUSG00000100816* | 2.6 | 2.41E-02 | lincRNA | Gm28321 |
| ENSMUSG00000083708 | 2.6 | 1.91E-02 | processed pseudogene | Gm13123 |
| ENSMUSG00000086704 | 2.6 | 4.30E-02 | antisense | Gm14582 |
| ENSMUSG00000050334* | 2.5 | 4.12E-03 | lincRNA | C130071C03Rik |
| ENSMUSG00000099111 | 2.5 | 4.71E-02 | misc RNA | Gm27369 |
| ENSMUSG00000082116 | 2.5 | 4.97E-02 | processed pseudogene | Gm12188 |
| ENSMUSG00000104022 | 2.5 | 3.79E-02 | sense intronic | Gm37214 |
| ENSMUSG00000074465 | 2.5 | 2.55E-02 | antisense | Gm10701 |
| ENSMUSG00000085912* | 2.5 | 1.41E-08 | lincRNA | Trp53cor1 |
| ENSMUSG00000084243 | 2.5 | 4.76E-02 | processed pseudogene | Gm13784 |
| ENSMUSG00000084826 | 2.5 | 5.37E-02 | antisense | AI847159 |
| ENSMUSG00000105397 | 2.4 | 3.11E-03 | processed pseudogene | RP23-335E20.2 |
| ENSMUSG00000097076 | 2.4 | 6.75E-02 | lincRNA | Platr7 |
| ENSMUSG00000086109 | 2.4 | 6.22E-02 | lincRNA | Gm13391 |
| ENSMUSG00000078601 | 2.4 | 4.57E-02 | lincRNA | Gm12525 |
| ENSMUSG00000074805 | 2.4 | 1.54E-02 | antisense | Il1bos |
| ENSMUSG00000084108 | 2.4 | 6.96E-02 | processed pseudogene | Gm15794 |
| ENSMUSG00000092171* | 2.4 | 1.52E-02 | lincRNA | 4833427F10Rik |
| ENSMUSG00000100301 | 2.4 | 9.52E-18 | lincRNA | 6030407O03Rik |
| ENSMUSG00000085833 | 2.3 | 1.07E-02 | lincRNA | Gm13003 |
| ENSMUSG00000106396 | 2.3 | 4.97E-02 | antisense | RP24-140D11.1 |
| ENSMUSG00000105492 | 2.3 | 6.27E-02 | processed pseudogene | RP24-224P21.1 |
| ENSMUSG00000082072 | 2.3 | 3.89E-03 | processed pseudogene | Gm15785 |
| ENSMUSG00000072683 | 2.3 | 7.88E-02 | processed transcript | Gm7457 |
| ENSMUSG00000097281 | 2.3 | 1.29E-02 | lincRNA | Gm26685 |
| ENSMUSG00000103596 | 2.3 | 7.93E-02 | TEC | Gm37354 |
| ENSMUSG00000054510 | 2.3 | 6.38E-02 | lincRNA | Gm14461 |
| ENSMUSG00000056716 | 2.3 | 8.63E-03 | lincRNA | Gm5420 |
| ENSMUSG00000087149 | 2.3 | 9.63E-05 | transcribed unprocessed pseudogene | Itih5l-ps |
| ENSMUSG00000044633 | 2.3 | 3.87E-04 | lincRNA | B530045E10Rik |
| ENSMUSG00000043903* | 2.3 | 1.20E-05 | lincRNA | Gm22 |
| ENSMUSG00000082127 | 2.2 | 7.72E-08 | processed pseudogene | Gm13577 |
| ENSMUSG00000099757 | 2.2 | 1.25E-02 | processed transcript | BE692007 |
| ENSMUSG00000101210 | 2.2 | 3.46E-02 | lincRNA | Gm28720 |
| ENSMUSG00000097730 | 2.2 | 3.06E-02 | lincRNA | Gm26588 |
| ENSMUSG00000097673 | 2.2 | 2.03E-02 | lincRNA | Gm26608 |
| ENSMUSG00000087364 | 2.2 | 2.59E-02 | antisense | Gm13398 |
| ENSMUSG00000105374 | 2.2 | 8.92E-02 | TEC | RP24-230L5.2 |
| ENSMUSG00000097639 | 2.2 | 3.80E-03 | lincRNA | Platr4 |
| ENSMUSG00000102827 | 2.1 | 1.46E-02 | transcribed processed pseudogene | Gm8242 |
| ENSMUSG00000081833 | 2.1 | 4.94E-03 | processed pseudogene | Gm13669 |
| ENSMUSG00000101365 | 2.1 | 1.07E-02 | lincRNA | Gm19325 |
| ENSMUSG00000085702 | 2.1 | 7.92E-02 | antisense | Mecomos |
| ENSMUSG00000086187 | 2.0 | 2.39E-02 | lincRNA | Gm12860 |
| ENSMUSG00000072387 | 2.0 | 8.27E-02 | processed pseudogene | Gm10356 |
| ENSMUSG00000063388 | 2.0 | 1.74E-02 | pseudogene | BC023105 |
| ENSMUSG00000082956 | 2.0 | 9.02E-02 | unprocessed pseudogene | Naip3 |
| ENSMUSG00000085182 | 2.0 | 1.85E-02 | antisense | Gm13596 |
| ENSMUSG00000087528* | 2.0 | 8.13E-08 | processed transcript | 9830144P21Rik |
| ENSMUSG00000106524 | 2.0 | 6.38E-07 | lincRNA | RP23-229C5.2 |
| ENSMUSG00000105057 | 2.0 | 9.56E-02 | lincRNA | RP23-71G16.7 |
| ENSMUSG00000106654 | 2.0 | 5.34E-02 | processed pseudogene | RP23-118L1.5 |
| ENSMUSG00000101344 | 2.0 | 1.68E-07 | lincRNA | Gm29183 |
| ENSMUSG00000096938 | 2.0 | 3.44E-02 | lincRNA | 9530052E02Rik |
| ENSMUSG00000105260 | 2.0 | 2.67E-02 | lincRNA | RP23-325M18.5 |
| ENSMUSG00000097814 | 1.9 | 4.72E-02 | antisense | Panct2 |
| ENSMUSG00000087014 | 1.9 | 8.43E-03 | antisense | Gm16364 |
| ENSMUSG00000099604 | 1.9 | 3.74E-02 | processed pseudogene | Gm6651 |
| ENSMUSG00000061728 | 1.9 | 7.10E-02 | unprocessed pseudogene | Btn17-ps |
| ENSMUSG00000023341 | 1.9 | 1.19E-03 | polymorphic pseudogene | Mx2 |
| ENSMUSG00000091575 | 1.9 | 2.46E-03 | processed transcript | 2010016I18Rik |
| ENSMUSG00000096617* | 1.9 | 1.74E-03 | processed pseudogene | Gm5559 |
| ENSMUSG00000075027 | 1.9 | 2.87E-03 | processed transcript | 4631405J19Rik |

TABLE 5-continued

Up-regulated (≥2-fold) lncRNAs in MMTV-Neu-NDL

| Ensembl ID | log2FC | adj. p-value | Biotype | Gene name |
|---|---|---|---|---|
| ENSMUSG00000106164 | 1.9 | 4.10E-02 | lincRNA | RP24-292F8.1 |
| ENSMUSG00000083152 | 1.8 | 7.09E-02 | transcribed processed pseudogene | Apc-ps1 |
| ENSMUSG00000086150 | 1.8 | 1.23E-02 | antisense | Bach2os |
| ENSMUSG00000089711 | 1.8 | 5.45E-02 | antisense | Gm16240 |
| ENSMUSG00000087113 | 1.8 | 1.55E-02 | processed transcript | Gm11714 |
| ENSMUSG00000105326 | 1.8 | 3.44E-02 | TEC | RP24-230L5.3 |
| ENSMUSG00000105453 | 1.8 | 9.72E-02 | TEC | RP23-31L10.4 |
| ENSMUSG00000097887 | 1.8 | 3.15E-02 | lincRNA | Gm26542 |
| ENSMUSG00000093826 | 1.8 | 6.52E-04 | processed pseudogene | Gm6900 |
| ENSMUSG00000082192 | 1.7 | 5.03E-02 | processed pseudogene | Gm14719 |
| ENSMUSG00000097242 | 1.7 | 1.95E-13 | lincRNA | Gm16907 |
| ENSMUSG00000097352 | 1.7 | 2.75E-02 | transcribed unprocessed pseudogene | C920009B18Rik |
| ENSMUSG00000103532 | 1.7 | 2.49E-02 | TEC | Gm4430 |
| ENSMUSG00000104616 | 1.7 | 3.71E-02 | processed pseudogene | RP23-325M18.2 |
| ENSMUSG00000097471 | 1.7 | 7.62E-02 | lincRNA | 5830432E09Rik |
| ENSMUSG00000105741 | 1.7 | 8.53E-03 | TEC | RP23-396H16.2 |
| ENSMUSG00000100005 | 1.7 | 1.34E-02 | processed transcript | B130024G19Rik |
| ENSMUSG00000084289* | 1.7 | 1.62E-03 | processed pseudogene | Gm6977 |
| ENSMUSG00000029605 | 1.6 | 1.14E-03 | polymorphic pseudogene | Oas1b |
| ENSMUSG00000090399 | 1.6 | 8.53E-02 | lincRNA | Gm38399 |
| ENSMUSG00000096980 | 1.6 | 2.71E-02 | lincRNA | Gm26526 |
| ENSMUSG00000086712 | 1.6 | 1.42E-02 | lincRNA | AI427809 |
| ENSMUSG00000097660* | 1.6 | 5.14E-02 | lincRNA | Gm26762 |
| ENSMUSG00000084807 | 1.6 | 1.67E-02 | lincRNA | Gm13073 |
| ENSMUSG00000084183 | 1.6 | 1.68E-02 | processed pseudogene | Gm12009 |
| ENSMUSG00000074067 | 1.6 | 6.09E-02 | lincRNA | Gm10619 |
| ENSMUSG00000104693* | 1.6 | 9.42E-02 | sense intronic | RP23-103P11.1 |
| ENSMUSG00000084274 | 1.6 | 1.20E-02 | transcribed processed pseudogene | Gm12504 |
| ENSMUSG00000103009 | 1.5 | 1.41E-03 | TEC | Gm4430 |
| ENSMUSG00000097960* | 1.5 | 2.72E-02 | lincRNA | A330074K22Rik |
| ENSMUSG00000090222 | 1.5 | 4.69E-02 | unprocessed pseudogene | Gm16340 |
| ENSMUSG00000047643 | 1.5 | 1.45E-02 | processed pseudogene | Gm5454 |
| ENSMUSG00000106288 | 1.5 | 7.51E-02 | TEC | RP24-140D11.6 |
| ENSMUSG00000087684 | 1.5 | 4.97E-04 | lincRNA | 1200007C13Rik |
| ENSMUSG00000093619 | 1.5 | 7.54E-03 | antisense | 4930535L15Rik |
| ENSMUSG00000067389* | 1.5 | 2.84E-06 | antisense | Gm17080 |
| ENSMUSG00000104973 | 1.5 | 9.91E-02 | sense intronic | RP23-357D17.3 |
| ENSMUSG00000105324 | 1.5 | 8.13E-02 | lincRNA | RP23-229C5.1 |
| ENSMUSG00000105107 | 1.5 | 7.62E-02 | TEC | RP23-214I6.4 |
| ENSMUSG00000052403 | 1.5 | 4.74E-02 | antisense | Fcnaos |
| ENSMUSG00000104126 | 1.5 | 1.39E-02 | processed pseudogene | Gm37486 |
| ENSMUSG00000101431 | 1.5 | 3.36E-02 | processed pseudogene | Gm7901 |
| ENSMUSG00000089755 | 1.5 | 1.06E-02 | antisense | 0610012D04Rik |
| ENSMUSG00000085836 | 1.5 | 8.30E-02 | lincRNA | Gm13074 |
| ENSMUSG00000067121 | 1.4 | 4.63E-08 | processed pseudogene | Gm7027 |
| ENSMUSG00000102259 | 1.4 | 1.01E-02 | TEC | Gm38230 |
| ENSMUSG00000104263 | 1.4 | 5.64E-02 | TEC | 9430062P05Rik |
| ENSMUSG00000072962 | 1.4 | 4.79E-02 | antisense | Gm16401 |
| ENSMUSG00000106028 | 1.4 | 1.83E-02 | unprocessed pseudogene | RP23-20307.3 |
| ENSMUSG00000087362 | 1.4 | 3.52E-02 | lincRNA | Gm13710 |
| ENSMUSG00000097194 | 1.4 | 6.75E-02 | lincRNA | 9330175E14Rik |
| ENSMUSG00000100147 | 1.4 | 9.87E-02 | lincRNA | 1700047M11Rik |
| ENSMUSG00000089776* | 1.3 | 3.47E-02 | antisense | Gm15684 |
| ENSMUSG00000067203* | 1.3 | 4.25E-04 | unprocessed pseudogene | H2-K2 |
| ENSMUSG00000100701 | 1.3 | 7.08E-03 | processed pseudogene | Gm19587 |
| ENSMUSG00000079671 | 1.3 | 3.28E-02 | processed transcript | 2610203C22Rik |
| ENSMUSG00000046993 | 1.3 | 4.58E-02 | processed pseudogene | Gm5637 |
| ENSMUSG00000103653 | 1.3 | 7.07E-02 | processed pseudogene | Gm3934 |
| ENSMUSG00000097908 | 1.3 | 1.89E-04 | lincRNA | 4933404O12Rik |
| ENSMUSG00000102813 | 1.3 | 1.76E-05 | TEC | Gm37795 |
| ENSMUSG00000089817 | 1.2 | 1.84E-03 | processed pseudogene | Gm7162 |
| ENSMUSG00000064281 | 1.2 | 1.37E-02 | processed pseudogene | Rpl19-ps1 |
| ENSMUSG00000097378 | 1.2 | 1.81E-02 | lincRNA | B230208H11Rik |
| ENSMUSG00000085174 | 1.2 | 3.46E-02 | antisense | Gm16206 |
| ENSMUSG00000074506 | 1.2 | 2.87E-02 | processed pseudogene | Gm10705 |
| ENSMUSG00000079491 | 1.2 | 7.50E-05 | polymorphic pseudogene | H2-T10 |
| ENSMUSG00000089769 | 1.2 | 8.31E-03 | processed pseudogene | Gm16574 |
| ENSMUSG00000084781 | 1.2 | 4.72E-02 | processed transcript | D930015M05Rik |
| ENSMUSG00000085558 | 1.2 | 5.40E-02 | processed transcript | 4930412C18Rik |
| ENSMUSG00000081684 | 1.2 | 1.48E-02 | processed pseudogene | Rps2-ps13 |
| ENSMUSG00000100158 | 1.2 | 5.33E-02 | sense intronic | Gm28119 |
| ENSMUSG00000093507 | 1.2 | 6.27E-02 | processed transcript | Gm20627 |
| ENSMUSG00000104000* | 1.1 | 4.87E-02 | lincRNA | Gm38335 |

TABLE 5-continued

Up-regulated (≥2-fold) lncRNAs in MMTV-Neu-NDL

| Ensembl ID | log2FC | adj. p-value | Biotype | Gene name |
|---|---|---|---|---|
| ENSMUSG00000096918 | 1.1 | 9.92E-02 | lincRNA | Gm16863 |
| ENSMUSG00000086894 | 1.1 | 5.59E-02 | sense intronic | Gm15708 |
| ENSMUSG00000101878 | 1.1 | 4.59E-03 | processed pseudogene | Gm8203 |
| ENSMUSG00000092569 | 1.1 | 3.53E-02 | processed transcript | Gm20544 |
| ENSMUSG00000104737* | 1.1 | 6.02E-02 | sense intronic | RP23-103P11.2 |
| ENSMUSG00000085873 | 1.1 | 1.41E-03 | antisense | Ttc39aos1 |
| ENSMUSG00000086453 | 1.1 | 9.40E-02 | antisense | Gm11457 |
| ENSMUSG00000073145 | 1.1 | 8.67E-02 | antisense | Gm12000 |
| ENSMUSG00000082475 | 1.1 | 1.49E-02 | processed pseudogene | Gm7206 |
| ENSMUSG00000106237 | 1.0 | 2.33E-02 | lincRNA | RP23-45G4.3 |
| ENSMUSG00000097092 | 1.0 | 2.96E-02 | lincRNA | Gm26725 |
| ENSMUSG00000097145 | 1.0 | 1.69E-03 | lincRNA | 9230114K14Rik |
| ENSMUSG00000105742 | 1.0 | 4.97E-02 | TEC | RP24-347B12.1 |
| ENSMUSG00000104913 | 1.0 | 1.20E-03 | processed pseudogene | RP24-324L19.3 |

The distribution of lncRNA across chromosomes is further presented in the Table below. The 'Genome' column depicts the total number of lncRNAs per chromosome according to GENCODE mV5 annotations; the 'PyMT' column depicts differentially expressed lncRNAs in MMTV-PyMT; the 'Neu' column depicts the differentially expressed lncRNAs in MMTV-Neu-NDL.

TABLE 6

Total and differential gene expression across chromosomes

| Chr | Genome | PyMT | Neu |
|---|---|---|---|
| 1 | 3290 | 49 | 59 |
| 2 | 3093 | 36 | 35 |
| 3 | 2704 | 33 | 37 |
| 4 | 2356 | 33 | 44 |
| 5 | 2624 | 27 | 45 |
| 6 | 1524 | 25 | 27 |
| 7 | 2170 | 18 | 25 |
| 8 | 1045 | 10 | 17 |
| 9 | 1582 | 17 | 20 |
| 10 | 967 | 8 | 21 |
| 11 | 2436 | 34 | 34 |
| 12 | 756 | 15 | 8 |
| 13 | 794 | 18 | 21 |
| 14 | 885 | 10 | 10 |
| 15 | 727 | 9 | 8 |
| 16 | 824 | 11 | 9 |
| 17 | 1178 | 16 | 22 |
| 18 | 463 | 9 | 15 |
| 19 | 573 | 10 | 6 |
| X | 1970 | 13 | 20 |
| Y | 1417 | 0 | 0 |

Of the up-regulated lncRNAs, 30 transcripts were selected for further evaluation based on their overexpression in at least 4 out of 5 sequenced PyMT organoid datasets as well as significant upregulation in PyMT tumor sections. These transcripts were also selected based on several stringest criteria: i) statistical significance (FDR adjusted p-value <0.1; ii) at least two-fold up-regulation in tumor organoids and/or tumor sections compared to normal mammary organoids; iii) sufficient read coverage per transcript to eliminate very lowly abundant RNAs; iv) human conservation based on sequence and/or synteny; v) location in an intergenic genomic region; and vi) lack of highly repetitive elements. RNA-Seq data from MMTV-Cre; Flox-Neo-Neu-NT tumors, a second model for the HER2/neu-amplified subtype of human breast cancer, was also included to further refine the candidate lncRNAs. In addition, transcripts of highest clinical value were selected applying the following criteria: i) Up-regulation ≥2-fold compared to WT mammary gland organoids, ii) statistical significance (adjusted p-value <0.1), iii) intergenic location in the genome, iv) lack of highly repetitive regions and v) conservation in human based on sequence and/or synteny. These transcripts were termed Mammary Tumor Associated RNA 1-30 (MaTAR 1-30). These MaTARs are further presented in the Table below.

The expression levels of MaTARs in mammary tumors to other organs were compared by expression analysis of ENCODE datasets. The results confirmed tissue-specific expression of lncRNAs. The results indicated that 20 MaTARs show either exclusive expression or strong upregulation in mammary tumors.

TABLE 7

MaTARs in all datasets

| MaTAR | Ensembl ID | Gene Name | Biotype |
|---|---|---|---|
| 1 | ENSMUSG00000050334 | C130071C03Rik | lincRNA |
| 2 | ENSMUSG00000061852 | Gm7582 | unprocessed pseudogene |
| 3 | ENSMUSG00000097924 | A730020E08Rik | lincRNA |
| 4 | ENSMUSG00000087658 | Hotairm, Gm15051, Hoxaas1 | anti sense |
| 5 | ENSMUSG00000084328 | Gm14046 | processed pseudogene |
| 6 | ENSMUSG00000092171 | 4833427F10Rik | lincRNA |
| 7 | ENSMUSG00000085399 | Foxd2os, 9130206I24Rik | processed transcript |
| 8 | ENSMUSG00000092569 | Gm20544, lncRNA-Smad7 | processed transcript |
| 9 | ENSMUSG00000046993 | Gm5637 | processed pseudogene |
| 10 | ENSMUSG00000082433 | Gm9025, Ncf2-rs | processed pseudogene |

TABLE 7-continued

MaTARs in all datasets

| MaTAR | Ensembl ID | Gene Name | Biotype |
|---|---|---|---|
| 11 | ENSMUSG00000086712 | A1427809, LOC381524 | lincRNA |
| 12 | ENSMUSG00000085541 | Gm16010 | antisense |
| 13 | ENSMUSG00000096802 | Gm15433 | processed pseudogene |
| 14 | ENSMUSG00000089652 | Gm16025 | lincRNA |
| 15 | ENSMUSG00000084289 | Gm6977 | processed pseudogene |
| 16 | ENSMUSG00000086249 | Gm12724 | processed transcript |
| 17 | ENSMUSG00000097908 | 4933404O12Rik | lincRNA |
| 18 | ENSMUSG00000085873 | Ttc39aos1, Gm12750 | antisense |
| 19 | ENSMUSG00000082088 | Gm15753 | unprocessed pseudogene |
| 20 | ENSMUSG00000087028 | Gm13387 | lincRNA |
| 21 | ENSMUSG00000082305 | Gm2420 | unprocessed pseudogene |
| 22 | ENSMUSG00000085295 | 4930430E12Rik | antisense |
| 23 | ENSMUSG00000082956 | Naip3, Birc1c, EG667838, Naip3, Naip-rs5 | unprocessed pseudogene |
| 24 | ENSMUSG00000084274 | Gm12504 | transcribed processed pseudogene |
| 25 | ENSMUSG00000087684 | 1200007C13Rik | lincRNA |
| 26 | ENSMUSG00000097378 | B230208H11Rik | lincRNA |
| 27 | ENSMUSG00000087235 | Gm4750 | transcribed processed pseudogene |
| 28 | ENSMUSG00000087051 | Gm12730 | lincRNA |
| 29 | ENSMUSG00000095419 | Gm14328 | processed pseudogene |
| 30 | ENSMUSG00000074280 | Gm6166 | pseudogene |

To further characterize MaTARs in the context of global gene expression and to elucidate their potential as 'driver genes' in mammary carcinogenesis, weighed gene correlation network analysis (WGCNA) (Langfelder and Horvath, BMC Bioinformatics 9: 559, 2008) was performed. A full list of all MaTARs and their network modules is provided in the Table below. Of the modules, the 'mammary epithelium' module is enriched for genes that are highly expressed in our RNA-Seq datasets, both in normal mammary gland organoids as well as mammary tumors. The module comprises 5,744 genes, of which only 2,588 genes are classified as 'protein coding'. The coding potential of all MaTARs was tested using CPAT (Wang et al, 2013). While 63% of the MaTARs were classified as non-coding, 37% were predicted to be coding, attributed to the pseudogene fraction. This emphasizes the tissue specificity of non-coding RNA species as well as their potential functional role. MaTARs were further characterized according to their total length and number of exons. MaTARs range from 291-4,867 nucleotides with the majority of MaTARs being shorted than 1,500 nucleotides.

Notably, 16 of the 17 MaTARs in the mammary epithelium module were also highly expressed in tumor tissue compared to normal organs. This indicates that MaTARs are excellent marker genes and sufficient to stratify mammary epithelia from other tissue types.

As presented in the Table below, 'kTotal'=whole network connectivity; 'kWithin'=intramodular connectivity. Both values can be used to identify hub genes; genes are likely hub genes if their 'kWithin' is high, i.e. close to the 'kTotal' value. 'Eigengene corr'=Correlation of the respective MaTAR with the module Eigengene. The Eigengene represents the first principal component of the module. The closer this number is to 1, the higher the correlation of a MaTAR and its eigengene, and the more likely that the respective MaTAR is a hub gene. Positive values indicate positive correlation, negative values indicate negative correlation. 'GO' means gene ontology. At least 6 MaTARs (MaTAR5, 6, 9, 15, 16, and 30) fall into this region, indicating their important within the module.

TABLE 8

Network modules of MaTARs

| MaTAR | Tissue expression | GO terms | kTotal | kWithin | Eigengene corr |
|---|---|---|---|---|---|
| 1 | CNS | neuronal development | 1425 | 702 | 0.8 |
| 2 | thymus/spleen | immune system | 579 | 62 | 0.8 |
| 3 | CNS | neuronal development | 885 | 545 | 0.7 |
| 4 | adult tissue | metabolism | 1023 | 528 | −0.8 |
| 5 | mammary epithelium | epithelia | 2350 | 1565 | 0.9 |
| 6 | mammary epithelium | epithelia | 2424 | 1615 | 0.9 |
| 7 | adult tissue | metabolism | 699 | 252 | −0.5 |
| 8 | mammary epithelium | epithelia | 1311 | 770 | 0.7 |
| 9 | mammary epithelium | epithelia | 2768 | 1811 | 1.0 |
| 10 | mammary epithelium | epithelia | 2120 | 1436 | 0.9 |
| 11 | adult tissue | metabolism | 845 | 369 | −0.7 |
| 12 | mammary epithelium | epithelia | 784 | 543 | 0.4 |
| 13 | CNS | neuronal development | 768 | 312 | −0.5 |
| 14 | PyMT tumor | odontogenesis | 1371 | 156 | 0.9 |
| 15 | mammary epithelium | epithelia | 2925 | 1923 | 1.0 |

TABLE 8-continued

Network modules of MaTARs

| MaTAR | Tissue expression | GO terms | kTotal | kWithin | Eigengene corr |
|---|---|---|---|---|---|
| 16 | mammary epithelium | epithelia | 2518 | 1633 | 0.9 |
| 17 | testis | spermatogenesis | 1562 | 1091 | 0.6 |
| 18 | embryonic liver | cell cycle | 742 | 74 | −0.7 |
| 19 | mammary | epithelium epithelia | 2190 | 1462 | 0.9 |
| 20 | mammary | epithelium epithelia | 979 | 531 | 0.5 |
| 21 | mammary | epithelium epithelia | 1717 | 1131 | 0.8 |
| 22 | mammary | epithelium epithelia | 1644 | 1132 | 0.8 |
| 23 | colon/intestine | digestion | 442 | 47 | 0.9 |
| 24 | mammary | epithelium epithelia | 739 | 268 | 0.4 |
| 25 | mammary | epithelium epithelia | 1599 | 1058 | 0.8 |
| 26 | mammary | epithelium epithelia | 1006 | 522 | 0.5 |
| 27 | CNS | neuronal development | 1400 | 720 | 0.8 |
| 28 | mammary | epithelium epithelia | 2308 | 1489 | 0.9 |
| 29 | CNS/embryonic proliferation | liver development, | 618 | 44 | 0.7 |
| 30 | mammary | epithelium epithelia | 3319 | 2178 | 1.0 |

Example 4: Antisense Inhibition of MaTARs in Primary Tumor Cells

Based on the computational results, it was proposed that MaTARs are driver genes in mammary cancer progression and/or metastasis and thus, could serve as novel therapeutic targets. This hypothesis was tested by performing antisense inhibition of MaTARs with ISIS oligonucleotides.

Antisense inhibition of 14 MaTARs was performed in primary MMTV-PyMT tumor cells to understand the role of MaTARs in mammary cancer progression and/or metastasis. To investigate the functional impact of MaTAR down-regulation on tumor cells, cell viability and invasion assays were conducted.

To generate primary mammary tumor cells, organoids were treated with 0.25% Trypsin and 0.1% EDTA in PBS for 5 min at 37° C. To stop the reaction, 10 mL DMEM/F12 medium supplemented with 10% FCS and 4 U/µL of DNase I (Sigma) was added and incubated for 15 min at 100 rpm and 37° C. The cell solution was spun down for 10 min at 520 g. The pellet was resuspended in 10 mL DMEM/F12 with 10% FCS and 1% penicillin/streptomycin and filtered via a 70 µM cell strainer. Three additional washing steps (centrifugation for 5 min at 520 g, resuspension of the pellet in 10 mL DMEM/F12 with 10% FCS and 1% penicillin/streptomycin) were performed. The final cell pellet was resuspended and cultured in DMEM/F12 medium supplemented with 10% FCS, 1% penicillin/streptomycin, and 5 µg/mL insulin (Sigma).

ISIS oligonucleotides tested in the assay, were designed as 5-10-5 MOE gapmers, and are 20 nucleosides in length, wherein the central gap segment is comprised of ten 2'-deoxynucleosides and is flanked on both sides (in the 5' and 3' directions) by wings comprising 5 nucleosides each. Each nucleoside in the 5' wing segment and each nucleoside in the 3' wing segment has a 2'-MOE modification. The internucleoside linkages throughout the gapmer are phosphorothioate (P=S) linkages. All cytosine residues throughout the gapmer are 5-methylcytosines. The ISIS oligonucleotide sequences are presented in the Table below. The MaTARs targeted by the ISIS oligonucleotides are also shown in the Table below. 'scASO' is a control oligonucleotide that is a 5-10-5 MOE gapmer with no known murine target.

TABLE 9

ISIS oligonucleotides targeting MaTARS

| MaTAR | ISIS No. | Sequence | SEQ ID NO |
|---|---|---|---|
| 1 | 710749 | TTTATGCTGGGACTAGTGAC | 157 |
| 3 | 710776 | TAACTCACTAATTTGGTAAA | 158 |
| 4 | 710763 | CGTCACCTACACTGAGGAGC | 159 |
| 5 | 710625 | CTCAGAGCTCAAAAGTTTTC | 160 |
| 6 | 710849 | CAGGCCCACAGCAGGCTCAA | 112 |
| 7 | 710716 | TCCCTCTGAGATCAAGCGGC | 161 |
| 8 | 710855 | CGGGTTGCTTTAGAGTGTTC | 162 |
| 9 | 714133 | TGGAGCTGATGGGCTTTTTG | 113 |
| 10 | 714110 | GCTGCGAGCACCCCTTCATT | 137 |
| 11 | 710707 | CAGGATCTCTGATGTGCAGG | 114 |
| 12 | 710814 | GGGATGAGCTCAGCCGGATC | 115 |
| 13 | 714039 | TATCAGGGTAGGTATCACAT | 116 |
| 14 | 714142 | TGATGTCTCATGACTGAGAG | 139 |
| 15 | 710700 | CATTCAGGTAATGTGTCACA | 163 |
| 16 | 710798 | TAAAGATATTGTCCCGTTGG | 117 |
| 17 | 710784 | TTACCAATTGAGCGACATCT | 118 |
| 18 | 710838 | CCCACAGGAGTTAGGGCTGC | 119 |
| 19 | 714079 | CAGGTGAAGCCACTCCTGCT | 164 |
| 20 | 710728 | GCTGGTCCAGAGAGCTTTCC | 120 |
| 21 | 710640 | CAGGCCCAGCCAGGTGCTTA | 165 |
| 22 | 710829 | TACCTTGACATTCCATGTAG | 121 |
| 23 | 714051 | AAGAACTTTTTAATATATAG | 166 |
| 24 | 710679 | TGCTTTATCCCATTGCAAGC | 150 |
| 25 | 710806 | GAAACACCCAGGTCATCCAG | 122 |
| 26 | 710752 | TAGCTGATGTTGCTGTAGCT | 123 |
| 27 | 714129 | CTCATTGTACTGCTTGCTGA | 167 |
| 28 | 710740 | TCAATCTTACAACAGCAAAG | 124 |
| 29 | 714102 | AGTCTGGCTTGGCCATGGCA | 168 |
| 30 | 714043 | TGCTGGTGCTGGACCAGGGC | 125 |
| scASO | 141923 | CCTTCCCTGAAGGTTCCTCC | 126 |

Antisense Inhibition

MMTV-PyMT primary cells were seeded at a density of 20,000 cells/well into 96-well plates. Transfection-free uptake of oligonucleotide was accomplished by adding 5 µM of either a MaTAR-specific oligonucleotide or the scASO to the primary cell culture medium immediately after seeding the cells. Cells were incubated for 24 hours at 37° C. and RNA was isolated using the RNeasy 96 kit (Qiagen), according to the manufacturer's instructions. RNA samples were used directly in a one-step 384-well qRT-PCR (QuantiTect SYBR Green RT-PCR Kit, Qiagen) on an Applied Biosystems 7900HT Fast Real-Time PCR System (Thermo Fisher Scientific). The results are presented in the Table below, and indicate knockdown efficiencies ranging from 38% for MaTAR26 to 89% for MaTAR13 after 24 hours.

TABLE 10

Antisense inhibition of MaTARs
in primary MMTV-PyMT cells

| MaTAR | ISIS No | % inhibition |
|---|---|---|
| 1 | 710749 | 64 |
| 3 | 710776 | 51 |
| 4 | 710763 | 32 |
| 5 | 710625 | 47 |
| 6 | 710849 | 69 |
| 7 | 710716 | 68 |
| 8 | 710855 | 72 |
| 9 | 714133 | 55 |
| 10 | 714110 | 61 |
| 11 | 710707 | 74 |
| 12 | 710814 | 69 |
| 13 | 714039 | 89 |
| 14 | 714142 | 68 |
| 15 | 710700 | 45 |
| 16 | 710798 | 47 |
| 17 | 710784 | 53 |
| 18 | 710838 | 52 |
| 19 | 714079 | 68 |
| 20 | 710728 | 72 |
| 21 | 710640 | 65 |
| 22 | 710829 | 54 |
| 23 | 714051 | 51 |
| 24 | 710679 | 57 |
| 25 | 710806 | 64 |
| 26 | 710752 | 38 |
| 27 | 714129 | 97 |
| 28 | 710740 | 69 |
| 29 | 714102 | 61 |
| 30 | 714043 | 55 |

Cell Viability

MMTV-PyMT primary tumor cells were seeded at a density of 10,000 cells/well into 96-well plates and treated with 5 µM of either a MaTAR-specific ISIS oligonucleotide or scASO. Cells were grown for 72 hours at 37° C. MTT solution at 10 µL volume (Cell Growth Determination Kit, MTT based; Sigma) was added to the wells and incubated for 4 hours at 37° C. Next, 100 µL MTT solvent was added directly to the wells to ensure total solubility of the formazan crystals and incubated for 10 min with shaking. Measurements of absorbance at 570 nm were performed using a SpectraMax i3 Multi-Mode Detection Platform (Molecular Devices). Background absorbance at 690 nm was subtracted. Percent viability in the ISIS oligonucleotide-treated wells was calculated as a percentage of the control. Significant changes were defined as a consistent reduction ≥25% of viability or invasion compared to untreated control cells. The results indicated that knockdown of MaTAR12 lead to a 50% decrease in cell viability. Additionally, inhibition of MaTAR11, 18, and 20 also had a 20-30% decrease in cell viability. There was no effect on cell viability with the scASO.

To confirm the results obtained with the MTT assay, protease activity within living cells was measured separately on a subset of the MaTARs and similar results were obtained.

TABLE 11

Cell viability (% untreated control)
after antisense inhibition of MaTARs

| MaTAR | ISIS No | % viability |
|---|---|---|
| 1 | 710749 | 117 |
| 3 | 710776 | 99 |
| 4 | 710763 | 108 |
| 5 | 710625 | 98 |
| 6 | 710849 | 77 |
| 7 | 710716 | 93 |
| 8 | 710855 | 101 |
| 9 | 714133 | 88 |
| 10 | 714110 | 86 |
| 11 | 710707 | 75 |
| 12 | 710814 | 49 |
| 13 | 714039 | 100 |
| 14 | 714142 | 105 |
| 15 | 710700 | 105 |
| 16 | 710798 | 101 |
| 17 | 710784 | 87 |
| 18 | 710838 | 73 |
| 19 | 714079 | 95 |
| 20 | 710728 | 70 |
| 21 | 710640 | 94 |
| 22 | 710829 | 95 |
| 23 | 714051 | 103 |
| 24 | 710679 | 102 |
| 25 | 710806 | 106 |
| 26 | 710752 | 90 |
| 27 | 714129 | 102 |
| 28 | 710740 | 104 |
| 29 | 714102 | 83 |
| 30 | 714043 | 81 |

Invasion Potential

The invasion potential of MMTV-PyMT primary tumor cells was assessed using the QCM 96-well Invasion Assay Kit (ECM555; Millipore). Cells were starved in DMEM/F12 serum-free medium for 24 hours, then harvested and seeded at a density of $1\times10^5$ cells/well into the invasion chamber. MaTAR-specific ISIS oligonucleotide or scASO at 5 µM was added to the growth medium. The plate was incubated at 37° C. for 24 hours and the assay was performed according to the manufacturer's instructions. Briefly, the tumor cells that invaded the ECM layer and attached to the bottom of the invasion chamber were collected using cell detachment solution and lysed in 1: 75 CyQuant GR dye lysis buffer. As a negative control, serum-free medium was used that did not stimulate cell invasion through the ECM. 150 µL of cell lysates were transferred to a new 96-well plate and the fluorescence was measured with a SpectraMax i3 Multi-Mode Detection Platform (Molecular Devices) using the 480 nm/520 nm filter set. The results are presented in the Table below. Significant reduction of tumor cell invasion upon antisense inhibition of MaTAR13 (49% inhibition) and MaTAR9 (36% inhibition) was detected. Furthermore, 25-45% reduction of invasive potential was observed upon independent knockdown of 15 candidates; MaTAR8, 9, 13, 14, 15, 16, 17, 19, 20, 21, 23, 24, 25, 28, and 29.

TABLE 12

Invasive potential (% control) after
antisense inhibition of MaTARs

| MaTAR | % invasion |
|---|---|
| 25 | 55 |
| 16 | 58 |
| 21 | 59 |
| 24 | 60 |
| 23 | 65 |
| 15 | 65 |
| 17 | 65 |

TABLE 12-continued

Invasive potential (% control) after antisense inhibition of MaTARs

| MaTAR | % invasion |
|---|---|
| 9 | 65 |
| 20 | 68 |
| 8 | 69 |
| 13 | 70 |
| 29 | 70 |
| 19 | 72 |
| 14 | 74 |
| 28 | 75 |
| 7 | 79 |
| 30 | 82 |
| 22 | 83 |
| 11 | 87 |
| 10 | 88 |
| 18 | 88 |
| 3 | 88 |
| 27 | 94 |
| 5 | 95 |
| 26 | 95 |
| 6 | 101 |
| 4 | 102 |
| 1 | 111 |
| 12 | 121 |
| scASO | 77 |
| Serum-free control | 14 |

While 9 of the 14 tested MaTARs seem to impact either the viability or the invasive potential of mammary tumor cells, indicating specific roles of the different non-coding transcripts in cellular processes, two MaTARs (11 and 20) show effects in both assays. Viability and invasion potential also correlated well with knockdown efficiency of the ISIS oligonucleotides. The data is summarized in the Table below. Reduction of viability, invasive potential or branching of >25% compared to untreated cells is defined as a significant difference and is marked with an asterisk. These results also confirm that the initial computational selection of up-regulated lncRNAs indeed identified transcripts that have the potential to act as driver genes in tumor progression.

TABLE 13

Observed effects after antisense inhibition of MaTARs

|  | Viability | Invasion | Branching |
|---|---|---|---|
| MaTAR1 | 117 | 111 | 99 |
| MaTAR3 | 99 | 88 | 83 |
| MaTAR4 | 108 | 102 | 88 |
| MaTAR5 | 98 | 95 | 83 |
| MaTAR6 | 77* | 101 | 75* |
| MaTAR7 | 93 | 79* | 87 |
| MaTAR8 | 101 | 69* | 87 |
| MaTAR9 | 88 | 65* | 82 |
| MaTAR10 | 86 | 88 | 78 |
| MaTAR11 | 75 | 87 | 72 |
| MaTAR12 | 49* | 121 | 50* |
| MaTAR13 | 100 | 70* | 80 |
| MaTAR14 | 105 | 74* | 81 |
| MaTAR15 | 105 | 65* | 85 |
| MaTAR16 | 101 | 58* | 62* |
| MaTAR17 | 87 | 65* | 61* |
| MaTAR18 | 73* | 88 | 60* |
| MaTAR19 | 95 | 72* | 71* |
| MaTAR20 | 70* | 68* | 68* |
| MaTAR21 | 94 | 59* | 86 |
| MaTAR22 | 95 | 83 | 83 |
| MaTAR23 | 103 | 65* | 84 |
| MaTAR24 | 102 | 60* | 86 |
| MaTAR25 | 106 | 55* | 56* |

TABLE 13-continued

Observed effects after antisense inhibition of MaTARs

|  | Viability | Invasion | Branching |
|---|---|---|---|
| MaTAR26 | 90 | 95 | 65* |
| MaTAR27 | 102 | 94 | 77 |
| MaTAR28 | 104 | 75* | 57* |
| MaTAR29 | 83 | 70* | 78 |
| MaTAR30 | 81 | 82 | 85 |

Example 5: Effect of Antisense Inhibition of MaTARs in Organoids

To further elucidate the functional role of MaTARs in a more physiological context, antisense inhibition was performed in mammary tumor organoids (Barcellos-Hoff et al, Development 105: 223-235, 1989; Fata et al, Dev. Biol. 306: 193-207, 2007; Ewald et al, Dev. Cell 14: 570-581, 2008; Nguyen-Ngoc et al, Proc. Natl. Acad. Sci. USA 109: E2595-604, 2012). Organoids mimic aspects of the three-dimensional organization of an organ more closely than individual cells cultured in two-dimension.

Organoids were prepared and cultured as described in the Examples above. ISIS oligonucleotides tested in the assay, were designed as 5-10-5 MOE gapmers, and are 20 nucleosides in length, wherein the central gap segment is comprised of ten 2'-deoxynucleosides and is flanked on both sides (in the 5' and 3' directions) by wings comprising 5 nucleosides each. Each nucleoside in the 5' wing segment and each nucleoside in the 3' wing segment has a 2'-MOE modification. The internucleoside linkages throughout the gapmer are phosphorothioate (P=S) linkages. All cytosine residues throughout the gapmer are 5-methylcytosines. The ISIS oligonucleotide sequences are presented in the Table below. The MaTARs targeted by the ISIS oligonucleotides are also shown in the Table below. For some MaTARs, multiple ISIS oligonucleotides were designed to different regions of the transcript.

TABLE 14

ISIS oligonucleotides tested in mammary tumor organoids

| MaTAR | ISIS No. | sequence | SEQ ID NO |
|---|---|---|---|
| 1 | 710743 | AAAGCCATCGGCAGTTTCCA | 127 |
| 3 | 710773 | AGTCCTGCTCGGCATGAATT | 128 |
| 4 | 710765 | GAAACCTCGGACTTTATTCA | 129 |
| 5 | 710631 | TTAGAGTTGTTCACAGTCGG | 130 |
| 6 | 710845 | CTGGAGGAGGAACAGTTTCA | 131 |
| 7 | 710712 | TGTAGCCACTGCCACCACCA | 132 |
|  | 710719 | ACCCATTGCTTCTGAGCAGA | 133 |
| 8 | 710856 | CCTTTCTAAGATGACACATT | 134 |
|  | 710858 | ACATTAGGAGGCCAACTCAG | 135 |
| 9 | 714132 | CCGGAGGATGACCAGTGTGG | 136 |
| 10 | 714110 | GCTGCGAGCACCCCTTCATT | 137 |
| 11 | 710707 | CAGGATCTCTGATGTGCAGG | 114 |
| 12 | 710814 | GGGATGAGCTCAGCCGGATC | 115 |
| 13 | 714039 | TATCAGGGTAGGTATCACAT | 116 |
|  | 714040 | AAGGGTACAGTTTGCTCTGC | 138 |
| 14 | 714142 | TGATGTCTCATGACTGAGAG | 139 |
| 15 | 710697 | GTTGGTTCTGCAGCTTTATC | 140 |
| 16 | 710795 | CTTTCACACTGGGTGAGTAT | 141 |
|  | 710797 | CACTTCCAGTAAGATTACAT | 142 |
|  | 710798 | TAAAGATATTGTCCCGTTGG | 117 |
| 17 | 710783 | CATCTTCAAAGGCAACTGGC | 143 |
|  | 710784 | TTACCAATTGAGCGACATCT | 118 |
| 18 | 710833 | CTGGCATAGCTGCAGGCAAA | 144 |
|  | 710836 | TTCAAGCCCATATGTGAGGC | 145 |
|  | 710838 | CCCACAGGAGTTAGGGCTGC | 119 |

TABLE 14-continued

ISIS oligonucleotides tested in mammary tumor organoids

| MaTAR | ISIS No. | sequence | SEQ ID NO |
|---|---|---|---|
| 19 | 714077 | TGCAGCCAGGGAGAGGCACA | 146 |
| 20 | 710728 | GCTGGTCCAGAGAGCTTTCC | 120 |
| 21 | 710635 | GCTGCTTCCTCTGCCAGAAG | 147 |
| 22 | 710828 | TTGTCCATAGGTTCAGAGGT | 148 |
| 23 | 714057 | CAGGACCCATAGTGGTTTGC | 149 |
| 24 | 710679 | TGCTTTATCCCATTGCAAGC | 150 |
| 25 | 710804 | GAGTCTGGACACATGATACT | 151 |
| 26 | 710752 | TAGCTGATGTTGCTGTAGCT | 123 |
|  | 710759 | GCCTCAAGTTTACCAGTAGG | 152 |
|  | 710761 | CCCCAAGACATTATTTAAGG | 153 |
| 27 | 714128 | AGCCACTGATCCATTTATTG | 154 |
| 28 | 710740 | TCAATCTTACAACAGCAAAG | 124 |
|  | 710741 | GTGGATCTTGGATTGGCTGC | 155 |
| 29 | 714107 | TCCCATTGCTGGTGCTGGAC | 156 |
| 30 | 714043 | TGCTGGTGCTGGACCAGGGC | 125 |
| scASO | 141923 | CCTTCCCTGAAGGTTCCTCC | 126 |

Organoids were seeded at a density of 5 organoids/4 and plated as 80 µL domes in Cellstar 24-well dishes (Greiner Bio One). Transfection-free uptake of ISIS oligonucleotides was accomplished by adding 4 µM of either a MaTAR-specific oligonucleotide or scASO to the organoid medium 15-20 min after the organoids were plated in the matrigel domes. Organoids were incubated for 6 days at 37° C. and both medium and oligonucleotide were replenished at day 3. Knockdown efficiencies in the organoids ranged from 30-68% after 6 days of treatment. The results are presented in the Table below.

TABLE 15

Antisense inhibition of MaTARs in mammary tumor organoids

| MaTAR | % inhibition |
|---|---|
| 1 | 34 |
| 3 | 44 |
| 4 | 30 |
| 5 | 49 |
| 6 | 42 |
| 7 | 52 |
| 8 | 67 |
| 9 | 53 |
| 10 | 56 |
| 11 | 68 |
| 12 | 50 |
| 13 | 66 |
| 14 | 55 |
| 15 | 36 |
| 16 | 48 |
| 17 | 51 |
| 18 | 47 |
| 19 | 50 |
| 20 | 50 |
| 21 | 64 |
| 22 | 48 |
| 23 | 46 |
| 24 | 37 |
| 25 | 46 |
| 26 | 43 |
| 27 | 60 |
| 28 | 61 |
| 29 | 50 |
| 30 | 34 |

Culturing organoids for several days also allowed observation of phenotypic changes caused by the knockdown. Untreated MMTV-PyMT organoids, as well as organoids treated with scASO, generally exhibited branching in about 70-75% of all organoids. Treatment with ISIS oligonucleotides resulted in a decrease by 25-50% in branching morphogenesis for MaTAR6, 11, MaTAR12, 16, 17, 18, 19, 20, 25, 26, and 28. There was also a decrease of 20-30% for MaTAR6, 10, 11, 19, 27, and 29. The results are presented in the Table below. The mean of two biological replicates is shown; the total number of assayed organoids per treatment was 200.

Many of the MaTARs that interfered with cell viability and/or invasion in 2D assays also inhibited branching defects in the organoids. For instance, antisense inhibition of MaTAR17 and MaTAR28 caused a reduction in organoid branching and both transcripts demonstrate a role in invasion in 2D culture (as shown in Tables 9 and 10).

TABLE 16

Quantification of tumor organoid branching in mammary tumor organoids

|  | % branched organoids |
|---|---|
| Untreated cells | 73 |
| scASO | 70 |
| MaTAR12 | 37 |
| MaTAR25 | 41 |
| MaTAR28 | 42 |
| MaTAR18 | 44 |
| MaTAR17 | 45 |
| MaTAR16 | 46 |
| MaTAR26 | 47 |
| MaTAR20 | 50 |
| MaTAR19 | 52 |
| MaTAR11 | 53 |
| MaTAR6 | 55 |
| MaTAR27 | 56 |
| MaTAR10 | 57 |
| MaTAR29 | 57 |
| MaTAR13 | 59 |
| MaTAR14 | 59 |
| MaTAR9 | 60 |
| MaTAR5 | 60 |
| MaTAR22 | 61 |
| MaTAR3 | 61 |
| MaTAR23 | 61 |
| MaTAR30 | 62 |
| MaTAR15 | 62 |
| MaTAR24 | 63 |
| MaTAR21 | 63 |
| MaTAR7 | 63 |
| MaTAR8 | 64 |
| MaTAR4 | 65 |
| MaTAR1 | 72 |

Further studies were conducted with antisense inhibition of MaTAR16 (ENSMUSG00000086249, Gm12724), MaTAR18 (ENSMUSG00000085873, Ttc39aos1), and MaTAR26 (ENSMUSG00000097378, B230208H11Rik). The three lncRNA represent different gene biotypes; MaTAR16 is classified as 'processed transcript', MaTAR18 as 'antisense', and MaTAR26 as 'lincRNA'. Both MaTAR16 and MaTAR26 are part of the "mammary epithelium" module, while MaTAR18 resides in another highly interesting module that is comprised of the gene-expression signature for embryonic stem cells and embryonic liver. Knockdown experiments were performed with three different ISIS oligonucleotides for each transcript to ensure that the observed phenotypes were not caused by off-target effects. Treatment with ISIS oligonucleotides followed the same protocol as described above. The potency of each ISIS oligonucleotide is presented in the Table below.

Phenotypes of the organoids after treatment with the two most potent ISIS oligonucleotides per transcript are shown in comparison to organoids that were either untreated or treated with scASO (FIG. 1). Knockdown of MaTAR16 and MaTAR26 completely abolished organoid branching, while down-regulation of MaTAR18 resulted in organoids without defined branches and only tiny protrusions. In addition, it was observed that organoids treated with ISIS oligonucleotides targeting MaTAR16 were smaller than untreated or scASO-treated organoids. Individual knockdown efficiencies correlate well with the quantitation of branching, as shown in the Table below. Compared to untreated controls, there was reduction in branching of 48% for MaTAR16, 40% for MaTAR18, and 35% for MaTAR26, with the most potent ISIS oligonucleotide, respectively.

TABLE 17

Effect of inhibition of MaTARs on branching

|  | ISIS No | % inhibition | % branched organoids |
|---|---|---|---|
| MaTAR16 | 710797 | 24 | 60 |
|  | 710795 | 47 | 47 |
|  | 710798 | 61 | 39 |
| MaTAR18 | 710833 | 33 | 62 |
|  | 710836 | 51 | 43 |
|  | 710838 | 68 | 45 |
| MaTAR26 | 710761 | 32 | 59 |
|  | 710752 | 41 | 44 |
|  | 710759 | 41 | 46 |

To further support the role of MaTAR16, MaTAR18, and MaTAR26 as key genes in tumor progression, antisense inhibition of these MaTARs was performed in control organoids derived from WT nulliparous mammary glands. Antisense inhibition of each MaTAR is presented in the Table below. Knockdown efficiencies of the ISIS oligonucleotides were comparable to that in tumor organoids. However, there was no observed loss of branching in the normal mammary gland organoids after ISIS oligonucleotide treatment, strongly indicating the cancer-specific role of these three lncRNAs (FIG. 2). In addition, this experiment served as another control, confirming that the observed reduction in branching morphogenesis of tumor organoids is not due to ASO-induced toxicity or off-target effects.

Data on branching quantitation is also presented in the Table below. The mean of three biological replicates is shown; the total number of assayed organoids per treatment was 300. Branching in untreated organoids was 67% and in scASO-treated organoids was 57%.

TABLE 18

Effect of inhibition of MaTARs on branching in normal mammary organoids

|  | ISIS No | % inhibition | % branched organoids |
|---|---|---|---|
| MaTAR16 | 710795 | 60 | 46 |
|  | 710798 | 50 | 51 |

TABLE 18-continued

Effect of inhibition of MaTARs on branching in normal mammary organoids

|  | ISIS No | % inhibition | % branched organoids |
|---|---|---|---|
| MaTAR18 | 710836 | 44 | 54 |
|  | 710838 | 30 | 50 |
| MaTAR26 | 710752 | 40 | 49 |
|  | 710759 | 38 | 49 |

In order to exclude the possibility that the results were dependent on the genomic background of the mice, these findings were confirmed in organoids derived from C57/Bl6 MMTV-PyMT mice. Knockdown efficiencies and branching quantification in that model are presented in the Table below and FIG. 3. The mean of three biological replicates is shown; totally number of assayed organoids per treatment was 300. The results indicate that treatment with ISIS oligonucleotides resulted in very similar phenotypes for MMTV-PyMT organoids generated from both FVB and C57/Bl6 backgrounds.

TABLE 19

Effect of inhibition of MaTARs in C57/Bl6 MMTV-PyMT mammary organoids

|  | ISIS No | % inhibition | % branched organoids |
|---|---|---|---|
| MaTAR16 | 710795 | 50 | 47 |
|  | 710798 | 41 | 46 |
| MaTAR18 | 710836 | 43 | 44 |
|  | 710838 | 43 | 47 |
| MaTAR26 | 710752 | 43 | 51 |
|  | 710759 | 39 | 46 |

Example 6: Identification of Human Orthologs of MaTAR Genes

To confirm the relevance of MaTARs in breast cancer, the human orthologs of many of the MaTAR genes were identified.

Mouse and human transcripts were compared on the level of both sequence conservation and genomic location. If the mouse MaTAR sequence matched an annotated human gene using BLAT (BLAST-like alignment tool), the respective transcript was defined as the human counterpart of the mouse MaTAR. Since many non-coding RNAs are conserved between different species on the level of genomic location rather than based on sequence, the analysis was extended to synteny by analyzing the neighboring genes of each hMaTAR gene. The complete list of the genomic location of potential human MaTARs (hMaTARs) are provided in the Table below. Many hMaTARs are located in clusters of two or more non-coding genes in the genome, resulting in a total of 41 identified potential hMaTARs. 'r.i' indicates a retained intron; 'p.t.' indicates a processed transcript.

TABLE 20

| MaTAR | Mouse gene name | Human counterpart (seq, hg38) | Human counterpart (synteny, hg38) | Human gene location (hg38) | SEQ ID NOs |
|---|---|---|---|---|---|
| MaTAR1 | C130071C03Rik | LINC00461 | LINC00461 | chr5:88540779-88684803 (−) | 1 |
| MaTAR2 | Gm7582 | FAM96B | — | chr16:66932055-66934423 (−) | 2 |
| MaTAR3 | A730020E08Rik | AF065393.1 | un-annotated sequence upstream of Ccser1 (seq and synteny) | chr4:90121784-90121954 (−) | 3 |
| MaTAR4 | Hotairm1, Gm15051, Hoxaas1 | HOTAIRM1 | HOTAIRM1 | chr7:27096094-27100258 (+) | 4 |
| MaTAR5 | Gm14046 | PPIAP22 | — | chr21:18857779-18858276 (+) | 5 |
| MaTAR6 | 4833427F10Rik | HCG20 | cluster of lncRNAs in both mouse and human. HCG20 or LINC00243 | chr6:30766825-30792250 (+), chr6:30812866-30830659 (−) | 6-7 |
| MaTAR7 | Foxd2os, 9130206I24Rik | FOXD2-AS1 | — | chr1:47432133-47434641 (−) | 8 |
| MaTAR8 | Gm20544, lncRNA-Smad7 | — | un-annotated sequence upstream of Smad7 (seq and synteny); alternatively: RP11-1058N17.1 | chr18:48955665-48956059 (+) | 9-10 |
| MaTAR9 | Gm5637 | ARPC1B r.i./p.t., PDAP1 | — | chr7:99374675-99394781 (+), chr7:99394676-99408682 (−) | 11-12 |
| MaTAR10 | Gm9025, Ncf2-rs | NCF2 | cluster of many lncRNAS upstream of MAP3K1, most likely: RPL26P19 | chr1:183555563-183590876 (−) | 13-17 |
| MaTAR11 | AI427809, LOC381524 | — | un-annotated sequence upstream of ABCA1 within a cluster of non-coding RNAs, most likely: RP11-217B7.2 | chr9:104927553-104928892 (+) | 18 |
| MaTAR12 | Gm16010 | — | un-annotated sequence upstream/exon1 of SPSB4; alternatively: RP11-231L11.1 | chr3:141050613-141052013 (−), chr3:141115124-141124182 (−) | 19-20 |
| MaTAR13 | Gm15433 | — | AC009950.2 | chr2:230125310-230167494 (+) | 21 |
| MaTAR14 | Gm16025 | SP140 r.i. | — | chr2:230309741-230311581 (−), chr2:230401360-230401793 (−) | 22-23 |
| MaTAR15 | Gm6977 | FTH1P8 | cluster of non-coding RNAs and retrotransposons downstream of MAGEB1, most likely: GS1-383H3.7 | chrX:148052233-148052746 (+), chrX:30290047-30290351 (−) | 24-26 |
| MaTAR16 | Gm12724 | — | RP11-101C11.1 | chr1:55217861-55234177(+) | 27-28 |
| MaTAR17 | 4933404O12Rik | AF065393.1 | RP11-132A1.4 | chr7:101308346-101310985 (+) | 29-31 |
| MaTAR18 | Ttc39aos1, Gm12750 | TTC39A-AS1 | TTC39A-AS1 | chr1:51329654-51331281(+) | 32 |
| MaTAR19 | Gm15753 | — | RP11-44M6.1 | chr7:100509717-100519926 (+) | 33 |
| MaTAR20 | Gm13387 | — | RP13-122B23.8 | chr9:137293868-137295721 (−) | 34-35 |
| MaTAR21 | Gm2420 | SFI1 r.i./p.t. | — | chr22:31617011-31617070 (+) | 36 |
| MaTAR22 | 4930430E12Rik | — | RP11-114M5.3 | chr8:58503588-58504068 (+) | 37 |
| MaTAR23 | Naip3, Birc1c, EG667838, Naip-rs5 | NAIP | — | chr5: 70968483-71025114 (−) | 38 |
| MaTAR24 | Gm12504 | PTMAP5 | HMGB3P24 | chr13: 81689911-81691072 (+), chr9:36303499-36304924 (−) | 39-40 |

TABLE 20-continued

Potential human counterparts of MaTARs (hMaTARs)

| MaTAR | Mouse gene name | Human counterpart (seq, hg38) | Human counterpart (synteny, hg38) | Human gene location (hg38) | SEQ ID NOs |
|---|---|---|---|---|---|
| MaTAR25 | 1200007C13Rik | — | cluster of four/three lncRNAs in both mouse and human. LINC01271, LINC01270 or LINC01272 | chr20:50310711-50321342 (−), chr20:50292720-50314922 (+), chr20:50267486-50279795 (+) | 41-43 |
| MaTAR26 | B230208H11Rik | — | un-annotated sequence downstream of STX11 (seq and synteny), alternatively: TPT1P4 or RP1-91J24.1 | chr6:144200447-144200965 (−), chr6:144257034-144257624 (−) | 44-46 |
| MaTAR27 | Gm4750 | ACTB | AC234031.1 | chr7:5527155-5529569 (−), chrX:53001527-53001617 (+) | 47-48 |
| MaTAR28 | Gm12730 | — | RP11-101C11.1 or GYG1P3 | chr1:55217861-55234177 (+), chr1:55222379-55223372 (+) | 49-51 |
| MaTAR29 | Gm14328 | — | RP11-699C17.1 | chr18:50256036-50256461 (−) | 52-53 |
| MaTAR30 | Gm6166 | — | RP11-151H2.3 | chr15:74976240-74976573 (−) | 54-56 |

To evaluate the expression status of the potential hMaTARs, RNA-seq data of The Cancer Genome Atlas (TCGA) was analyzed by comparing breast tumors to matched normal tissues of 103 individuals. The analysis was performed on the Cancer Genomics Cloud hosted by Seven Bridges Genomics (http://www.sbgenomics.com). Raw RNA-seq reads were mapped to hg38 and counted. The GENCODE v24 GTF was used as a reference. For each individual, the tumor and matched normal sample datasets were analyzed independently. Fold changes calculated for individuals were averaged and statistical significance was calculated using Wilcoxon rank tests; p-values were adjusted using the Benjamini & Hochberg method.

Out of 41 hMaTARs, there was differential gene expression observed in 40, as shown in the Table below. hMaTAR3 was dropped out due to insufficient read coverage (denoted as na). Notably, at least 28 hMaTARs were found to be up-regulated in breast tumors, 19 of these with high statistical significance (adj. p<0.05), confirming the results from the initial RNA-seq screen in mouse models that identified multiple lncRNAs as potentially clinically revelevant. 'log 2FC' indicates a log 2-fold change in an average of 103 patients; 'DE' indicates differential gene expression; 'adj. p-value' indicates Wilcoxon rank sum test, p-value adjusted using the Benjamini & Hochberg method.

TABLE 21

Differential expression of hMaTARs in breast tumors compared to normal tissue

| hMaTAR | Gene ID | Ensembl ID | log2FC | DE | adj. p-value |
|---|---|---|---|---|---|
| hMaTAR1 | LINC00461 | ENSG00000245526 | 0.81 | 1.76 | 6.40E−05 |
| hMaTAR2 | FAM96B | ENSG00000166595 | 0.14 | 1.10 | 2.75E−02 |
| hMaTAR3 | AF065393.1 | ENSG00000274152 | na | na | na |
| hMaTAR4 | HOTAIRM1 | ENSG00000233429 | −1.42 | 0.37 | 6.70E−15 |
| hMaTAR5 | PPIAP22 | ENSG00000198618 | 0.72 | 1.65 | 1.78E−15 |
| hMaTAR6.1 | HCG20 | ENSG00000228022 | 0.23 | 1.17 | 1.14E−02 |
| hMaTAR6.2 | LINC00243 | ENSG00000214894 | 1.03 | 2.04 | 1.60E−08 |
| hMaTAR7 | FOXD2-AS1 | ENSG00000237424 | 0.54 | 1.45 | 2.29E−07 |
| hMaTAR8 | RP11-1058N17.1 | ENSG00000266905 | 0.03 | 1.02 | 1.00E+00 |
| hMaTAR9 | PDAP1 | ENSG00000106244 | 0.40 | 1.32 | 4.02E−09 |
| hMaTAR10.1 | NCF2 | ENSG00000116701 | 0.44 | 1.35 | 7.94E−04 |
| hMaTAR10.2 | RPL26P19 | ENSG00000226221 | −0.43 | 0.74 | 9.44E−07 |
| hMaTAR11 | RP11-217B7.2 | ENSG00000226334 | −0.39 | 0.76 | 1.85E−04 |
| hMaTAR12.1 | SPSB4 | ENSG00000175093 | 0.03 | 1.02 | 1.00E+00 |
| hMaTAR12.2 | RP11-231L11.1 | ENSG00000251270 | −0.03 | 0.98 | 1.00E+00 |
| hMaTAR13 | AC009950.2 | ENSG00000225963 | −0.11 | 0.93 | 8.49E−01 |
| hMaTAR14 | SP140 | ENSG00000079263 | 0.74 | 1.67 | 2.58E−08 |
| hMaTAR15.1 | FTH1P8 | ENSG00000219507 | 0.10 | 1.07 | 1.69E−01 |
| hMaTAR15.2 | GS1-383H3.7 | ENSG00000270794 | 0.05 | 1.03 | 4.85E−02 |
| hMaTAR16 | RP11-101C11.1 | ENSG00000231090 | 0.02 | 1.01 | 7.40E−01 |
| hMaTAR17.1 | AZGP1P2 | ENSG00000214252 | 0.22 | 1.16 | 8.88E−01 |
| hMaTAR17.2 | RP11-132A1.4 | ENSG00000232445 | 0.90 | 1.87 | 3.09E−07 |
| hMaTAR18 | TTC39A-AS1 | ENSG00000261664 | 0.62 | 1.54 | 2.16E−03 |
| hMaTAR19 | RP11-44M6.1 | ENSG00000225807 | −0.32 | 0.80 | 7.49E−07 |

TABLE 21-continued

Differential expression of hMaTARs in breast tumors compared to normal tissue

| hMaTAR | Gene ID | Ensembl ID | log2FC | DE | adj. p-value |
|---|---|---|---|---|---|
| hMaTAR20 | RP13-122B23.8 | ENSG00000260996 | 0.38 | 1.30 | 2.26E−05 |
| hMaTAR21 | SFI1 | ENSG00000198089 | 0.29 | 1.22 | 2.87E−03 |
| hMaTAR22 | RP11-114M5.3 | ENSG00000254103 | −0.07 | 0.95 | 8.20E−02 |
| hMaTAR23 | NAIP | ENSG00000249437 | 0.09 | 1.07 | 1.00E+00 |
| hMaTAR24.1 | PTMAP5 | ENSG00000214182 | 0.47 | 1.38 | 2.46E−08 |
| hMaTAR24.2 | HMGB3P24 | ENSG00000215283 | −0.16 | 0.90 | 7.66E−02 |
| hMaTAR25.1 | LINC01270 | ENSG00000203999 | 0.33 | 1.25 | 3.14E−02 |
| hMaTAR25.2 | LINC01271 | ENSG00000233077 | 0.25 | 1.19 | 9.42E−03 |
| hMaTAR25.3 | L1NC01272 | EN5G00000224397 | 0.24 | 1.18 | 1.12E−01 |
| hMaTAR26.1 | TPT1P4 | EN5G00000217027 | −0.71 | 0.61 | 3.27E−09 |
| hMaTAR26.2 | RP1-91124.1 | EN5G00000216475 | −0.08 | 0.95 | 2.83E−01 |
| hMaTAR27.1 | ACTB | EN5G00000075624 | 0.45 | 1.37 | 1.36E−08 |
| hMaTAR27.2 | AC234031.1 | EN5G00000278536 | 0.00 | 1.00 | 1.00E+00 |
| hMaTAR28.1 | RP11-101C11.1 | EN5G00000231090 | 0.02 | 1.01 | 7.40E−01 |
| hMaTAR28.2 | GYG1P3 | ENSG00000231095 | 0.05 | 1.03 | 2.66E−01 |
| hMaTAR29 | RP11-699C17.1 | ENSG00000277310 | 0.33 | 1.26 | 2.97E−04 |
| hMaTAR30 | RP11-151H2.3 | ENSG00000261813 | −0.02 | 0.99 | 1.00E+00 |

Further investigation was conducted on whether hMaTARs are expressed in subtype-specific manner by analyzing all TCGA breast tumor samples with subtype information (463 datasets). The analysis of raw RNA-Seq reads was performed as described above. Transcript abundances were quantified using RSEM quantification suite (li and Dewey, 2011) with default parameters. For each resultant RNA expression profile, normalized read counts of individual genes were obtained by applying the DESeq normalization implemented in the DESeq Bioconductor package. Genes whose median expression count across profiles was zero were excluded from further consideration. Kruskal-Wallis non-parametric test was used to assess differential expression for each of the remaining genes and for three different data partitions: by molecular subtype, by the estrogen receptor status, and by the progesterone receptor status.

Of the 19 up-regulated hMaTARs, 11 had significantly different expression (q<5.00E-11, same range as PAM50 genes (Parker et al, 2009)) among the five TCGA subtypes "basal", "Her2-amplified", "luminal A", "luminal B", and "normal-like". The results are presented in the Tables below. 'Subtype' indicates the correlation with breast cancer subtype, q-values were determined by Kruskal-Wallis test; 'ER' indicates the correlation with the estrogen receptor status, q-values were determined by Wilcoxon test; 'PR' indicates correlation with the progesterone receptor status, q-values were determined by Wilcoxon test. A decimal point and number after each MaTAR signifies that there is more than one possible ortholog for that MaTAR.

TABLE 22

Correlation of hMaTAR expression and breast cancer subtype or hormone receptor status

| hMaTAR | Ensembl ID | Subtype q-value | ER q-value | PR q-value |
|---|---|---|---|---|
| hMaTAR1 | ENSG00000245526 | 1.80E−17 | 4.46E−11 | 3.98E−11 |
| hMaTAR2 | ENSG00000166595 | 2.60E−11 | 1.47E−06 | 5.64E−07 |
| hMaTAR4 | ENSG00000233429 | 1.77E−24 | 6.88E−07 | 2.02E−04 |
| hMaTAR6.1 | ENSG00000228022 | 4.03E−10 | 1.43E−07 | 2.06E−04 |
| hMaTAR6.2 | ENSG00000214894 | 3.46E−15 | 1.10E−11 | 4.64E−04 |
| hMaTAR7 | ENSG00000237424 | 1.71E−06 | 1.03E−01 | 8.10E−02 |
| hMaTAR9 | ENSG00000106244 | 6.63E−09 | 8.09E−08 | 4.88E−06 |
| hMaTAR10.1 | ENSG00000116701 | 5.47E−07 | 3.07E−03 | 9.89E−02 |
| hMaTAR11 | ENSG00000226334 | 4.11E−03 | 5.26E−02 | 2.44E−01 |
| hMaTAR12.1 | ENSG00000175093 | 3.70E−06 | 1.94E−02 | 2.12E−01 |
| hMaTAR13 | ENSG00000225963 | 5.41E−05 | 4.76E−03 | 2.56E−02 |
| hMaTAR14 | ENSG00000079263 | 2.37E−07 | 6.56E−05 | 2.43E−03 |
| hMaTAR17.2 | ENSG00000232445 | 2.81E−11 | 5.86E−08 | 5.13E−04 |
| hMaTAR18 | ENSG00000261664 | 5.54E−37 | 2.88E−29 | 1.46E−17 |
| hMaTAR20 | ENSG00000260996 | 2.06E−10 | 4.93E−07 | 9.96E−05 |
| hMaTAR21 | ENSG00000198089 | 5.84E−23 | 1.03E−21 | 5.66E−15 |
| hMaTAR23 | ENSG00000249437 | 1.76E−12 | 1.11E−15 | 5.48E−10 |
| hMaTAR25.1 | ENSG00000203999 | 1.62E−07 | 6.06E−06 | 1.03E−02 |
| hMaTAR25.2 | ENSG00000233077 | 1.25E−06 | 1.91E−04 | 6.48E−02 |
| hMaTAR25.3 | ENSG00000224397 | 1.14E−26 | 3.11E−16 | 3.79E−10 |
| hMaTAR27.1 | ENSG00000075624 | 1.25E−11 | 9.31E−11 | 4.80E−05 |
| hMaTAR29 | ENSG00000277310 | 3.01E−17 | 1.98E−14 | 1.55E−13 |

TABLE 23

Expression levels (log) of hMaTARs

| | Basal | Her2 | LumA | LumB | Normal |
|---|---|---|---|---|---|
| ENSG00000245526 (hMaTAR1) | 4.1 | 1.4 | 0.0 | 1.0 | 1.0 |
| ENSG00000233429 (hMaTAR4) | 6.1 | 4.5 | 5.1 | 4.2 | 6.2 |

TABLE 23-continued

| Expression levels (log) of hMaTARs | | | | | |
|---|---|---|---|---|---|
| | Basal | Her2 | LumA | LumB | Normal |
| ENSG00000214894 (hMaTAR6.2) | 1.8 | 3.5 | 3.5 | 3.1 | 3.6 |
| ENSG00000261664 (hMaTAR18) | 2.8 | 4.9 | 5.9 | 5.7 | 5.3 |
| ENSG00000198089 (hMaTAR21) | 9.0 | 9.3 | 9.8 | 9.9 | 9.5 |
| ENSG00000224397 (hMaTAR25.3) | 7.3 | 7.0 | 5.0 | 6.1 | 6.4 |
| ENSG00000075624 (hMaTAR27.1) | 17.6 | 17.6 | 17.2 | 17.1 | 17.3 |
| ENSG00000277310 (hMaTAR29) | 1.1 | 1.7 | 2.4 | 2.1 | 1.3 |

In addition, hMaTAR4 and hMaTAR23 showed strong subtype-specificity, indicating that these lncRNAs may be clinically relevant in certain subtypes despite not being significantly up-regulated across the board, as shown in Table 21.

hMaTAR1 lncRNA was up-regulated the most in the original screen (Tables 4 and 5) by 80- and >100-fold in Her2-amplified and PyMT tumors, respectively). hMATAR1 is also significantly over-expressed in breast tumors compared to normal breast tissue (Table 21). This analysis was confirmed using previously published TCGA datasets (Yan et al, 2015). A slight, but significant up-regulation was also detected in kidney carcinoma as well as substantial over-expression in lung squamous cell carcinoma, as shown in the Table below. FDR<0.00001; KIRC=kidney renal clear cell carcinoma; BRCA—breast invasive carcinoma; LUSC=lung squamous cell carcinoma.

TABLE 24

| Expression fold-change compared to normal of hMATAR1 published TCGA RNA-seq datasets | |
|---|---|
| Cancer type | Fold-change |
| KIRC | 0.08 |
| BRCA | 5.26 |
| LUSC | 5.88 |

Moreover, statistically significant differences in the expression levels of hMaTAR1 comparing different subtypes of breast cancer were observed with lowest level in the luminal A and highest levels in the basal subtype (Table 22). Notable, there was a strong correlation of high hMaTAR1 levels and negative ER/PR status, matching the subtype data. Similar observations were made for 7 additional hMaTARs (Table 23, and as shown in the Tables below).

TABLE 25

| Differential gene expression levels (log) of hMaTARs associated with estrogen receptor (ER) status | | |
|---|---|---|
| | ER Negative | ER Positive |
| ENSG00000245526 (hMaTAR1) | 3.7 | 0.6 |
| ENSG00000214894 (hMaTAR6.2) | 2.0 | 3.4 |
| ENSG00000261664 (hMaTAR18) | 3.2 | 5.7 |
| ENSG00000198089 (hMaTAR21) | 9.1 | 9.8 |
| ENSG00000249437 (hMaTAR23) | 9.0 | 10.0 |
| ENSG00000224397 (hMaTAR25.3) | 7.2 | 5.6 |
| ENSG00000075624 (hMaTAR27.1) | 17.6 | 17.2 |
| ENSG00000277310 (hMaTAR29) | 1.2 | 2.3 |

TABLE 26

| Differential gene expression levels (log) of hMaTARs associated with progestrone receptor (PR) status | | |
|---|---|---|
| | PR Negative | PR Positive |
| ENSG00000245526 (hMaTAR1) | 2.9 | 0.0 |
| ENSG00000261664 (hMaTAR18) | 4.4 | 5.7 |
| ENSG00000198089 (hMaTAR21) | 9.3 | 9.8 |
| ENSG00000249437 (hMaTAR23) | 9.2 | 10.0 |
| ENSG00000224397 (hMaTAR25.3) | 6.8 | 5.6 |
| ENSG00000277310 (hMaTAR29) | 1.4 | 2.3 |

For hMaTAR1, the effect of its expression on overall patient survival was assessed using the log-rank test to compare outcomes for patients in the top quartile by the expression of the candidate gene to those in the bottom quartile. Notably, the survival analysis revealed that patients with low levels of hMaTAR1 survive an average of 1,500 days (approximately 4 years) longer than patients with high levels of this lncRNA, as shown in the Table below.

TABLE 27

| Surival probability curve for luminal B subtype breast cancer | |
|---|---|
| Upper Quartile | Survival time (days) |
| Sample 1 | 612 |
| Sample 2 | 811 |
| Sample 3 | 825 |
| Sample 4 | 1365 |
| Sample 5 | 1563 |
| Sample 6 | 1694 |
| Sample 7 | 1699 |
| Sample 8 | 2551 |
| Lower Quartile | Survival time (days) |
| Sample 9 | 558 |
| Sample 10 | 1542 |
| Sample 11 | 2097 |
| Sample 12 | 2422 |
| Sample 13 | 2469 |
| Sample 14 | 3941 |

Pathway analysis of TCGA data was also performed and a significant positive correlation of pathways, such as cell cycle and DNA replication, was observed, indicating the high proliferative rate of tumors with elevated hMaTAR1 levels. The data is presented in the Table below. The canonical pathways that are significantly over-represented among genes strongly correlated with hMaTAR1 were determined. Gene lists for each of the reactome canonical pathways were downloaded from the Reactome database in GMT format and Wilcoxon rank tests were conducted to compare correlations with hMaTAR1 of the genes in the pathway to those of the genes outside the pathway. The resulting p-values were Bonferroni-corrected to account for the number of pathways for which the tests were conducted.

TABLE 28

Reactome pathways positively or negatively correlated to hMaTAR1 expression

| Reactome ID | p-value |
|---|---|
| Positive Correlation | |
| Cell cycle | 5.30E-17 |
| DNA replication | 8.96E-17 |
| Cell cycle mitotic | 3.92E-16 |
| Mitotic M M G1 Phases | 1.27E-13 |
| DNA strand elongation | 8.80E-08 |
| Mitotic G1 G1 S Phases | 1.86E-06 |
| Activation of the pre-replicative complex | 3.50E-06 |
| Chromosome maintenance | 4.46E-06 |
| G2 M Checkpoints | 6.83E-06 |
| Mitotic prometaphase | 8.38E-06 |
| Synthesis of DNA | 9.30E-05 |
| S phase | 1.20E-04 |
| Activation of ATR in response to replication stress | 1.30E-04 |
| M G1 transition | 1.50E-04 |
| G1 S Transition | 3.15E-04 |
| G1 S specific transcription | 1.01E-03 |
| Extension of telomeres | 1.63E-03 |
| Unwinding of DNA | 1.86E-03 |
| Negative Correlation | |
| Phospholipid metabolism | 1.01E-04 |
| Signaling of PDGF | 6.53E-04 |
| Metabolism of lipids and lipoproteins | 8.82E-04 |
| Signaling of NGF | 1.01E-03 |
| NGF signaling via TRKA from plasma membrane | 1.79E-03 |

Example 7: Antisense Inhibition of MaTARs In Vivo

To further elucidate the functional role of MaTARs, antisense inhibition of selected MaTARs was performed in MMTV-PyMT nice, representing the luminal B type of breast cancer. The effect of antisense inhibition of MaTAR in vivo by subcutaneous injections of antisense oligonucleotides into MMTV-PyMT (FVB) mice was conducted and tumor growth, progression, and metastasis were monitored.

Groups of 4 mice each were first injected with tumor cells. The treatment with antisense oligonucleotide was started when tumors were palpable (4-5 mm in diameter). Mice were injected subcutaneously three times a week with 50 mg antisense oligonucleotide per kg body weight per day, resulting in a weekly dose of 150 mg/kg of antisense oligonucleotide. Scrambled antisense oligonucleotide served as the control. Each Table represents an independent experiment. Tumor size was measured twice a week using calipers. Treatments continued until one of tumors reached 2 cm in diameter, after which the mice were euthanized. Antisense oligonucleotides complementary to MaTAR20, MaTAR28, MaTAR17, MaTAR25, and MaTAR3 were tested. The data is presented in the Table below. The results show that antisense inhibition resulted 52% reduction of tumor volume for MaTAR3, 22% reduction for MaTAR17, 17% reduction for MaTAR20, and 40% reduction for MaTAR25.

TABLE 29

Mean tumor volume (mm$^3$) after antisense inhibition of MaTAR20 and MaTAR28 expression

| Time point | scASO | MaTAR20 | MaTAR28 |
|---|---|---|---|
| Week 1 | 46 | 38 | 21 |
|  | 58 | 59 | 26 |
| Week 2 | 147 | 73 | 71 |
|  | 143 | 82 | 64 |
| Week 3 | 148 | 129 | 85 |
|  | 147 | 124 | 134 |
| Week 4 | 130 | 203 | 179 |
|  | 172 | 302 | 167 |
| Week 5 | 155 | 286 | 221 |
|  | 210 | 242 | 382 |
| Week 6 | 263 | 219 | 446 |
|  | 232 | 193 | 554 |
| Week 7 | 269 | 244 | 277 |

TABLE 30

Mean tumor volume (mm$^3$) after antisense inhibition of MaTAR17 and MaTAR25 expression

| Time point | scASO | MaTAR17 | MaTAR25 |
|---|---|---|---|
| Week 1 | 0 | 0 | 1 |
|  | 0 | 0 | 0 |
| Week 2 | 0 | 10 | 4 |
|  | 6 | 21 | 11 |
| Week 3 | 4 | 16 | 10 |
|  | 22 | 25 | 24 |
| Week 4 | 30 | 25 | 29 |
|  | 63 | 43 | 61 |
| Week 5 | 78 | 44 | 69 |
|  | 90 | 42 | 65 |
| Week 6 | 179 | 66 | 102 |
|  | 261 | 129 | 166 |
| Week 7 | 268 | 190 | 189 |
|  | 278 | 182 | 172 |
| Week 8 | 519 | 268 | 303 |
|  | 506 | 316 | 354 |
| Week 9 | 648 | 561 | 478 |
|  | 898 | 702 | 541 |

TABLE 31

Mean tumor volume (mm$^3$) after antisense inhibition of MaTAR3 expression

| Time point | scASO | MaTAR3 |
|---|---|---|
| Week 1 | 144 | 156 |
|  | 142 | 131 |
| Week 2 | 139 | 133 |
|  | 143 | 137 |
| Week 3 | 143 | 145 |
|  | 144 | 150 |
| Week 4 | 269 | 230 |
|  | 399 | 283 |
| Week 5 | 591 | 330 |
|  | 719 | 329 |
| Week 6 | 1123 | 546 |

All the mice were euthanized when one of the tumors reached 2 cm in diameter. The lungs were then examined for the presence of metastatic nodules. Nodules were counted and the data is presented in the Tables below. There was a 68% reduction in metastases in the lungs with antisense inhibition of MaTAR20 and 31% reduction with antisense inhibition of MaTAR3.

TABLE 32

Average number of metastatic modules after antisense inhibition of MaTAR expression

| Treatment | Average metastatic nodules |
|---|---|
| scASO | 15 |
| MaTAR17 | 20 |
| MaTAR20 | 5 |
| MaTAR25 | 19 |
| MaTAR28 | 17 |

TABLE 33

Average number of metastatic modules after antisense inhibition of MaTAR3 expression

| Treatment | Average metastatic nodules |
|---|---|
| scASO | 20 |
| MaTAR3 | 14 |

The results of the in vivo knockdown experiment are summarized in the Table below.

TABLE 34

Summary of antisense inhibition of MaTAR expression

| Candidate | ASO (Ionis no.) | Metastasis | Tumor growth |
|---|---|---|---|
| MaTAR3 | 710772 | −31% | −52% |
| MaTAR17 | 710783 | +36% | −22% |
| MaTAR20 | 710725 | −68% | −17% |
| MaTAR25 | 710806 | +23% | −40% |
| MaTAR28 | 710740 | +15% | +95% |

Example 8: CRISPR/Cas9-Mediated Knockout of MaTAR25

To confirm the results observed on antisense inhibition of MaTAR25, the CRISPR-Cas9 system (Ran et al, 2013) was used to generate genetic knockout clones of MaTAR25 in the highly metastatic mammary cell line 4T1. The results show that the genetic loss of MaTAR25 significantly reduced tumor cell invasion, recapitulating the antisense oligonucleotide-mediated knockdown.

By introducing Cas9 and two guide RNAs (gRNAs) targeting regions upstream and downstream of the transcription start site of MaTAR25, deletions of the MaTAR25 promoter region were generated, resulting in an efficient depletion of MaTAR25 expression. The results are presented in the Table below. As a negative control, Cas9 and a gRNA targeting Renilla luciferase was introduced into 4T1 cells, which is referred to as '4T1 control' below.

TABLE 35

Relative MaTAR25 expression compared to 4T1 control in the MaTAR25 knockout (KO) clones

|  | Expression |
|---|---|
| 4T1 control | 1.00 |
| MaTAR25 KO clone1 | 0.03 |
| MaTAR25 KO clone2 | 0.01 |
| MaTAR25 KO clone3 | 0.03 |

The MaTAR25 KO cells were functionally compared with the 4T1 control cells. For this, 50,000 cells of each clone were seeded and manual cell counting was performed after 48 h and 72 h. The results show significant decrease in the cell proliferation rate in MaTAR25 KO clones (approximately 62% compared to control at day 4). The average of 3 cell counts is presented in the Table below.

TABLE 36

Number of cells of 4T1 control and MaTAR25 knockout (KO) clones

|  | 0 h | 48 h | 72 h |
|---|---|---|---|
| 4T1 control | 0.5 | 3.0 | 10.8 |
| MaTAR25 KO clone1 | 0.5 | 1.7 | 5.5 |
| MaTAR25 KO clone2 | 0.5 | 1.7 | 6.1 |
| MaTAR25 KO clone3 | 0.5 | 1.7 | 4.6 |

To further characterize the MaTAR25 KO clones, a cell migration assay was performed using live cell imaging. An Observer Live Cell Microscope (Zeiss) was used to acquire images every 5 minutes of the same image field in 12-well tissue culture plates for 8 hours, and images of 5 individual fields per group were collected for migration analysis. The collected images were analyzed using the CellTracker image processing software. Reduced cell motility by 40% was observed upon genetic loss of MaTAR25. The results are presented of the relative migration distance.

TABLE 37

Relative migration distance (μm) of 4T1 control and MaTAR25 knockout (KO) clones

|  | Distance |
|---|---|
| 4T1 control | 1.0 |
| MaTAR25 KO clone1 | 0.6 |
| MaTAR25 KO clone2 | 0.7 |
| MaTAR25 KO clone3 | 0.5 |

In addition, invasion assays were performed using 24-well Boyden chambers (TREVIGEN) in 24 hours. The results showed reduced cell invasion by 45% of MaTAR25 KO cells compared to 4T1 control cells. The results are presented as the average of 3 relative invasions in the Table below. 'No serum' denotes a positive control where cells should not invade in the absence of serum.

TABLE 37

Relative invaded cells

|  | Distance |
|---|---|
| No serum | 0.2 |
| 4T1 control | 1.0 |
| MaTAR25 KO clone1 | 0.4 |
| MaTAR25 KO clone2 | 0.5 |
| MaTAR25 KO clone3 | 0.6 |

Example 9: Further Identification of Human Orthologs of MaTAR Genes

Human orthologs of several other MaTAR genes were identified using the methodology described in Example 6. The complete list of the genomic location of potential human MaTARs (hMaTARs) are provided in the Table below.

TABLE 38

Potential human counterparts of MaTARs (hMaTARs)

| Ensembl ID | MaTAR | transcript ID | Human counterpart (sequence, hg38) | Human gene location (sequence, hg38) | human synteny (hg38) | SEQ ID NO |
|---|---|---|---|---|---|---|
| ENSMUSG00000085399 | MaTAR31 (also MaTAR7) | ENSMUST00000123272 | | | | |
| ENSMUSG00000100816 | MaTAR32 | ENSMUST00000187677 | intron of non-coding RNA CNIH3 | chr3:1473111-1473137 (+), chr1:224490851-224490882 (−) | ENST00000414394.1 (chr2:192,629,919-192,645,706), ENST00000422017.1 (chr2:192,644,102-192,645,387) | 193-196 |
| ENSMUSG00000096617 | MaTAR33 | ENSMUST00000180755 | retro-GAPDH | | RP11-62517.1 (chr4:77,394,491-77,494,286) | 197 |
| ENSMUSG00000104000 | MaTAR34 | ENSMUST00000195727 | | chr3:35423136-35423173 (+) | ENST00000615633.1 (chr8:81,356,161-81,356,274), ENST00000518880.1 (chr8:81,279,871-81,281,446), ENST00000606235.1 (chr8:81,275,399-81,277,570) | 198-201 |
| ENSMUSG00000104645 | MaTAR35 | ENSMUST00000200327 | intron of RAD51B | chr14:68,214,801-68,214,832 | ENST00000515649.1 (chr4:104,907,406-104,970,084), ENST00000580856.2 (chr4:104,796,128-104,796,221), ENST00000515127.1 (chr4:104,653,874-104,966,793), ENST00000508358.1 (chr4:104,556,960-104,568,877) | 202-206 |
| ENSMUSG00000105811 | MaTAR36 | ENSMUST00000196668 | | chr1:87673467-87673600 (+) | ENST00000437598.1 (chr1:87,899,909-87,905,714); chr1:87900099-87976514; chr1:87,805,286-87,808,372; chr1:87526364-87529941 | 207-211 |
| ENSMUSG00000082292 | MaTAR37 | ENSMUST00000164282 | intron of CAMTA1 | chr19:34,709,167-34,709,419; chr1:7,032,170-7,032,239 | ENST00000408204.2 (chr5:155,024,714-155,024,800); chr5:155116572-155119608 | 212-215 |
| ENSMUSG00000106230 | MaTAR38 | ENSMUST00000197386 | | chr4:87,891,842-87,892,832 | ENST00000513220.1 (chr4:106,003,317-106,022,478) | 216-217 |
| ENSMUSG00000099375 | MaTAR39 | ENSMUST00000186885 | intron of LINC01648 | chr1:30,026,649-30,027,342 | ENST00000430692.1 (chr2:125,710,969-125,765,842); ENST00000455174.2 (chr2:126,110,099-126,117,985); ENST00000435352.1 (chr2:126,308,510-126,343,992) | 218-221 |
| ENSMUSG00000085218 | MaTAR40 | ENSMUST00000123623 | | chr11:30,635,647-30,638,513 | ENST00000531002.1 (chr11:30,584,130-30,630,508); chr11:30686409-30695389; chr11:30687409-30697149; chr11:30741556-30793130 | 222-226 |
| ENSMUSG00000100009 | MaTAR41 | ENSMUST00000191042 | intron of DAP3 | chr1:155,696,325-155,696,501 | ENST00000411055.1 (chr5:102,302,504-102,302,810); ENST00000506058.1 (chr5:102,144,077-102,146,572); | 227-231 |

TABLE 38-continued

Potential human counterparts of MaTARs (hMaTARs)

| Ensembl ID | MaTAR | transcript ID | Human counterpart (sequence, hg38) | Human gene location (sequence, hg38) | human synteny (hg38) | SEQ ID NO |
|---|---|---|---|---|---|---|
| | | | | | ENST00000362916.1 (chr5:102,131,007-102,131,135); ENST00000615759.1 (chr5:102,108,666-102,108,764) | |
| ENSMUSG00000087326 | MaTAR42 | ENSMUST00000146576 | intron of PCAT29 | chr15:69,631,165-69,631,311 | chr9:36307042-36315279; chr9:36313547-36315321 | 232-234 |
| ENSMUSG00000087107 | MaTAR43 | ENSMUST00000143673 | intron of AGBL4 | chr1:49,319,395-49,319,493 | ENST00000587012.1 (chr17:35,406,684-35,409,768); ENST00000592117.1 (chr17:35,403,837-35,404,373); ENST00000589099.1 (chr17:35,400,878-35,403,006) | 235-238 |
| ENSMUSG00000066170 | MaTAR44 | ENSMUST00000181029 | | chr1:61,652,871-61,653,084 | LOC285847 (chr6:35726762-35736947); ENST00000452048.1 (chr6:35,733,867-35,736,947) | 239-241 |
| ENSMUSG00000099848 | MaTAR45 | ENSMUST00000185425 | intron of TCONS_00011243 | chr6:167,686,270-167,686,755 | ENST00000629370.1 (chr2:234,682,668-234,717,764); ENST00000427619.5 (chr2:234,834,315-234,913,384); ENST00000413842.1 (chr2:234,882,279-234,888,802) | 242-245 |
| ENSMUSG00000104350 | MaTAR46 | ENSMUST00000191737 | | chr2:107,615,711-107,615,781 | ENST00000610049.1 (chr1:111,184,415-111,185,061); chr1:111251780-111252513 | 246-248 |
| ENSMUSG00000097639 | MaTAR47 | ENSMUST00000181833 | intron of SDK1 | chr7:4,176,549-4,176,613; chr3:114,206,658-114,207,102 | ENST00000487657.2 (chr4:128,582,999-128,601,400); ENST00000514265.1 (chr4:128,567,972-128,570,531); ENST00000608228.1 (chr4:128,552,590-128,553,416) | 249-253 |
| ENSMUSG00000105260 | MaTAR48 | ENSMUST00000196337 | intron of MAPK10 | chr4:86,369,041-86,369,080 | ENST00000511497.5 (chr4:128,428,070-128,519,394); ENST00000505133.5 (chr4:128,292,751-128,466,661) | 254-256 |
| ENSMUSG00000087362 | MaTAR49 | ENSMUST00000139492 | intron of DIAPH2 | chrX:97,035,752-97,035,829 | ENST00000434418.2 (chr2:187,712,816-188,287,691) | 257-258 |
| ENSMUSG00000100147 | MaTAR50 | ENSMUST00000189594 | | chr1:195,728,884-195,728,916 | ENST00000436706.1 (chr1:224,208,747-224,213,279) | 259-260 |
| ENSMUSG00000104192 | MaTAR51 | ENSMUST00000195679 | | chr1:102,480,764-102,480,794 | ENST00000451250.1 (chr1:55,217,861-55,234,177); LOC100507634 (chr1:55215408-55217455) | 261-263 |
| ENSMUSG00000105613 | MaTAR52 | ENSMUST00000199279 | | chr12:121,299,793-121,302,026 | chr12:121375393-121392412 | 264-265 |
| ENSMUSG00000105353 | MaTAR53 | ENSMUST00000198677 | intron of TCONS_00028092 | chr20:2,219,060-2,219,103 | chr4:16114342-16120917 | 266-267 |
| ENSMUSG00000103755 | MaTAR54 | ENSMUST00000192612 | | chr3:143,118,914-143,119,438 | ENST00000492307.1 (chr3:143,111,802-143,112,359) | 268-269 |

TABLE 38-continued

Potential human counterparts of MaTARs (hMaTARs)

| Ensembl ID | MaTAR | transcript ID | Human counterpart (sequence, hg38) | Human gene location (sequence, hg38) | human synteny (hg38) | SEQ ID NO |
|---|---|---|---|---|---|---|
| ENSMUSG00000105263 | MaTAR55 | ENSMUST00000200473 | | chr10:14,991,910-14,992,564 | chr4:16114342-16120917 | 270-271 |
| ENSMUSG00000101249 | MaTAR56 | ENSMUST00000187117 | intron of non-coding RNA RP11-3P22.2 | chr7:69,331,847-69,332,251 | — | 272 |
| ENSMUSG00000100131 | MaTAR57 | ENSMUST00000187714 | | chr16:10,722,204-10,722,741 | — | 273 |
| ENSMUSG00000097113 | MaTAR58 | ENSMUST00000181524 | intron of DNAJB4 | chr1:77,981,610-77,983,203 | ENST00000367355.5 (chr1:200,342,544-200,373,792) | 274-275 |
| ENSMUSG00000102070 | MaTAR59 | ENSMUST00000188231 | intron of RP11-3P22.2 | chr2:202,614,880-202,615,460, chr7:69,330,777-69,331,342 | — | 276-277 |
| ENSMUSG00000054418 | MaTAR60 | ENSMUST00000155384 | | chr17:77,904,130-77,904,532 | chr17:77934751-77935349; ENST00000374983.3 (chr17:77,879,027-77,884,087) | 278-280 |

Example 10: Antisense Inhibition of MaTARs in Primary Tumor Cells

Antisense inhibition of the MaTARs described in the previous Example was performed in primary MMTV-PyMT tumor cells.

ISIS oligonucleotides tested in the assay were designed as 5-10-5 MOE gapmers, and are 20 nucleosides in length, wherein the central gap segment is comprised of ten 2'-deoxynucleosides and is flanked on both sides (in the 5' and 3' directions) by wings comprising 5 nucleosides each. Each nucleoside in the 5' wing segment and each nucleoside in the 3' wing segment has a 2'-MOE modification. The internucleoside linkages throughout the gapmer are phosphorothioate (P=S) linkages. All cytosine residues throughout the gapmer are 5-methylcytosines. The ISIS oligonucleotide sequences are presented in the Table below. The MaTARs targeted by the ISIS oligonucleotides are also shown in the Table below.

TABLE 39

ISIS oligonucleotides targeting MaTARS

| MaTAR | ISIS No. | sequence | SEQ ID |
|---|---|---|---|
| 31 | 850592 | CCCCTAGGCAAGGTGGGTCC | 169 |
| 33 | 850868 | GCCAGCCCCGGCATCGAAGG | 170 |
| 36 | 850797 | CAAAAGCACACCCCGATGTC | 171 |
| 37 | 850578 | CACCAGCTTGTCCGCCACAG | 172 |
| 38 | 850701 | GATGCCTGAGGAAGCGCGCC | 173 |
| 39 | 850637 | GGTTCAGGTAGATGTACTTC | 174 |
| 40 | 850718 | GGCTGCCCAACCACTATGGT | 175 |
| 41 | 850671 | GATACTCATGATAAGGGATT | 176 |
| 42 | 850746 | TTACCCTCGCGGGTCCAGGC | 177 |
| 43 | 850744 | CAACCCGAGAATCACAAGAG | 178 |
| 44 | 850766 | GCCCGTTCCTCACAGCGGAT | 179 |
| 45 | 850831 | TCGCTCAGCTGCTCTGGTGT | 180 |
| 46 | 850779 | ATGTGGTGATCAACACTGGC | 181 |
| 49 | 850727 | GCCGCTGAAGCTGCACAGTA | 182 |
| 50 | 850664 | GGATGCCCCGTGGGTAGCAC | 183 |
| 51 | 850794 | GGCCCCTGATAGGTAGGCTC | 184 |
| 52 | 850706 | GCCACCGGGTGAGCGAGCCC | 185 |
| 53 | 850855 | CCGCTCTAACTTTCGCCCGA | 186 |
| 54 | 850678 | GGGACACCAGTGCTGACCGC | 187 |
| 55 | 850823 | GAGCTTGGTAGGCTCCATCT | 188 |
| 56 | 850598 | GGCGAAGTGGGCTTTTGCTC | 189 |

TABLE 39-continued

ISIS oligonucleotides targeting MaTARS

| MaTAR | ISIS No. | sequence | SEQ ID |
|---|---|---|---|
| 57 | 850621 | CGTCTAAGGTGTGTGTTGTG | 190 |
| 58 | 850819 | CGCTCCAGCCACGCGCAGAT | 191 |
| 59 | 850610 | GGCAGAACGACTCGGTTATC | 192 |

Antisense Inhibition

MMTV-PyMT primary cells were seeded at a density of 20,000 cells/well into 96-well plates. Transfection-free uptake of oligonucleotide was accomplished by adding 5 μM of either a MaTAR-specific oligonucleotide or the scASO to the primary cell culture medium immediately after seeding the cells. Cells were incubated for 24 hours at 37° C. and RNA was isolated using the RNeasy 96 kit (Qiagen), according to the manufacturer's instructions. RNA samples were used directly in a one-step 384-well qRT-PCR (QuantiTect SYBR Green RT-PCR Kit, Qiagen) on an Applied Biosystems 7900HT Fast Real-Time PCR System (Thermo Fisher Scientific). The results are presented in the Table below, and indicate knockdown efficiencies ranging from 4% for MaTAR50 to 89% for MaTAR56 after 24 hours.

TABLE 40

Antisense inhibition of MaTARs in primary MMTV-PyMT cells

| MaTAR | ISIS No. | % inhibition |
|---|---|---|
| 31 | 850592 | 26 |
| 33 | 850868 | 50 |
| 36 | 850797 | 36 |
| 37 | 850578 | 13 |
| 38 | 850701 | 13 |
| 39 | 850637 | 21 |
| 40 | 850718 | 20 |
| 41 | 850671 | 16 |
| 42 | 850746 | 40 |
| 43 | 850744 | 14 |
| 44 | 850766 | 57 |
| 45 | 850831 | 84 |
| 46 | 850779 | 53 |
| 49 | 850727 | 53 |

TABLE 40-continued

Antisense inhibition of MaTARs in primary MMTV-PyMT cells

| MaTAR | ISIS No. | % inhibition |
|---|---|---|
| 50 | 850664 | 4 |
| 51 | 850794 | 37 |
| 52 | 850706 | 59 |
| 53 | 850855 | 76 |
| 54 | 850678 | 27 |
| 55 | 850823 | 25 |
| 56 | 850598 | 89 |
| 57 | 850621 | 74 |
| 58 | 850819 | 74 |
| 59 | 850610 | 82 |

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11058709B1). An electronic copy of the "Sequence Listing" will also be available from the USPTO upon request and payment of the fee set forth in 37 CFR 1.19(b)(3).

What is claimed is:

1. A method of treating breast cancer in an animal comprising administering a therapeutically effective amount of a compound comprising a modified oligonucleotide 12 to 30 linked nucleosides in length and having a nucleobase sequence that is at least 90% complementary to a mammary tumor associated RNA (MaTAR) to the animal, thereby treating breast cancer in the animal.

2. The method of claim 1, wherein the MaTAR is selected from a group consisting of MaTAR 1-111 and 193-280.

3. The method of claim 1, wherein the animal is a human.

4. The method of claim 1, wherein the modified oligonucleotide has a nucleobase sequence that is at least 90% complementary, at least 95% complementary, or 100% complementary to an equal length portion of a nucleobase sequence selected from SEQ ID NOs: 1-111 and 193-280.

5. The method of claim 1, wherein the modified oligonucleotide is single-stranded.

6. The method of claim 1, wherein the modified oligonucleotide is double-stranded.

7. The method of claim 1, wherein the modified oligonucleotide comprises at least one modified internucleoside linkage, at least one modified sugar moiety, or at least one modified nucleobase.

8. The method of claim 7, wherein the at least one modified internucleoside linkage of the modified oligonucleotide is a phosphorothioate internucleoside linkage.

9. The method of claim 7, wherein the at least one modified sugar is a bicyclic sugar or 2'-O-methoxyethyl.

10. The method of claim 7, wherein the at least one modified nucleobase is a 5-methylcytosine.

11. The method of claim 9, wherein bicyclic sugar comprises a 4'-CH(CH$_3$)—O-2' bridge or a 4'-(CH$_2$)$_n$—O-2' bridge, wherein n is 1 or 2.

12. The method of claim 1, wherein the modified oligonucleotide comprises:
a gap segment consisting of linked deoxynucleosides;
a 5' wing segment consisting of linked nucleosides; and
a 3' wing segment consisting linked nucleosides,
wherein the gap segment is positioned immediately adjacent to and between the 5' wing segment and the 3' wing segment, and wherein each nucleoside of each wing segment comprises a modified sugar.

13. The method of claim 1, wherein the modified oligonucleotide comprises a portion of at least 8 contiguous nucleobases of a nucleobase sequence selected from SEQ ID NOs: 112-156 and 169-192.

14. The method of claim 13, wherein the modified oligonucleotide consists of 20 linked nucleosides and has a nucleobase sequence consisting of the nucleobase sequence of SEQ ID NO: 151.

15. The method of claim 14, wherein the modified oligonucleotide comprises:
a gap segment consisting of ten linked deoxynucleosides;
a 5' wing segment consisting of five linked nucleosides; and
a 3' wing segment consisting five linked nucleosides,
wherein the gap segment is positioned immediately adjacent to and between the 5' wing segment and the 3' wing segment, wherein each nucleoside of each wing segment comprises a 2'-O-methoxyethyl sugar modification, wherein each internucleoside linkage is a phosphorothioate linkage, and wherein each cytosine is 5-methylcytosine.

* * * * *